US012214130B2

(12) United States Patent
Silver et al.

(10) Patent No.: US 12,214,130 B2
(45) Date of Patent: Feb. 4, 2025

(54) SYSTEMS AND METHODS FOR ASSISTING PATIENT AIRWAY MANAGEMENT

(71) Applicant: ZOLL Medical Corporation, Chelmsford, MA (US)

(72) Inventors: Annemarie E Silver, Bedford, MA (US); Gary A Freeman, Waltham, MA (US); George Beck, Salem, MA (US); Guy R Johnson, Wilton, NH (US); Ulrich R Herken, Medford, MA (US); Wayne F Stanley, Merrimack, NH (US); Shin-Luen Chai, Groton, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

(21) Appl. No.: 18/405,319

(22) Filed: Jan. 5, 2024

(65) Prior Publication Data

US 2024/0293634 A1    Sep. 5, 2024

Related U.S. Application Data

(63) Continuation of application No. 17/644,141, filed on Dec. 14, 2021, now Pat. No. 11,904,095, which is a
(Continued)

(51) Int. Cl.
*A61M 16/00*    (2006.01)
*A61B 5/00*    (2006.01)
(Continued)

(52) U.S. Cl.
CPC ..... *A61M 16/0488* (2013.01); *A61B 5/02055* (2013.01); *A61B 5/08* (2013.01);
(Continued)

(58) Field of Classification Search
CPC .......... A61M 16/0488; A61M 16/0003; A61M 16/0084; A61M 16/0411; A61M 16/024;
(Continued)

(56) References Cited

U.S. PATENT DOCUMENTS 6,306,107 B1   10/2001   Myklebust et al.
6,334,070 B1   12/2001   Nova et al.
(Continued)

FOREIGN PATENT DOCUMENTS

CN   103402426 A   11/2013
CN   103619390 A   3/2014
(Continued)

OTHER PUBLICATIONS

European Search Report for EP Application No. 24160443.8, mailed on Sep. 3, 2024, 18 pages.
(Continued)

*Primary Examiner* — Steven O Douglas
(74) *Attorney, Agent, or Firm* — ZOLL Medical Corporation

(57) ABSTRACT

A medical system for assisting with an intubation procedure for a patient. The system comprising airflow sensors configured to obtain data indicative of airflow in the patient's airway and physiological sensors configured to obtain information regarding airflow in the patient's lungs. The system further including a monitoring device communicatively coupled to the airflow sensors and the physiological sensors. The patient monitoring device comprising at least one processor coupled to memory and configured to: provide a user interface on a display and assist the rescuer in determining proper placement of an endotracheal tube, receive the data indicative of the airflow in the patient's airway, receive the physiological information regarding the airflow in the patient's lungs, and determine whether the tube is
(Continued)

properly placed based on the received physiological information, and present an output of the determination of whether the ET tube was properly placed.

29 Claims, 35 Drawing Sheets

Related U.S. Application Data continuation of application No. 16/250,926, filed on Jan. 17, 2019, now Pat. No. 11,229,760.

(60) Provisional application No. 62/618,391, filed on Jan. 17, 2018.

(51) Int. Cl.

| | | |
|---|---|---|
| *A61B 5/0205* | (2006.01) | |
| *A61B 5/08* | (2006.01) | |
| *A61B 5/33* | (2021.01) | |
| *A61H 31/00* | (2006.01) | |
| *A61M 16/04* | (2006.01) | |
| *A61N 1/39* | (2006.01) | |
| *G16H 20/40* | (2018.01) | |
| *G16H 40/63* | (2018.01) | |
| *G16H 50/20* | (2018.01) | |
| *G16H 50/30* | (2018.01) | |
| *A61B 5/021* | (2006.01) | |
| *A61B 5/024* | (2006.01) | |
| *A61B 5/053* | (2021.01) | |
| *A61B 5/083* | (2006.01) | |
| *A61B 5/087* | (2006.01) | |
| *A61B 5/145* | (2006.01) | |
| *A61M 16/10* | (2006.01) | |

(52) U.S. Cl.
CPC .............. *A61B 5/33* (2021.01); *A61B 5/7435* (2013.01); *A61H 31/00* (2013.01); *A61M 16/0003* (2014.02); *A61M 16/0084* (2014.02); *A61M 16/024* (2017.08); *A61M 16/0411* (2014.02); *A61N 1/3904* (2017.08); *A61N 1/3925* (2013.01); *G16H 20/40* (2018.01); *G16H 40/63* (2018.01); *G16H 50/20* (2018.01); *G16H 50/30* (2018.01); *A61B 5/021* (2013.01); *A61B 5/024* (2013.01); *A61B 5/053* (2013.01); *A61B 5/0816* (2013.01); *A61B 5/0833* (2013.01); *A61B 5/0836* (2013.01); *A61B 5/087* (2013.01); *A61B 5/14542* (2013.01); *A61B 5/72* (2013.01); *A61H 2201/5089* (2013.01); *A61H 2230/04* (2013.01); *A61H 2230/08* (2013.01); *A61H 2230/40* (2013.01); *A61M 2016/003* (2013.01); *A61M 16/0051* (2013.01); *A61M 2016/0413* (2013.01); *A61M 2016/1025* (2013.01); *A61M 2016/103* (2013.01); *A61M 2205/18* (2013.01); *A61M 2205/3303* (2013.01); *A61M 2205/3317* (2013.01); *A61M 2205/3327* (2013.01); *A61M 2205/3375* (2013.01); *A61M 2205/3553* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/70* (2013.01); *A61M 2205/702* (2013.01); *A61M 2210/1039* (2013.01); *A61M 2230/04* (2013.01); *A61M 2230/205* (2013.01); *A61M 2230/432* (2013.01); *A61M 2230/435* (2013.01); *A61M 2230/60* (2013.01); *A61M 2230/63* (2013.01); *A61M 2230/65* (2013.01)

(58) Field of Classification Search
CPC ........ A61M 16/0051; A61M 2016/003; A61M 2016/0413; A61M 2016/1025; A61M 2016/103; A61M 2205/18; A61M 2205/3303; A61N 1/3904; A61N 1/3925; G16H 20/40; G16H 50/30; G16H 50/20; G16H 40/63; A61B 5/33; A61B 5/02055; A61B 5/08; A61B 5/7435; A61H 31/00; A61H 2201/5089; A61H 2230/04; A61H 2230/08; A61H 2230/40

See application file for complete search history.

(56) References Cited

U.S. PATENT DOCUMENTS

| | | |
|---|---|---|
| 6,351,671 B1 | 2/2002 | Myklebust et al. |
| 6,356,785 B1 | 3/2002 | Snyder et al. |
| 6,390,996 B1 | 5/2002 | Halperin et al. |
| 6,821,254 B2 | 11/2004 | Weil et al. |
| 6,827,695 B2 | 12/2004 | Palazzolo et al. |
| 7,220,235 B2 | 5/2007 | Geheb et al. |
| 7,277,752 B2 | 10/2007 | Matos |
| 7,308,304 B2 | 12/2007 | Hampton et al. |
| 7,310,553 B2 | 12/2007 | Freeman |
| 7,661,428 B2 | 2/2010 | Berthon-Jones |
| 7,747,319 B2 | 6/2010 | Freeman |
| 7,774,054 B2 | 8/2010 | Myklebust |
| 7,925,339 B2 | 4/2011 | Wik |
| 8,394,031 B2 | 3/2013 | Mansy et al. |
| 8,433,407 B2 | 4/2013 | Chapman et al. |
| 9,364,625 B2 | 6/2016 | Silver et al. |
| 9,375,381 B2 | 6/2016 | Freeman |
| 9,486,157 B2 | 11/2016 | Wik |
| 9,707,363 B2 | 7/2017 | Mansfield et al. |
| 9,826,956 B2 | 11/2017 | Freeman et al. |
| 10,137,265 B2 | 11/2018 | Freeman et al. |
| 2003/0018276 A1 | 1/2003 | Mansy et al. |
| 2003/0106553 A1 | 6/2003 | Vanderveen |
| 2005/0085799 A1 | 4/2005 | Luria et al. |
| 2006/0015044 A1 | 1/2006 | Stavland et al. |
| 2011/0201957 A1 | 8/2011 | Zhou et al. |
| 2012/0123223 A1 | 5/2012 | Freeman et al. |
| 2012/0220845 A1 | 8/2012 | Campbell |
| 2014/0180138 A1 | 6/2014 | Freeman et al. |
| 2014/0276173 A1 | 9/2014 | Banner et al. |
| 2015/0209532 A1 | 7/2015 | Efrati et al. |
| 2016/0022943 A1 | 1/2016 | Kanowitz |
| 2016/0206839 A1 | 7/2016 | Freeman et al. |
| 2016/0303389 A1 | 10/2016 | Peterson et al. |
| 2017/0238841 A1 | 8/2017 | Hemnes et al. |
| 2017/0266399 A1 | 9/2017 | Campana et al. |

FOREIGN PATENT DOCUMENTS

| | | |
|---|---|---|
| CN | 104918549 A | 9/2015 |
| CN | 104955509 A | 9/2015 |
| WO | 2006006870 A1 | 1/2006 |
| WO | 2017029629 A1 | 2/2017 |

OTHER PUBLICATIONS

International Search Report for PCT Application No. PCT/US2019/014073, dd Jul. 26, 2019, 8 pages*.

SYSTEMS AND METHODS FOR ASSISTING PATIENT AIRWAY MANAGEMENT

RELATED APPLICATIONS

This application claims priority to U.S. application Ser. No. 17/644,141, filed on Dec. 14, 2021, which claims priority to U.S. application Ser. No. 16/250,926, filed on Jan. 17, 2019, which claims priority under 35 U.S.C. § 119 (e) to U.S. Provisional Application Ser. No. 62/618,391, filed on Jan. 17, 2018, the entire contents of which are hereby incorporated by reference.

BACKGROUND

A tracheal tube is a conduit that is inserted into the trachea of a patient to establish and maintain a patient's airway. Tracheal tubes are frequently used for airway management in settings of general anesthesia, critical care and emergency medicine to provide mechanical ventilation. Tracheal tubes are used to ensure an adequate exchange of oxygen and carbon dioxide, to deliver oxygen in higher concentrations than found in air, or to administer other gases to a patient.

An endotracheal tube is a specific type of tracheal tube that is usually inserted through the mouth or nose. It is a breathing channel designed to be placed into the airway of critically injured, ill, or anesthetized subjects in order to perform positive pressure ventilation of the lungs and to prevent the possibility of aspiration or airway obstruction.

Endotracheal intubation generally refers to the procedure for placing a tracheal tube into the trachea of a patient to maintain an open airway, provide ventilatory assistance, or to serve as a conduit through which to administer certain drugs. Intubation is generally performed in critically injured, ill or anesthetized subjects to facilitate ventilation of the lungs and to prevent the possibility of asphyxiation, airway obstruction, or aspiration of gastric contents. To facilitate placement of the endotracheal tube, rapid sequence intubation (RSI) is a common method of prompt intubation of unconsciousness and neuromuscular blockage in emergency scenarios.

SUMMARY

An example of a medical system for assisting a rescuer with an intubation or other advanced airway procedure for a patient is described. The system may include an airflow sensor configured to obtain data indicative of airflow in the patient's airway, a physiological sensor configured to obtain information regarding airflow in the patient's lungs, and a patient monitoring device communicatively coupled to the airflow sensor and the physiological sensor. The patient monitoring device further includes at least one processor and memory. The at least one processor may be configured to receive the data indicative of the airflow in the patient's airway, determine the presence of airflow in the patient's airway based on the received data, initiate a timer based on the determined presence of airflow in the patient's airway setting an interval to confirm proper placement of the ET tube, receive the physiological information regarding the airflow in the patient's lungs, determine whether ET tube is properly placed within the predetermined interval based on the received physiological information, and present to the user interface an output of the determination of whether the ET tube is properly placed.

Implementations of such a system may include one or of the following features. The medical system may include one or more airflow sensors that comprise at least one of: an oxygen sensor for measuring a concentration of oxygen in the patient's airway, a flow sensor for measuring gas flow rate in the patient's airway, and a capnography sensor for measuring a concentration of $CO_2$ in the patient's airway. The medical system may include one or more physiological sensors that comprises at least one of: pulse oximeter for obtaining oxygen saturation information from the patient, a capnography sensor for obtaining ETCO2 information from the patient, ECG sensors for obtaining ECG signals from the patient, an acoustic sensor for obtaining acoustic information from the patient, impedance sensors for obtaining a transthoracic impedance of the patient, and non-invasive blood pressure sensors for obtaining blood pressure of the patient.

The medical system may include one or more physiological sensors that comprise at least one of the capnography sensor, the impedance sensors, and the acoustic sensor. The medical system may include a patient monitoring device that includes a defibrillator, the patient monitoring device comprises an automated external defibrillator or a professional style defibrillator.

The medical system may further include user interface for assisting the rescuer in determining proper placement of an endotracheal (ET) tube is configured to display visual feedback. The medical system may include visual feedback that includes at least one of: oxygen saturation, end tidal CO2 (ETCO2), ECG signals from the patient, acoustic information, a transthoracic impedance, blood pressure, body temperature, heart rate, and respiration rate.

The medical system may include a display that is a touchscreen display configured to receive input from the rescuer and wherein the patient monitor includes more or more inputs for receiving information from the rescuer. Additionally, the inputs include at least one of: softkeys, buttons, knobs, touchscreen inputs, and switches.

The medical system may further include one or more portable computing devices communicatively coupled to the patient monitoring device to transmit and receive patient information from the patient monitoring device. The medical system may include one or more portable computing devices that include at least one of a tablet computer, smartphone, and laptop, wherein the portable computing device includes a touchscreen display for receiving patient information from the rescuer, the patient information including at least one of: a height, a weight, and a gender of the patient. The medical system may include a portable computing device that connects to one or more central facilities to obtain additional patient information about the patient. The medical system may include determination of whether the ET tube was properly placed prior to the expiration of the timer and is displayed on at least one of the display of the patient monitoring device and the portable computing device.

The medical system may further provide physiological information for determining whether the ET tube is properly placed comprises an ETCO2 value meeting a predetermined criterion. The medical system may provide a predetermined criterion that comprises a measured ETCO2 value exceeding a predetermined threshold. The medical system may provide a predetermined criterion that comprises a trend in measured ETCO2 exceeding a predetermined threshold trend. The medical system may provide predetermined criterion that comprises a measured ETCO2 value being greater or less than a percentage of a moving average of a plurality of previously measured ETCO2 values. The medical system may provide predetermined criterion that comprises consecutive measured ETCO2 value being greater or less than a percentage of a moving average of a plurality of previously measured ETCO2 values.

The medical system may further provide physiological information for determining whether the ET tube is properly placed comprises a transthoracic impedance value meeting a predetermined criterion. The medical system may provide predetermined criterion that comprises a measured ETCO2 value exceeding a predetermined threshold.

The medical system may further provide predetermined criterion that includes a trend in measured ETCO2 exceeding a predetermined threshold trend. The medical system may provide at least one processor that is configured to initiate a timer based on the determined presence of airflow in the patient's airway. Additionally, the at least one processor may be configured to determine whether the ET tube is properly placed based prior to expiration of the timer. Additionally, the at least one processor may be configured to present the output to the user interface the determination of whether the ET tube was properly placed prior to the expiration of the timer. The medical system may further include a timer that is a default value between 5 and 15 seconds. Additionally, the medical system may further include a timer that is a user-defined value.

An example of a medical system for assisting a rescuer with an intubation procedure for a patient is described. The system may include one or more airflow sensors configured to obtain data indicative of airflow in the patient's airway; one or more physiological sensors configured to obtain physiological information regarding airflow in the patient's lungs; a patient monitoring device communicatively coupled to the one or more airflow sensors and the one or more physiological sensors. The patient monitoring device may include a user interface comprising a display, and at least one processor and memory configured to receive the data indicative of the airflow in the patient's airway, determine the presence of airflow in the patient's airway based on the received data, receive the physiological information regarding the airflow in the patient's lungs, determine a physiological baseline regarding airflow in the patient's lungs after placement of the ET tube, determine whether the ET tube remains properly placed based on a deviation from the physiological baseline, and present to the display of the user interface an output of the determination of whether the ET tube remains properly placed.

Implementations of such a medical system may include one or more of the following features. The physiological baseline may comprise an initial baseline determined upon initial placement of the ET tube. The initial baseline may include an average of a plurality of physiological values received upon initial placement of the ET tube. The deviation from the physiological baseline may include a percentage difference between a current physiological value and the initial baseline. The physiological baseline may include a dynamic baseline determined from updated physiological values obtained after initial tube placement. The dynamic baseline may include a moving average of a plurality of physiological values received after placement of the ET tube. The medical system may include one or more physiological sensors that includes at least one of a capnography sensor, acoustic sensor, and an impedance sensor. The medical system may include a one or more airflow sensors includes at least one of an oxygen sensor for measuring a concentration of oxygen in the patient's airway, a flow sensor for measuring gas flow rate in the patient's airway, and a capnography sensor for measuring a concentration of $CO_2$ in the patient's airway.

The medical system may include one or more physiological sensors including at least one of a capnography sensor for obtaining ETCO2 information from the patient, an acoustic sensor for obtaining acoustic information from the patient, and impedance sensors for obtaining a transthoracic impedance of the patient. The medical system may include one or more physiological sensors including the capnography sensor and the physiological baseline regarding the airflow in the patient's lungs including at least one ETCO2 value. The medical system may include at least one ETCO2 value includes an initial baseline determined upon initial placement of the ET tube. The medical system may include an initial baseline that is determined as an average of a plurality of ETCO2 values upon initial placement of the ET tube. The medical system may provide a deviation from the physiological baseline that includes a percentage difference between at least one current ETCO2 value and the initial baseline. The medical system may provide at least one ETCO2 value includes a dynamic baseline with continually updated ETCO2 values. The medical system may provide a dynamic baseline that includes a moving average of a plurality of ETCO2 values received after placement of the ET tube. The medical system may include one or more physiological sensors includes the transthoracic impedance sensor and the physiological baseline regarding the airflow in the patient's lungs includes at least one transthoracic impedance value. The medical system may provide at least one transthoracic impedance value that includes an initial baseline determined upon initial placement of the ET tube.

The medical system may provide an initial baseline that includes an average of a plurality of initial transthoracic impedance values received upon initial placement of the ET tube. The medical system may provide a deviation from the physiological baseline includes a percentage difference between a current transthoracic impedance value and the initial baseline. The medical system may provide at least one transthoracic impedance value includes a dynamic baseline with continually updated transthoracic impedance values. The medical system may provide a dynamic baseline includes a moving average of a plurality of transthoracic impedance values received after placement of the ET tube. The medical system may include one or more physiological sensors that includes the acoustic sensor and the physiological baseline regarding the airflow in the patient's lungs includes at least one spectral pattern. The medical system may provide at least one spectral pattern that includes an initial baseline determined upon initial placement of the ET tube. The medical system may provide an initial baseline that includes an average of a plurality of initial spectral components received upon initial placement of the ET tube. The medical system may provide a deviation from the physiological baseline that includes a percentage difference between a current spectral component and the initial baseline.

The medical system may provide at least one spectral pattern that includes a dynamic baseline with continually updated spectral pattern. The medical system may provide a dynamic baseline includes a moving average of a plurality of spectral components received after placement of the ET tube. The medical system may include a patient monitoring device that includes a defibrillator. The medical system may include a patient monitoring device that includes an automated external defibrillator or a professional style defibrillator. The medical system may include a user interface that is configured to display visual feedback. The medical system may provide a visual feedback that includes at least one of oxygen saturation, end tidal CO2 (ETCO2), ECG signals from the patient, acoustic information, a transthoracic impedance, blood pressure, body temperature, heart rate, and respiration rate. The medical system may include a display that is a touchscreen display configured to receive input from the rescuer. The medical system may include a patient monitoring device includes one or more inputs for receiving information from the rescuer. The medical system may include inputs that include at least one of softkeys, buttons, knobs, touchscreen inputs, and switches. The medical system may include one or more portable computing devices communicatively coupled to the patient monitoring device to transmit and receive patient information from the patient monitoring device.

The medical system may include one or more portable computing devices including at least one of a tablet computer, smartphone, and laptop. The medical system may include a portable computing device includes a touchscreen display for receiving patient information from the rescuer, the patient information including at least one of a height, a weight, and a gender of the patient. The medical system may include a portable computing device that connects to one or more central facilities to obtain additional patient information about the patient. The medical system may provide a determination of whether the ET tube remains properly placed that is displayed on at least one of the display of the patient monitoring device and the portable computing device. The medical system may include at least one processor that is configured to determine whether the ET tube remains properly placed prior to expiration of the timer. The medical system may include at least one processor that is configured to present the output of the determination of whether the ET tube remains properly placed prior to the expiration of the timer. The medical system may provide a timer that is a predefined value between 5 and 15 seconds. The medical system may provide a timer that is a user-defined value. The medical system may provide a determination of whether the ET tube remains properly placed that is based on a correlation between the received physiological information and the determined presence of airflow in the patient's airway. The medical system may provide a correlation that includes a confirmation that a positive pressure breath given to the patient has reached the patient's lungs. The medical system may provide a positive pressure breath given to the patient that results in the determined presence of airflow in the patient's airway.

The medical system of claim may include at least one processor and memory configured to determine a prior baseline before placement of the ET tube is initiated, and determine whether the ET tube is properly placed based on a deviation from the prior baseline. The medical system may include one or more impedance sensors for obtaining a transthoracic impedance of the patient, wherein the prior baseline is based on the transthoracic impedance of the patient.

An example of a medical system for assisting a rescuer with an intubation procedure for a patient is described. The system may include one or more airflow sensors configured to obtain data indicative of airflow in the patient's airway, one or more capnography sensors configured to obtain CO2 information regarding airflow in the patient's lungs, a patient monitoring device communicatively coupled to the one or more airflow sensors and the one or more capnography sensors, the patient monitoring device comprising a user interface comprising a display, and at least one processor and memory configured to receive the data indicative of the airflow in the patient's airway, determine the presence of airflow in the patient's airway based on the received data, receive the CO2 information regarding the airflow in the patient's lungs, determine whether the ET tube remains properly placed based on the received CO2 information, and present to the display of the user interface an output of the determination of whether the ET tube remains properly placed.

Implementations of such a medical system may include one or more of the following features. The CO2 information for determining whether the ET tube remains properly placed may include an ETCO2 value meeting a predetermined criterion. The medical system may provide a predetermined criterion that includes a deviation from a physiological baseline regarding airflow in the patient's lungs. The medical system may include at least one processor and memory that is configured to determine the physiological baseline after initial placement of the ET tube. The medical system may provide a physiological baseline that is an initial baseline determined upon initial placement of the ET tube. The medical system may include an initial baseline includes an average of a plurality of initial ETCO2 values received upon initial placement of the ET tube. The medical system may provide a deviation from the physiological baseline that includes a percentage difference between a current ETCO2 value and the initial baseline. The medical system may provide a physiological baseline that is a dynamic baseline with continually updated ETCO2 values measured after initial tube placement. The medical system may provide a dynamic baseline includes a moving average of a plurality of ETCO2 values received after placement of the ET tube. The medical system may include a one or more airflow sensors includes at least one of an oxygen sensor for measuring a concentration of oxygen in the patient's airway, and a flow sensor for measuring gas flow rate in the patient's airway.

The medical system may provide a predetermined criterion that includes an ETCO2 value exceeding a predetermined threshold. The medical system may provide a predetermined criterion includes an ETCO2 value falling within a desired range. The medical system may provide an ETCO2 value that is determined as an average of a plurality of ETCO2 values, and the predetermined criterion includes the average ETCO2 value exceeding the predetermined threshold. The medical system may provide an ETCO2 value that is determined as an average of a plurality of ETCO2 values, and the predetermined criterion includes the average ETCO2 value falling within the desired range. The medical system may provide a predetermined criterion includes a trend in the average ETCO2 value exceeding a predetermined threshold trend. The medical system may provide a predetermined criterion that includes an averaged ETCO2 value being greater a percentage of a moving average of a plurality of previously measured ETCO2 values. The medical system may provide a predetermined criterion that includes an averaged ETCO2 value being less than a percentage of a moving average of a plurality of previously measured ETCO2 values. The medical system may include a patient monitoring device includes a defibrillator. The medical system may include a patient monitoring device includes an automated external defibrillator or a professional style defibrillator. The medical system may include a user interface that is configured to display visual feedback.

The medical system may provide a visual feedback includes at least one of oxygen saturation, end tidal CO2 (ETCO2), ECG signals from the patient, acoustic information, a transthoracic impedance, blood pressure, body temperature, heart rate, and respiration rate. The medical system may include a display that is a touchscreen display configured to receive input from the rescuer. The medical system may include a patient monitoring device includes one or more inputs for receiving information from the rescuer. The medical system may include inputs include at least one of softkeys, buttons, knobs, touchscreen inputs, and switches. The medical system may include one or more portable computing devices communicatively coupled to the patient monitoring device to transmit and receive patient information from the patient monitoring device. The medical system may include a one or more portable computing devices includes at least one of a tablet computer, smartphone, and laptop. The medical system may include a portable computing device includes a touchscreen display for receiving patient information from the rescuer, the patient information including at least one of a height, a weight, and a gender of the patient.

The medical system may include a portable computing device connects to one or more central facilities to obtain additional patient information about the patient. The medical system may provide a determination of whether the ET tube remains properly placed that is displayed on at least one of the display of the patient monitoring device and the portable computing device. The medical system may include at least one processor that is configured to initiate a timer based on the determined presence of airflow in the patient's airway. The medical system may include at least one processor that is configured to determine whether the ET tube remains properly placed based prior to expiration of the timer. The medical system may include at least one processor that is configured to present the output to the user interface the determination of whether the ET tube remains properly placed prior to the expiration of the timer. The medical system may provide a timer that is a predefined value between 5 and 15 seconds. The medical system may provide a timer that is a user-defined value.

The medical system may provide a determination of whether the ET tube remains properly placed that is based on a correlation between the received physiological information and the determined presence of airflow in the patient's airway. The medical system may include a correlation that includes a confirmation that a positive pressure breath given to the patient has reached the patient's lungs. The medical system may include a positive pressure breath given to the patient results in the determined presence of airflow in the patient's airway. The medical system may include one or more impedance sensors for obtaining a transthoracic impedance of the patient. The medical system may include at least one processor and memory that is configured to receive the transthoracic impedance regarding the airflow in the patient's lungs. The medical system may provide a determined physiological baseline includes an initial transthoracic impedance baseline determined upon initial placement of the ET tube.

The medical system may provide an initial transthoracic impedance baseline that includes an average of a plurality of initial transthoracic impedance values received upon initial placement of the ET tube. The medical system may provide a deviation from the physiological baseline that includes a percentage difference between a current transthoracic impedance value and the initial baseline. The medical system may provide a determined physiological baseline that includes a dynamic transthoracic impedance baseline with continually updated transthoracic impedance values. The medical system may provide a dynamic baseline that includes a moving average of a plurality of transthoracic impedance values received after placement of the ET tube. The medical system may include at least one processor and memory is configured to determine a prior baseline before placement of the ET tube is initiated, and determine whether the ET tube is properly placed based on a deviation from the prior baseline. The medical system may include one or more impedance sensors for obtaining a transthoracic impedance of the patient, wherein the prior baseline is based on the transthoracic impedance of the patient.

An example of a medical system for assisting a rescuer with an intubation procedure for a patient is described. The system may include one or more airflow sensors configured to obtain data indicative of airflow in the patient's airway, one or more impedance sensors for obtaining a transthoracic impedance of the patient, a patient monitoring device communicatively coupled to the one or more airflow sensors and the one or more impedance sensors, the patient monitoring device comprising a user interface comprising a display, and at least one processor and memory configured to receive the data indicative of the airflow in the patient's airway, determine the presence of airflow in the patient's airway based on the received data, receive the transthoracic impedance regarding the airflow in the patient's lungs, determine a physiological baseline regarding airflow in the patient's lungs after initial placement of the ET tube, determine whether the ET tube remains properly placed based on a deviation from the determined physiological baseline, and present to the display of the user interface an output of the determination of whether the ET tube remains properly placed.

Implementations of such a medical system may include one or more of the following features. The medical system may provide a physiological baseline that is an initial baseline determined upon initial placement of the ET tube. The medical system may provide an initial baseline that includes an average of a plurality of initial transthoracic impedance values received upon initial placement of the ET tube. The medical system may provide a deviation from the physiological baseline that includes a percentage difference between a current transthoracic impedance value and the initial baseline. The medical system may provide a physiological baseline that is a dynamic baseline with continually updated transthoracic impedance values. The medical system may provide a dynamic baseline that includes a moving average of a plurality of transthoracic impedance values received after placement of the ET tube.

The medical system may include one or more airflow sensors that include at least one of an oxygen sensor for measuring a concentration of oxygen in the patient's airway, a flow sensor for measuring gas flow rate in the patient's airway, and a capnography sensor for measuring a concentration of $CO_2$ in the patient's airway. The medical system may include a capnography sensor configured to obtain $CO_2$ information regarding airflow in the patient's lungs. The medical system may include at least one processor and memory that is configured to receive the $CO_2$ information regarding the airflow in the patient's lungs. The medical system may provide a determined physiological baseline that includes an initial $ETCO_2$ baseline determined upon initial placement of the ET tube. The medical system may provide an initial $ETCO_2$ baseline that includes an average of a plurality of initial $ETCO_2$ values received upon initial placement of the ET tube. The medical system may provide a deviation from the physiological baseline that includes a percentage difference between a current $ETCO_2$ value and the initial baseline.

The medical system may provide a determined physiological baseline that includes a dynamic $ETCO_2$ baseline with continually updated transthoracic impedance values. The medical system may provide a dynamic baseline that includes a moving average of a plurality of ETCO2 values received after placement of the ET tube.

The medical system may include a patient monitoring device includes a defibrillator. The medical system may include a patient monitoring device includes an automated external defibrillator or a professional style defibrillator. The medical system may include a user interface that is configured to display visual feedback. The medical system may provide a visual feedback includes at least one of oxygen saturation, end tidal CO2 (ETCO2), ECG signals from the patient, acoustic information, a transthoracic impedance, blood pressure, body temperature, heart rate, and respiration rate. The medical system may include a display that is a touchscreen display configured to receive input from the rescuer. The medical system may include a patient monitoring device includes one or more inputs for receiving information from the rescuer. The medical system may include an inputs include at least one of softkeys, buttons, knobs, touchscreen inputs, and switches. The medical system may include one or more portable computing devices communicatively coupled to the patient monitoring device to transmit and receive patient information from the patient monitoring device. The medical system may include a one or more portable computing devices includes at least one of a tablet computer, smartphone, and laptop. The medical system may include a portable computing device includes a touchscreen display for receiving patient information from the rescuer, the patient information including at least one of a height, a weight, and a gender of the patient. The medical system may include a portable computing device connects to one or more central facilities to obtain additional patient information about the patient.

The medical system may provide a determination of whether the ET tube remains properly placed that is displayed on at least one of the display of the patient monitoring device and the portable computing device. The medical system may include at least one processor that is configured to initiate a timer based on the determined presence of airflow in the patient's airway. The medical system may include at least one processor that is configured to determine whether the ET tube remains properly placed based prior to expiration of the timer. The medical system may include at least one processor that is configured to present the output to the user interface the determination of whether the ET tube remains properly placed prior to the expiration of the timer. The medical system may provide a timer that is a predefined value between 5 and 15 seconds. The medical system may provide a timer that is a user-defined value. The medical system may provide a determination of whether the ET tube remains properly placed that is based on a correlation between the received physiological information and the determined presence of airflow in the patient's airway. The medical system may provide a correlation that includes a confirmation that a positive pressure breath given to the patient has reached the patient's lungs. The medical system may provide a positive pressure breath given to the patient resulting in the determined presence of airflow in the patient's airway.

The medical system may include at least one processor and memory configured to determine a prior baseline before placement of the ET tube is initiated, and determine whether the ET tube is properly placed based on a deviation from the prior baseline. The prior baseline may be based on the transthoracic impedance of the patient.

An example of a medical system for assisting a rescuer with an intubation procedure for a patient is described. The system may include one or more airflow sensors configured to obtain data indicative of airflow in the patient's airway, one or more acoustic sensors for obtaining acoustic information from the patient, a patient monitoring device communicatively coupled to the one or more airflow sensors and the one or more acoustic sensors, the patient monitoring device comprising a user interface comprising a display, and at least one processor and memory configured to receive the data indicative of the airflow in the patient's airway, determine the presence of airflow in the patient's airway based on the received data, receive the acoustic information regarding the airflow in the patient's lungs, determine a physiological baseline regarding airflow in the patient's lungs after initial placement of the ET tube, determine whether the ET tube remains properly placed based on a deviation from the determined physiological baseline, and present to the display of the user interface an output of the determination of whether the ET tube remains properly placed.

Implementations of such a medical system may include one or more of the following features. The medical system may provide a physiological baseline that is an initial baseline determined upon initial placement of the ET tube. The medical system may provide an initial baseline that includes an average of a plurality of initial spectral components received upon initial placement of the ET tube. The medical system may provide a deviation from the physiological baseline that includes a percentage difference between a current spectral pattern and the initial baseline. The medical system may provide a physiological baseline that is a dynamic baseline with continually updated spectral pattern. The medical system may provide a dynamic baseline that includes a moving average of a plurality of spectral components received after placement of the ET tube. The medical system may include a one or more airflow sensors includes at least one of an oxygen sensor for measuring a concentration of oxygen in the patient's airway, a flow sensor for measuring gas flow rate in the patient's airway, and a capnography sensor for measuring a concentration of CO2 in the patient's airway. The medical system may include a capnography sensor configured to obtain CO2 information regarding airflow in the patient's lungs. The medical system may include at least one processor and memory that is configured to receive the CO2 information regarding the airflow in the patient's lungs. The medical system may provide a determined physiological baseline that includes an initial ETCO2 baseline determined upon initial placement of the ET tube. The medical system may provide an initial ETCO2 baseline that includes an average of a plurality of initial ETCO2 values received upon initial placement of the ET tube. The medical system may provide a deviation from the physiological baseline that includes a percentage difference between a current ETCO2 value and the initial baseline.

The medical system may provide a determined physiological baseline that includes a dynamic ETCO2 baseline with continually updated transthoracic impedance values. The medical system may provide a dynamic baseline that includes a moving average of a plurality of ETCO2 values received after placement of the ET tube. The medical system may include one or more impedance sensors for obtaining a transthoracic impedance of the patient. The medical system may include at least one processor and memory that is configured to receive the transthoracic impedance regarding the airflow in the patient's lungs. The medical system may provide a determined physiological baseline that includes an initial transthoracic impedance baseline determined upon initial placement of the ET tube. The medical system may provide an initial transthoracic impedance baseline that includes an average of a plurality of initial transthoracic impedance values received upon initial placement of the ET tube. The medical system may provide a deviation from the physiological baseline that includes a percentage difference between a current transthoracic impedance value and the initial baseline. The medical system may provide a determined physiological baseline that includes a dynamic transthoracic impedance baseline with continually updated transthoracic impedance values. The medical system may provide a dynamic baseline that includes a moving average of a plurality of transthoracic impedance values received after placement of the ET tube.

The medical system may include a patient monitoring device that includes a defibrillator. The medical system may include a patient monitoring device includes an automated external defibrillator or a professional style defibrillator. The medical system may include a user interface that is configured to display visual feedback. The medical system may include a visual feedback includes at least one of oxygen saturation, end tidal CO2 (ETCO2), ECG signals from the patient, acoustic information, a transthoracic impedance, blood pressure, body temperature, heart rate, and respiration rate. The medical system may include a display that is a touchscreen display configured to receive input from the rescuer. The medical system may include a patient monitoring device includes one or more inputs for receiving information from the rescuer. The medical system may include an inputs include at least one of softkeys, buttons, knobs, touchscreen inputs, and switches. The medical system may include one or more portable computing devices communicatively coupled to the patient monitoring device to transmit and receive patient information from the patient monitoring device. The medical system may include a one or more portable computing devices includes at least one of a tablet computer, smartphone, and laptop. The medical system may include a portable computing device includes a touchscreen display for receiving patient information from the rescuer, the patient information including at least one of a height, a weight, and a gender of the patient.

The medical system may include a portable computing device that connects to one or more central facilities to obtain additional patient information about the patient. The medical system may provide a determination of whether the ET tube remains properly placed that is displayed on at least one of the display of the patient monitoring device and the portable computing device. The medical system may include at least one processor that is configured to initiate a timer based on the determined presence of airflow in the patient's airway. The medical system may include at least one processor that is configured to determine whether the ET tube remains properly placed based prior to expiration of the timer. The medical system may include at least one processor that is configured to present the output to the user interface the determination of whether the ET tube remains properly placed prior to the expiration of the timer. The medical system may provide a timer that is a predefined value between 5 and 15 seconds. The medical system may provide a timer that is a user-defined value. The medical system may provide a determination of whether the ET tube remains properly placed that is based on a correlation between the received physiological information and the determined presence of airflow in the patient's airway. The medical system may provide a correlation that includes a confirmation that a positive pressure breath given to the patient has reached the patient's lungs. The medical system may provide a positive pressure breath given to the patient that results in the determined presence of airflow in the patient's airway.

The medical system may include at least one processor configured to determine whether the ET tube remains properly placed based prior to expiration of the timer. The medical system may an output to the user interface of a determination of whether the ET tube remains properly placed prior to the expiration of the timer.

An example of a medical system for assisting a rescuer in performing one or more steps of an airway intubation procedure on a patient is described. The system may comprise one or more sensors configured to obtain one or more intubation parameters, and a medical device communicatively coupled to the one or more sensors, the medical device receiving the one or more intubation parameters from the one or more sensors. The system may further comprise a processor of the medical device configured to analyze the obtained intubation parameters from the one or more sensors and identify which step of the airway intubation procedure is being performed on the patient based on values of the one or more intubation parameters. The system includes an output device of the medical device configured to generate feedback based on which of the identified one or more steps of the airway intubation procedure is being performed. Lastly, the processor detects when a different step of the one or more steps of the airway intubation procedure is performed based on the values of the one or more intubation parameters changing, and adjusts the feedback of the output device to correspond to the detected different step being performed. Implementations of such a system may include one or more of the following features.

An example of another for a medical system for assisting a rescuer with a rapid sequence intubation (RSI) procedure is provided. The medical system may include one or more sensors configured to obtain data indicative of one or more intubation parameters (e.g., gas parameter(s), physiological parameter(s), positioning parameter(s), and a patient monitoring device communicatively coupled to the one or more sensors. The patient monitoring device may include a user interface, a memory comprising a plurality of predetermined RSI steps and a plurality of intubation parameter values corresponding to the plurality of predetermined RSI steps, a processor coupled to the memory. The processor may be configured to receive data indicative of one or more intubation parameters, estimate one or more intubation parameter values based on the data, detect a transition from a first RSI step to a second RSI step chosen from the plurality of predetermined RSI steps based on a change in the one or more intubation parameter values, and present to the user interface an output to assist the rescuer in performing the second RSI step. In various embodiments, gas parameters may include one or more of oxygen (O2) concentration, carbon dioxide (CO2) concentration, gas flow rate, inspiratory flow rate, expiratory flow rate, tidal volume, minute volume, airway pressure, gas temperature, and gas humidity. Physiological parameters may include one or more of oxygen saturation, end-tidal CO2, pulse oximetry, near infrared spectroscopy, transthoracic impedance, ECG, acoustic information, and blood pressure. Positioning parameters may include one or more of motion information, displacement, position information, velocity, acceleration, video information, and image information. The medical system may comprise a defibrillator. The medical system may require the rescuers to verify the detected different step manually prior to the output device adjusting the feedback. The one or more sensors may comprise a pulse oximeter configured to acquire oxygen saturation information from the patient. The output device is configured to initiate an alarm if the oxygen saturation information indicates that the patient is experiencing hypoxemia. The output device may further be configured to initiate an alarm if the oxygen saturation information falls below a predetermined threshold. The predetermined threshold may be based on at least one of an age, height, weight, and gender of the patient. The one or more sensors may comprise a motion sensor configured to acquire motion signals indicative of progress of the rescuer in performing the airway intubation procedure.

The system may comprise electrocardiogram leads to acquire heart beat information of the patient. The one or more sensors may comprise a capnography sensor configured to acquire end-tidal CO2 (ETCO2) information from an airway of the patient. The one or more sensors may comprise an oxygen sensor configured to acquire oxygen delivery parameters from the airway of the patient. The one or more sensors may comprise a flow sensor configured to acquire flow rate parameters from an airway of the patient. The one or more sensors may be integrated within an airway sensor module configured to be positioned in the airway of the patient. The airway sensor(s) may be configured to be coupled with a bag-valve mask for performing manual ventilations on the patient.

The medical system may provide parameters of the patient that include oxygen saturation, expired carbon dioxide levels, and end tidal carbon dioxide (ETCO2). The processor may be configured to automatically determine whether preoxygenation has begun based on the changes in values of the intubation parameters. The one or more intubation parameters may comprise at least one of an amount of oxygen detected by an oxygen sensor placed in an airway of the patient, and a flow rate of gas in the airway of the patient. The processor is configured to automatically initiate a preoxygenation timer in response to a start of a preoxygenation step of the airway intubation procedure for guiding the rescuer in providing an adequate amount of oxygen to the patient. The feedback generated by the output device may comprise an indication that the preoxygenation timer has expired. The processor may further be configured to automatically initiate a procedure timer in response to a start of an intubation step of the airway intubation procedure. The feedback generated by the output device may comprise an indication that procedure timer has expired. The output device is a display for displaying visual feedback. The display is a touchscreen display configured to receive input from the rescuer.

The medical system further comprising a wrist-worn device that provides at least of visual and audible feedback to the rescuer. The wrist worn device may comprise an accelerometer that detects motion of the rescuer. The medical system may comprise near-field communication transceivers on the airflow sensor module and an ET tube to determine proximity of airflow sensor module and the ET tube. The processor is configured to automatically calculate drug dosage information of the patient in response to user entered information. The output device is configured to display the drug dosage information.

The processor may be configured to automatically generate and store in memory event marker information in response to actions being performed by the rescuer. The output device may be configured to generate tones coordinated with determined QRS complexes of the patient. The output device may be configured to generate the tones in response to a determination of a start of endotracheal tube placement in the patient. The frequency of each tone is based on a detected oxygen saturation level. The processor is configured to automatically verify an initiation of tube placement based on the one or more intubation parameters. The one or more intubation parameters comprises a characteristic of airflow in the airway of the patient. The characteristic of airflow comprises at least one of flow rate in the airway of the patient, ETCO2, and an amount of oxygen in the airway of the patient. The processor may be configured to start a procedure timer upon verification of the initiation of tube placement. The feedback generated by the output device comprises a display of the procedure timer. The feedback generated by the output device comprises a display of oxygen saturation information of the patient. The processor may be configured to automatically verify tube placement based on the one or more intubation parameters.

The processor may be configured to automatically verify that the patient is in proper position prior to tube placement and the output device is configured to provide feedback to the rescuers to move the patient to a proper position if the patient is not in a correct position for intubation.

In another example, a medical device for assisting a rescuer in performing one or more steps of an airway intubation procedure on a patient is described. The system may comprise an oxygen sensor configured to be positioned in a path of the patient's airway and to acquire one or more oxygen delivery parameters, a capnography sensor configured to be positioned in the path of the patient's airway and to acquire ETCO2 of the patient. The system may include a flow sensor configured to be positioned in the path of the patient's airway and to acquire a flow rate in the patient's airway, at least one processor commutatively coupled to the oxygen sensors and capnography sensor and configured to, analyze the one or more oxygen delivery parameters from the oxygen sensors, the capnography sensor, and the flow sensor, to determine whether the patient is being properly ventilated based on at least one of a detected amount of oxygen in the patient's airway, the measured ETCO2 of the patient, and the flow rate in the patient's airway; and an output device including a visual display and configured to display feedback to the rescuers based on the acquired information indicative of the amount of oxygen in the patient's airway, ETCO2, and the flow rate in the patient's airway. Implementations of such a device may include one or more of the following features.

The oxygen sensor, the capnography sensor and the flow sensor may be generally provided as separate components though, in certain embodiments, may be incorporated in an integrated airway sensor module. The processor may be configured to determine whether preoxygenation has been initiated based on at least one of the amount of oxygen in the patient's airway and the flow rate in the patient's airway. In some embodiments, the processor may be configured to begin a preoxygenation timer based on the determination of whether preoxygenation has been initiated. The feedback on the output device comprises visual display of at least one of the preoxygenation timer and an indicator of oxygen reserve (e.g., oxygen reserve index which provides an indication of the fullness of oxygen capacity of the patient). The processor may be configured to determine whether an intubation process has been initiated based on a change in at least one of an amount of oxygen in the patient's airway and flow rate in patient's airway. The change in the amount of oxygen comprises a lack of change in oxygen concentration detected in the airway sensor. The change in the flow rate comprises a lack of flow detected in the airway sensor. The processor may be configured to begin procedure timer based on the determination of whether the intubation process has been initiated. The feedback on the output device Implementations of such a patient support structure may include one or more of the following features.

An oxygen saturation sensor may be to acquire information indicative of oxygen saturation levels of the patient. The oxygen saturation sensor comprises at least one of pulse oximeter and a near infrared tissue oxygen sensor. The feedback of the output device comprises visual display of the oxygen saturation level of the patient. The feedback of the output device may be include an indication of whether the oxygen saturation level of the patient has met criteria for determining that the patient is at risk of being hypoxemic. The criteria for determining that the patient is at risk of being hypoxemic may comprise a determination that the oxygen saturation level of the patient has dropped below a predetermined threshold during intubation of the patient.

The processor may be configured to determine whether an intubation process has been completed successfully based on a change in at least one of flow rate in patient's airway, ETCO2 and change between the inspired and expired oxygen concentration. The feedback of the output device comprises visual display of at least one of the oxygen saturation level of the patient and ETCO2. The output device may comprise an indication of whether the oxygen saturation level of the patient has met criteria for determining that the patient is at risk of being hypoxemic. The criteria for determining that the patient is at risk of being hypoxemic may comprise a determination that the oxygen saturation level of the patient has dropped below a predetermined threshold during monitoring of the patient. Feedback of the output device of the ETCO2 and air flow may comprise an indication of whether adequate ventilation is being performed for determining if the patient is at risk hypercarbia with the criteria determined based on predetermined values for these values based on clinical norms and patient information anthropometric data.

Various aspects of examples of the system are set out in the claims. According to a first aspect of the present system, a ventilation monitoring device comprises at least one processor and at least one memory including computer program code. The at least one memory and the computer program code are configured with at least one processor to cause the ventilation monitoring device to determine whether an intubated subject's tracheal tube is properly placed by receiving an indication of a subject's breathing from at least one sensor.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1A:
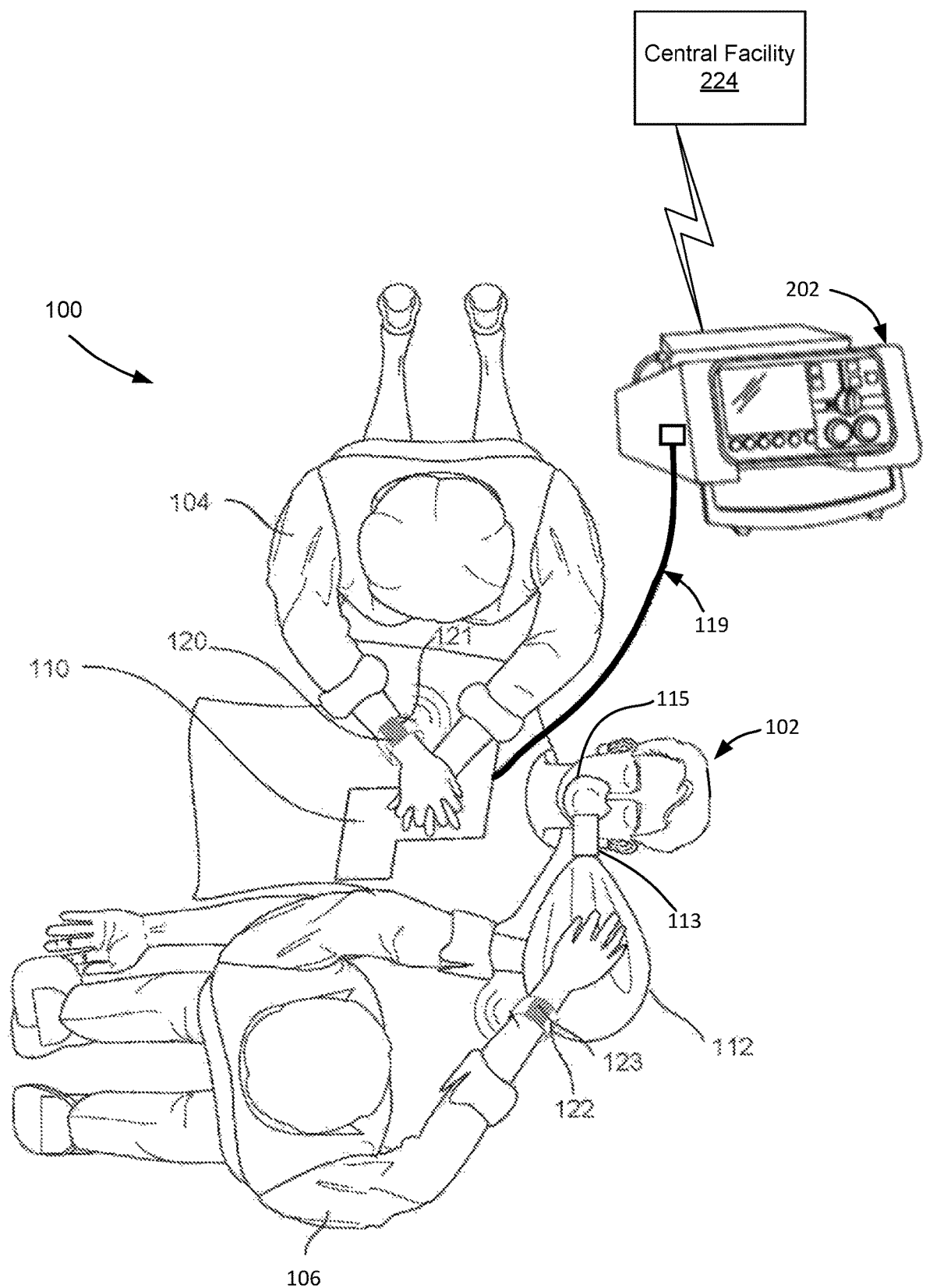
FIG. 1A is a schematic illustration of an example of a medical system, including a medical device, electrode assembly, and rescuers providing medical treatment to a patient prior to intubation.

Rapid sequence induction (or intubation) is intended to be an effective procedure for rapid placement of the endotracheal tube in a patient. Successful RSI implementation often uses the mnemonic "The 7 P's of RSI" to help rescuers remember each of the steps involved in the procedure. The 7 "Ps" include Preparation, Preoxygenation, Pretreatment, Paralysis with induction, Protection and Positioning, Placement with Proof, and Post-intubation management. While some rescuers (or caregivers) may have extensive experience performing intubation, other rescuers, may have limited experience with the procedure and might not remember the exact order of steps or all actions required to ensure a successful outcome.

Intubation is a time-sensitive procedure that can be quite dangerous and, thus, requires careful attention by the rescuer. The present system is designed to optimize or otherwise enhance the rescuer's performance and the patient's safety during the procedure. In general, the present system is related to a medical airway management system that is designed to aid clinicians during intubation procedures, such as the rapid sequence intubation procedure, as discussed in further detail herein, amongst others. An advantage of the present system is that the system provides automated guidance and context-sensitive feedback throughout the steps of procedure. The system uses a variety of sensors to automatically detect which steps are being performed, at any given time, and also identify when the rescuers have started a new step. For instance, and will be described in more detail below, medical devices (e.g., patient monitoring devices) for use in medical airway management systems in accordance with embodiments discussed may implement one or more sensors for obtaining data indicative of one or more intubation parameters, where the intubation parameter(s) may be used by the airway management system to detect transition between steps in the RSI procedure, or similar intubation procedure, based on changes in the intubation parameter value(s). The airway management system may also present on a user interface an output to assist the rescuer in performing the various steps of RSI, or similar intubation procedure involving some or all of the steps related to RSI.

As noted above, one or more sensors may be used to obtain information for one or more processors of the airway management system to estimate one or more intubation parameters relevant to the RSI procedure, or another similar intubation/airway procedure. The intubation parameter(s) may include one or more gas parameters, one or more physiological parameters, one or more positioning parameters, and/or other relevant parameters.

In accordance with various embodiments, one or more gas parameters may be used as intubation parameters employed by a patient monitoring device or other airway management system to assist a rescuer through the RSI procedure, or another similar intubation/airway procedure (e.g., more limited intubation procedure). The gas parameter(s) may include, for example, oxygen ($O_2$) concentration in the patient airway, carbon dioxide ($CO_2$) concentration in the patient airway, gas flow rate, inspiratory flow rate, expiratory flow rate, tidal volume, minute volume, airway pressure, gas temperature, gas humidity, or other gas parameters characteristic of the patient airway, e.g., to determine which steps in the overall procedure are being performed. Examples of sensors that may be used to detect the gas parameter(s) may include an oxygen sensor for measuring a concentration of oxygen in the patient's airway, a flow sensor for measuring gas flow rate in the patient's airway, a capnography sensor for measuring a concentration of CO2 in the patient's airway, and/or other sensors configured to obtain information regarding the patient airway and respiratory function. Such sensors may be used alone or in combination with other sensors, or sensor types, for the medical system to provide context-sensitive prompting or information for the rescuer.

In certain embodiments, physiological parameters may also be measured and used as input for the airway management system as intubation parameters to determine which steps in the RSI procedure or other intubation procedure are being performed. Examples of such physiological sensors include a pulse oximeter to measure oxygen saturation (SpO2) and a capnography sensor to measure expiratory CO2, typically presented as a waveform of expiratory CO2 vs. time (ETCO2). Other examples of physiological sensors that may be used in accordance with embodiments of the present disclosure include ECG sensors for obtaining ECG signals from the patient, a microphone for obtaining acoustic information from the patient, impedance sensors for obtaining a transthoracic impedance of the patient (e.g., ECG sensors and/or electrodes for administering electrical therapy may be used for obtaining transthoracic impedance or images based on impedance), and noninvasive blood pressure sensors for obtaining blood pressure of the patient. The amplitude, rate, trend, and shape of the waveform will change based on changes in the patient's condition.

In various embodiments of the present disclosure, positioning parameters may be used as intubation parameters in a patient monitoring device or other airway management system to help a rescuer properly navigate through the RSI procedure, or another intubation procedure. The positioning parameter(s) may provide information having to do with the relative positions of the patient, rescuer, and/or equipment used in the procedure. Various positioning parameters may include, for example, motion information, displacement, position information, velocity, acceleration, video information, and image information. Image information may be captured, for example, by a camera located on or near a patient monitoring device, or a laryngoscope used in conjunction with the RSI procedure where the video thereof is presented on the patient monitoring device or other display of the airway management system.

A benefit of the automated detection of which steps in the procedure are being performed alleviates rescuers from having to manually adjust display settings during the procedure or otherwise be distracted from the task at hand in treating the patient. Accordingly, embodiments of the present disclosure are useful to increase the likelihood that the rescuers' focus remains on treating the patient throughout the procedure while also helping the rescuers' carry out each of the necessary steps. In some cases, the airway management system prioritizes certain intubation parameters to be displayed or otherwise communicated to the rescuer(s) so that the most relevant information is readily accessible.

Thus, for example, when the patient is being manually ventilated during preoxygenation, an oxygen sensor for detecting the concentration of oxygen in the patient's airway as a gas parameter may be used to detect that oxygen is being administered to the patient. This oxygen detection (e.g., confirmed by exceeding a preset threshold) may act as a trigger for the airway management system to determine that preoxygenation is occurring. During preoxygenation, a patient monitoring device of the airway management system may display a trend of the patient's oxygen saturation (e.g., recorded via pulse oximetry, near infrared spectroscopy, or another suitable method) or oxygen reserve indicator or index (discussed further below). If appropriately preoxygenated, the patient's oxygen saturation levels may be at or near 100%. Then, during tube placement when manual ventilation is halted for the time being, the oxygen saturation waveform is likely to change shape over time. For example, during tube placement, as the body takes up oxygen from the oxygen reservoir in the lungs, oxygen saturation will gradually decrease to the point of more substantial desaturation. Further, during intubation placement, certain intubation gas parameters (e.g., air flow and/or CO2 as detected by the airway and/or CO2 sensor(s)) may no longer be present or detectable. The lack of other physiological parameters (e.g., ETCO2 or CO2 waveform as estimated from data collected from a capnography sensor) may also be indicative intubation parameters. Also, other physiological parameters, such as lung sounds (as detected by a microphone or acoustic sensor positioned on the patient) and chest rise based on impedance detection (from electrode sensors placed on the patient) will also no longer be present. This change in waveform can be used, along with other information discussed in the specification below, to determine when a next step has started.

In response to that detected new step, as discussed herein, the airway management system changes which intubation parameters are displayed on the patient monitoring device to the rescuers. This ensures the rescuers are presented with the most relevant information at each point during the entire case to carry out an effective procedure, without requiring rescuers from having to manually adjust display settings during the procedure, and helps to ensure that the rescuers' focus remains on treating the patient throughout the procedure.

Additionally, the patient monitoring device of the airway management system may be further configured to automatically verify that the tube placement procedure was successful and/or continue to verify that proper tube placement is maintained. One common mode of failure during intubation occurs when the rescuer inserts the endotracheal tube into the patient's esophagus (i.e., the pathway to the stomach). Compounding that mistake, rescuers may then fail to continue monitoring of the patient (e.g., inspecting the CO2 waveform) to verify whether the tube was placed correctly and is appropriately delivering oxygen to the patient and ensure that the intubation tube does not become dislodged after placement. One benefit of the present disclosure is that the system not only analyzes intubation parameters to determine when steps are being performed, but the system also verifies that the measured signals are consistent with successful tube placement (on initial placement and also to confirm that the tube remains properly placed during post-intubation monitoring) and that the patient is able to remain hemodynamically stable during and after the procedure. After the tube is placed and the patient is being monitored, the system may continue to verify that the tube is properly placed. For example, the system may employ a flow sensor to detect airflow in the patient airway (e.g., airflow from the ventilation apparatus such as bag-valve mask, ventilator, etc.) and then initiate a timer to receive physiological information that confirms that the ventilation airflow has reached the patient's lungs (as opposed to the esophagus) within the specified time interval. Such physiological information may be obtained, for example, from a capnography (CO2) sensor, impedance detection via electrode pads, an acoustic sensor that is able to detect the sound of air entering the patient's lungs, and/or another appropriate manner. In the event they are not, context-sensitive alarms alert the user and provide a prioritized list of clinical actions required to safely manage the patient.

In various embodiments of the present disclosure, one or more components of the airway management system may include one or more airway sensors for measuring data indicative of gas parameters characteristic of gas flowing or otherwise present in the patient airway. As discussed, signals measured by the airway sensor(s) during both inspiration and expiration may include one or more of the following gas parameters: oxygen (O2) concentration, carbon dioxide (CO2) concentration, gas flow rate, inspiratory flow rate, expiratory flow rate, tidal volume, minute volume, airway pressure, gas temperature, gas humidity, etc. The one or more airway sensors may be coupled to a patient monitoring device such that, while the patient is being monitored, the data from the sensors is continuously communicated to the patient monitoring device. The patient monitoring device comprises one or more processors configured to continuously receive the data indicative of gas parameters and process the data to generate values. In certain embodiments, in addition to the sensor(s) and processor(s) for measuring gas parameters, processing resources (e.g., in the, patient monitoring device, sensor(s) themselves, or other medical device) are able to calculate additional measurement parameters that may include: breath volume, breathing rate, O2 consumption, CO2 elimination rate, respiratory quotient, airway leak and other calculated values. In addition, the airway management system (e.g., one or more processors incorporated in a patient monitoring device) are configured to perform detailed signal waveform analysis to identify clinically significant patterns indicative of physiologic or airway gas measurement conditions and/or system/sensor faults that require user attention or intervention.

In certain embodiments, one or more airway sensors may be incorporated in a more integrated airway sensor module provided with the manual ventilation device (e.g., bag-valve mask). One benefit of such an arrangement is that rescuers may fail to place, e.g., the CO2 sensor (capnography sensor) or are delayed in placing it. By having certain sensors integrated into a single manual ventilation device (e.g., bag-valve mask) that engages with the patient, the airway management system will monitor multiple intubation parameters such as CO2, O2, and flow rates and pressure anytime a ventilation bag is used. However, it should be understood that various sensors may be positioned at different locations on or near the patient. For example, an oxygen sensor, a capnography sensor and/or a flow sensor may be placed in the patient airway or at side stream locations of the patient airway for obtaining information to estimate relevant gas parameters characteristic of the patient airway.

Medical System Overview

FIG. 1A is a schematic illustration of an example of an airway management system 100, including a medical device 202 (e.g., patient monitoring device such as an automated external defibrillator or professional style monitor/defibrillator), electrode assembly 110, and rescuers 104, 106 providing medical treatment to a patient 102 prior to intubation. While several embodiments presented herein describe the medical device 202 as implementing the processor(s) for analyzing data from the sensor(s), determining next steps in the RSI procedure, and providing output via a user interface, it can be appreciated that other portable computing devices such as a tablet or other computing device may perform steps in accordance with the present disclosure. Additionally, the portable computing devices may be used in conjunction with medical device 202.

In this example, rescuers 104, 106 are in position and providing care to the patient 102, with rescuer 104 providing chest compressions to the torso of the patient 102, and rescuer 106 providing ventilation using ventilation bag 112, which is connected to a ventilation valve 113 and a mask 115. Collectively, these components (112, 113, 115) are often referred to as a bag-valve-mask or (BVM). While not illustrated, the BVM is often connected to a source of "medical oxygen," which is used as an oxygen supply to the bag 112, so that oxygen can be delivered during ventilation.

Generally, the rescuers 104, 106 may be lay-rescuers who were near the patient 102 when the patient required care, or may be trained medical personnel such as doctors, firefighters, paramedics, combat medics, or emergency medical technicians, for example. Although two rescuers 104, 106 are illustrated, in alternative embodiments additional rescuers (not shown) may also be involved in treating the patient or only one rescuer may provide treatment. As used hereinafter, the term rescuer may generally be understood to include a person that is aiding in acute care treatment of the patient 102 during an emergency medical situation, and may be actively engaged in resuscitation activity of the patient, such as in providing cardiopulmonary resuscitation. Additionally, similar terms such as clinician, user, or caregiver are generally understood to be interchangeable when used herein to describe a person giving acute medical and/or resuscitative aid to the patient.

Additionally, while the present system is described with respect to a BVM and manual ventilations, a portable automatic ventilator could be used to provide oxygen and ventilate the patient. The EMV+® or Z Vent™, both manufactured by ZOLL Medical Corporation of Chelmsford, MA are examples of portable ventilators. Likewise, the rescue scenario may occur in a hospital or ambulance where an automatic ventilator may also be available (e.g., ZOLL 731 Ventilators provided by ZOLL® Medical Corporation).

Control and coordination for the medical event is typically controlled by the medical device 202. In a typical implementation, the medical device 202 is a defibrillator, automated external defibrillator (AED), ventilator system, or medical patient monitor, to list a few examples. Alternatively, the medical device 202 could even be mobile computing device such as a tablet-based computer, smartphone, or wearable computing and interface device (e.g., smart watch or head mounted optical display) that is controlled by the rescuers 104, 106, for example, in coordinating resuscitation activities, evaluating or otherwise communicating with on-site and/or remote medical personnel, or otherwise providing information useful for the rescuer(s) in treating the patient.

The medical device 202 is connected to an electrode assembly 110 via a wired connection 119 from the medical device to the electrode assembly 110. In this implementation, the medical device (e.g., defibrillator, or patient monitor) may take a generally common form, and may be a professional style defibrillator which may also function as a medical monitor, such as the R-SERIES®, X-SERIES®, M-SERIES®, or E-SERIES® provided by ZOLL® Medical Corporation of Chelmsford, Mass., a ventilator (e.g., portable ventilator), such as the 731 Ventilator provided by ZOLL Medical Corporation, or an automated external defibrillator (AED), such as the AED PLUS®, or AED PRO® provided by ZOLL Medical Corporation.

In addition, the medical device 202 could take the form of an integrated system of devices (defibrillator, vital signs monitor, ventilator, or mechanical CPR chest compression device, for example) with either a composite, single-system embodiment or one that uses a series of discrete devices that are dynamically integrated through wired and/or wireless communication to function as a single integrated system.

This optionally wired connection 119 enables data from sensors in the electrode assembly to transmit information to the medical device 202, and the wired connection 119 also allows energy to be sent from the medical device 202 to the electrode assembly 110, in scenarios in which the medical device is a defibrillator or automated external defibrillator. In alternative embodiments, for example, in scenarios in which the medical device is a tablet or monitor, the wired connection may be replaced with a wireless connection. While not expressly shown in the figures, the BVM component(s) as well as other treatment and/or sensing devices (e.g., oxygen saturation sensors, accelerometers, air flow sensors) may also be communicatively coupled with the medical device 202. For example, in embodiments where the BVM incorporates sensors (e.g., oxygen sensor, capnography, flow sensor, air flow module), such sensors may be in communication with the more central medical device 202. As noted herein, sensors for obtaining data relevant to gas parameters characteristic of the patient airway may be provided as separate components, or may be integrated together into a single component.

The electrode assembly 110 is shown on the patient 102 in a typical position. The electrode assembly 110, in this example, is an assembly that combines an electrode positioned high on the right side of the patient's torso, a separate electrode positioned low on the left side of the patient's torso, and a sensor package located over the patient's sternum. The electrode assembly 110 may further include a sensor package, which, in this example, is obscured in the figure by the hands of rescuer 104. This sensor package may include a motion sensor (e.g., accelerometer(s), velocity sensor, distance sensor) or similar sensor package that may be used in cooperation with a computer in the medical device 202 to monitor performance (e.g., compression depth, compression rate, and release) of the chest compressions, patient movement or positioning. Additionally, a microphone may also be included with, or separately from, the electrode assembly 110 to obtain auscultation data (e.g., acoustic signals) of internal sounds of the patient 102. The microphone may be used to obtain signals related to heart sounds, breathing sounds or gastric sounds, for example.

In the illustrated example, the medical device 202 communicates wirelessly with the wrist-worn devices 120, 122 to present information and/or guidance to the rescuers 104,106. For example, information related to chest compressions, heart rate, or other relevant information (e.g., SpO2, ETCO2) related to the intubation process can be visually presented on the displays 121, 123. Additionally, vibration components and/or audible sound generators on the wrist-worn devices 120, 122 can provide feedback. Such feedback, as discussed more fully below, may include information about physical status of the patient 102, guidance and feedback related to ventilation or cardio pulmonary resuscitations of the patient 102, and/or specific context-sensitive or prioritized instructions to perform critical interventions/ tasks to ensure patient safety or optimal therapeutic management. Haptic and audible feedback may have the added benefit of providing a notification to the rescuer while not requiring the rescuer to divert his/her attention from the task at hand. This is as opposed to a visual display, which would typically require the rescuer to turn his/her head to view whatever is presented on the visual display.

The wrist-worn devices 120, 122 can be smart watches (e.g., computerized wristwatches with functionality enhanced beyond timekeeping) or other wrist worn wearable technology, such as fitness trackers. Such a smart watch can effectively be a wearable computer. The smart watch can include a data processor, memory, input and output. The wrist-worn devices 120, 122 may be equipped to collect information gathered from internal sensors (e.g., an accelerometer, hear rate monitor, pulse oximetry sensor, or colorimeter, to list a few examples), via direct communication therewith or through a separate medium (e.g., defibrillator, monitor, external computer). The smartwatches may also be able to control or retrieve data from each other, other instruments or portable computing devices 225 (shown in FIG. 2), or the medical device 202. Typically, the smartwatch can support wireless technologies, like Bluetooth, 3G/4G cellular network, and/or Wi-Fi, to communicate with the medical device 202 or the other computing device. In other examples, the smartwatch may just serve as a front end for a remote system and be configured to display information generated by the medical device 202. The displays 121, 123 in the wrist-worn devices 120, 122 can be made of Indium gallium zinc oxide (IGZO), a semiconducting material. IGZO thin-film transistors (TFT) can be used in the TFT backplane of flat-panel displays (FPDs). Because the IGZO display is flexible, a greater amount of information can be displayed on the wrist-worn devices 120, 122 due to the increased surface area of the display. Additionally, the display of the wrist-worn devices may be touchscreen displays, which enables user control, selections, and input via interaction with the display. Alternative embodiments may use other display technology, such as flexible organic light emitting diodes (flexible OLED).

In still yet another embodiment, the rescuers may use head-mounted heads-up display systems (not shown). The benefit of wearable heads-up devices is that they allow focus to remain on the patient 102 while at the same time providing a continuous interface to relevant data.

Figure 1B:
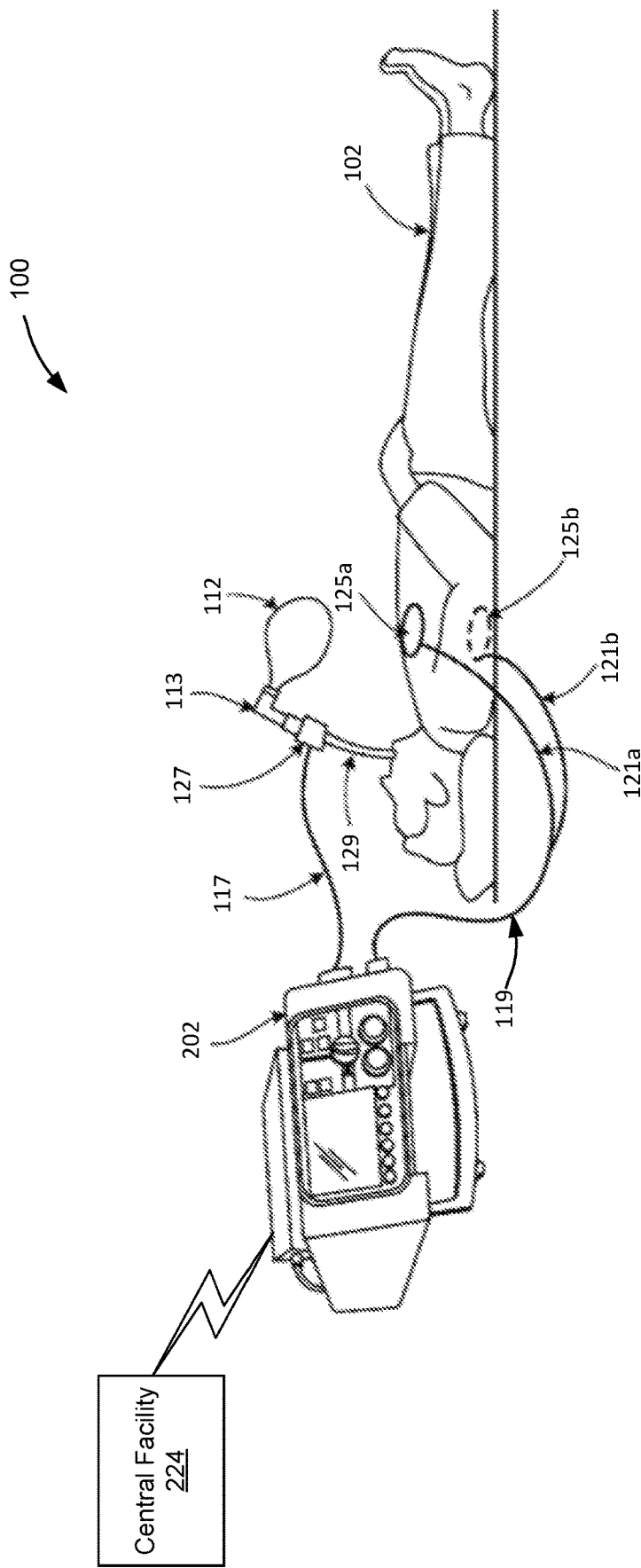
FIG. 1B is a schematic illustration of an example of a medical system, including the medical device, electrodes, and endotracheal tube post intubation in accordance with an embodiment.

FIG. 1B is a schematic illustration of an example of the airway management system 100, including the medical device 202, electrodes, and endotracheal tube 129 post intubation. That is, during post-intubation, the ET tube has been placed in the trachea of the patient and the patient is being physiologically monitored while ventilations are administered (e.g., by a BVM or ventilator).

In general, a tracheal tube is a catheter that is inserted into the trachea of patient 102 to establish and maintain an open airway and to ensure adequate exchange of oxygen and carbon dioxide. An endotracheal tube, such as the endotracheal tube 129, is a specific type of tracheal tube that is usually inserted through the patient's mouth or nose. Many airway tubes such as an endotracheal tube 129 may be used with embodiments of the present device to provide a patient airway for ventilation and monitoring.

The ventilation bag 112 is coupled to the ventilation valve 113. As shown in this example, the mask is no longer required once the endotracheal tube is inserted into the patient. In accordance with embodiments of the present disclosure, one or more airway sensors 127 (e.g., may include one or more of oxygen sensor, capnography sensor, flow sensor, etc.) may be situated between the ventilation bag 112 and the endotracheal tube 129 to allow monitoring of the inspiratory and expiratory gas, for example, as a result of manual ventilation performed using the ventilation bag 112, and/or monitoring of patient breathing. As is typical, the ventilation bag 112 and valve 113 allow the rescuer to actively ventilate the patient 102 by squeezing the bag or for the patient to spontaneously breathe, while in both instances the patient's exhaled gas exits back through the valve allowing for bidirectional monitoring. Alternatively, the ventilation bag 112, may be augmented to provide supplemental O2 from a separate O2 source (e.g., oxygen tank).

In the illustrated embodiment, the airway sensor(s) 127 includes one or more sensors to measure various physiologic and/or airway gas measurement signals during both inspiration and expiration that includes: oxygen (O2), carbon dioxide (CO2), gas flow rate and volume, airway pressure, gas temperature, and gas humidity, to list a few examples. Additionally, processing resources in either the airway sensor(s) 127 or medical device 202 are able to calculate additional physiologic and/or airway gas measurement parameters such as breath volume, breathing rate, O2 consumption, CO2 elimination rate, respiratory quotient, airway leak and other calculated values, for instance.

Communication cable 117 may be any type of communication cable or set of wires, which allows data exchange between the medical device 202 and the airway sensor(s) 127 such as but not limited to an RS-232 cable, Universal Serial Bus (USB) cable or Ethernet cable. Communication between the medical device 202 and the airway sensor(s) 127 could also be wireless communication such as IEEE 802.11 wireless local area network (WLAN) or low-power radio frequency (RF) communication such as Bluetooth, to list a few examples.

Electrodes 125a and 125b are electrically coupled to the medical device 202 using cables 121a and 121b. Electrodes 125a and 125b are positioned across the subject's thoracic cavity and attached to the subject, one electrode anterior and the other electrode posterior to the patient, for example. In the embodiment, electrodes 125a and 125b are capable of measuring an electrocardiogram (ECG) signal from the patient. The electrodes 125a and 125b may also be suitable electrodes for measuring a transthoracic impedance of a subject. In some embodiments, the electrodes 125a, 125b may be high-voltage electrodes capable of transmitting electrotherapy to the patient, such as for electrical defibrillation and/or cardiac pacing treatment.

The medical device 202 is configured with electrodes 125a and 125b that are capable of providing therapeutic shocks, if needed, as well as to monitor changes in the transthoracic impedance of the patient 102. If the endotracheal tube 129 is properly placed in the subject's trachea and the subject's lungs are ventilated using a ventilation bag 112 and valve 113 (or via a mechanical ventilator), then the medical device 202 detects a change in impedance across the subject's thorax between electrodes 125a and 125b. If the endotracheal tube 129 is not properly placed; for example, it was placed in the subject's esophagus, or has become dislodged, the medical device 202 will detect that the impedance change across the subject's thorax does not indicate that effective ventilation is being administered, and may alert the user with a context-sensitive alarm message using audible and/or visual alarm indicators on the medical device 202. Alternatively, or in addition, a capnography sensor is provided in the patient airway (e.g., mainstream or sidestream). In this embodiment, if the endotracheal tube 129 is properly placed in the subject's trachea, then the medical device 202 detects CO2 (e.g., end tidal CO2 or ETCO2) indicative of proper tube placement; and if the endotracheal tube 129 is not properly placed or has become dislodged, the medical device 202 will fail to detect CO2 waveform indicative of proper intubation, and may alert the user with a context-sensitive alarm message using audible and/or visual alarm indicators on the medical device 202. The medical device 202 may be in communication with other devices, such as wrist-worn devices 120, 121, heads up display devices, for example, for alerting the necessary caregiver(s).

Figure 2:
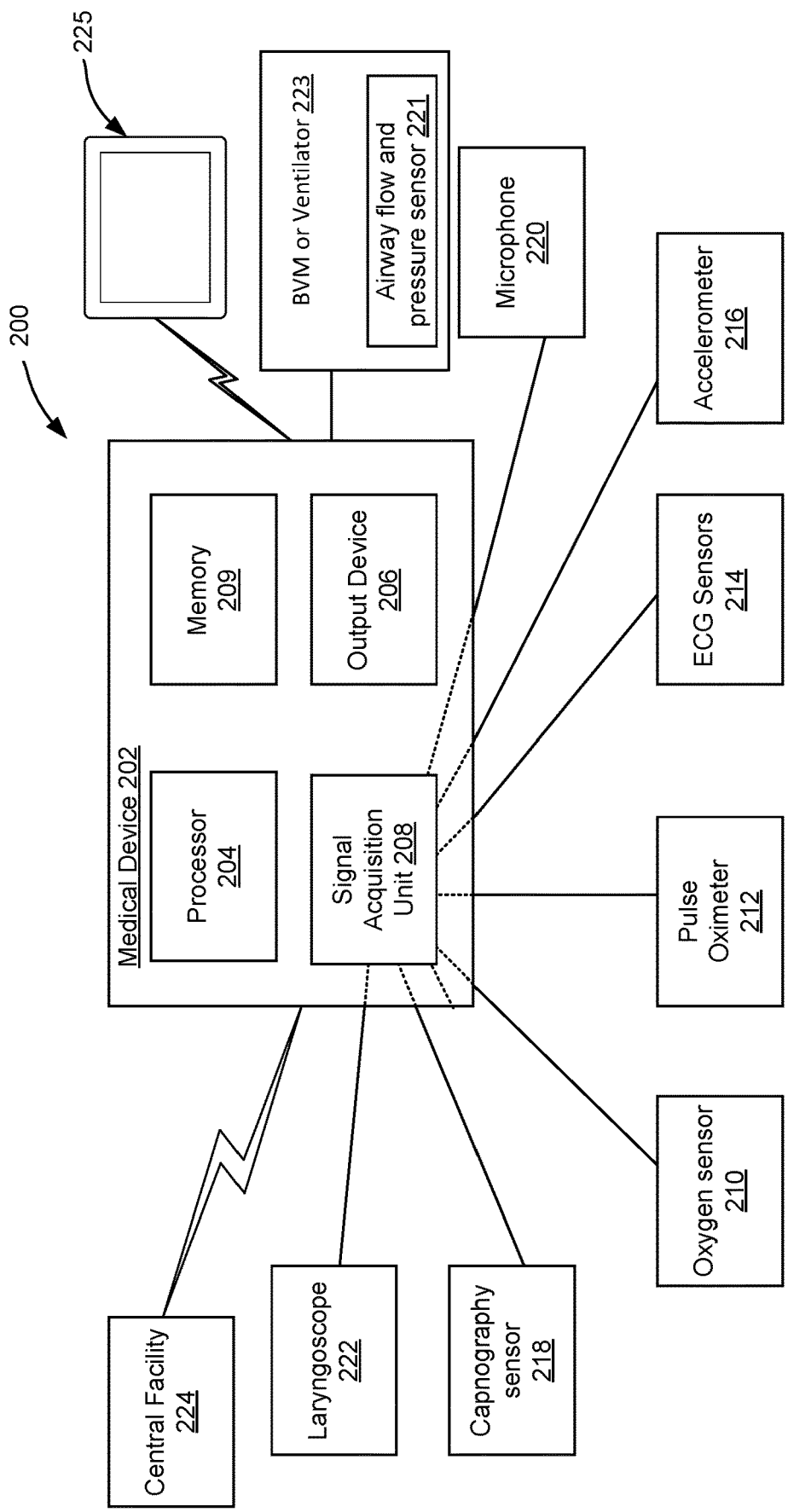
FIG. 2 is a block diagram of the medical system including components of a medical device, a plurality of sensors capable of communicating with the medical device, and a central facility in accordance with an embodiment.

FIG. 2 is a block diagram of the airway management system 200, including the medical device 202, airway sensor(s) 127, device sensors 210-222, which measure intubation parameters, peripherals (e.g., ventilator 223 and portable computing device 225), and a central facility 224. The medical device 202 typically includes a processor 204 for executing instructions of software running on the medical device 202, memory 209 to store the software and sensor information received from the sensors, a signal acquisition unit 208 to receive sensor information from the sensors 210-222, and an output device 206 to provide feedback to the rescuers, which is typically a display. The output device 206 may further include one or more speakers for providing audible feedback, or other components for providing other types of feedback, such as haptic/tactile. Generally, a suitable display can be made from a wide variety of materials as described above. Additionally, the screen may be touchscreen display, which is a combined input/output device, which enables user interaction of the medical device 202 by touching the output device 206.

Additionally or alternatively, the airway management system 200 may further include a portable computing device 225 (e.g., tablet, smartphone, laptop computer) in communication with the medical device 202. In one example, the portable computing device 225 may mirror the display of the medical device 202, or may provide a secondary display of information relevant to the user of the portable computing device 225. For instance, in certain situations, the activities of different users at the emergency scene may differ, hence, it may be preferable for each of the displays (e.g., on the medical device, on the portable computing device, on another device, etc.) to differ according to the job performed by the associated user. Additionally, the portable computing device 225 may include general information (e.g., dosage charts), medical procedure checklists, and/or other protocols that are typically used during an intubation procedure. Additionally, it may include additional checklists and/or protocols for other medical situations (e.g., instructions on the performance of CPR, or instructions on how to assemble the BVM, how to hook the patient up the ventilator, etc.) . . . ). Additionally, the portable computing device would provide a quality assurance report that includes: a list of completed and uncompleted tasks, the time tasks where completed, the required time for each tasks, event markers, alarms that occurred, relevant physiologic data as well as other data that demonstrates the performance of the procedure.

Additionally, the portable computing device 225 may include the ability to allow the user to enter patient information (e.g., height, weight, and gender) via a touchscreen display. The portable computing device may also include internet connectivity (e.g., via Wi-Fi or 3G/4G wireless mobile telecommunication networks) to enable the rescuer to access additional patient information from the central facility, for example.

Respiratory gas monitoring provides a noninvasive method to monitor a range of physiologic or airway gas measurement data that indicates the pattern of ventilation, its effectiveness, the patient's metabolic state, endotracheal tube placement and cardiopulmonary functioning. The present system embodies a multifunction sensor module; however, the medical device 202 is also capable of providing the performance using a series of individual sensor modules to measure O2 and CO2 gas concentrations, gas flow and airway pressure.

An oxygen sensor 210 typically measures the amount of oxygen present in the flow of gas through the patient's airway may be used to measure gas parameters in accordance with the present disclosure. The oxygen sensor may be equipped to measure the proportion of oxygen in the gas being analyzed. An example of an oxygen sensor that may be incorporated as an airway sensor is the Fibox 4 trace provided by PreSens Precision Sensing from Regensburg, Germany. According, when the oxygen sensor is placed in the patient airway, a percentage or amount readout of oxygen that is present within the airway may be recorded. In one embodiment, the oxygen sensor is attached to an inner surface of another airway sensor, such as a flow sensor or capnography sensor, or may be located elsewhere along the patient airway. Oxygen is measured contactless through a transparent vessel wall. Preferably, the sensor has a measurement range of 0-100% oxygen. In an embodiment, an oxygen sensitive coating may be immobilized on a 125 µm flexible transparent polyester foil. In addition, the sensor could also use other oxygen measurement methods such as a galvanic cell or paramagnetic techniques for example.

A pulse oximeter 212 provides a measurement of the oxyhemoglobin saturation of the patient may be used to measure physiological parameters in accordance with embodiments described herein. Typically, the pulse oximeter is attached to the patient's finger, but could also be attached other locations (e.g., finger, palm, toe, sole or ear, for example). In such cases, the sensor is typically placed at a thin part of the patient's body, such as the fingertip or earlobe, and the device passes multiple wavelengths of light through the body to a photodetector on the other side. The changing absorbance at each of the wavelengths may allow for the medical device/sensor to determine the respective absorbance due to pulsing arterial blood. Alternatively, or in addition, a near infrared sensor for measuring muscle oxygenation content and tissue pH could also be implemented to determine levels of monitor the effectiveness blood flow and tissue oxygenation. Rather than detection through transmission, the reflectance of the multiple wavelengths of light by thicker tissues allow for levels of oxygen at that location to be measured. In the illustrated example, the electrocardiogram sensors 214 are part of the defibrillator electrodes and measure electrical activity of the patient's heart, although it can be appreciated that ECG leads separate from the defibrillation electrodes may be employed. An accelerometer 216 or other motion sensor may be employed to measure movements of the patient and/or rescuer, for example, in moving the patient or apply chest compressions to the patient. In alternative embodiments, the motion of the patient could be sensed by a sternal compression sensor, which is part of the electrode assembly 110 or a separate component entirely. Additionally, the accelerometer could be located on the tube 129 (e.g., at a proximal location) or the rescuers 104, 106.

A flow sensor 221 for measuring the flow rate and volume of air flowing through the patient's airway may be used to measure gas parameters in accordance with various embodiments. The flow sensor 221 is typically located within the airway of the patient, in fluid communication with the portable ventilator or BVM 223. The flow sensor may be in communication with the medical device and, hence, may provide information concerning the flow rate and volume in the patient's airway. Any suitable flow sensor may be employed, such as for example, a differential pressure sensor. The flow sensor may be similar to that described in U.S. Patent Publication 2017/0266399, entitled "Flow Sensor for Ventilation," which is hereby incorporated by reference in its entirety. Accordingly, the flow sensor may provide measurements of inspiratory flow to the patient (e.g., provided by positive pressure breath ventilations) and expiratory flow from the patient (e.g., air breathed out from the patient).

One or more airway sensors 127 may be employed, for monitoring various characteristics of the air flow within the patient's airway. The airway sensor(s) may include a capnography sensor. For example, the capnography sensor may be equipped to measure gas parameters, such as the concentration and partial pressure of carbon dioxide (CO2) in the respiratory gases of the subject. Signals/data from the capnography sensor may be further processed to determine physiological parameters, such as end-tidal CO2 of the patient. In addition, the airway sensor(s) may include a flow sensor that communicates information related to the subject's inspiratory and expiratory gas flow. The airway sensor(s) may further communicate information related to the concentration and partial pressure of respiratory gases, oxygen and water vapor for example. As discussed herein, the airway sensor(s) may include, for example, capnography for measuring CO2, an oxygen sensor for measuring the amount of oxygen, and/or a flow sensor for measuring the rate and volume of flow within the patient's airway, separate or integrated together.

While the illustrated embodiment identifies certain types of sensors, those skilled in the art will recognize that additional sensors could be implemented as well. Likewise, while the specification identifies specific intubation parameters in describing various examples of present system, alternative sensors which perform identical or similar functions may be implemented for enabling the medical device to determine whether steps in an airway management procedure have or have not been completed, for effectively assisting the rescuer in properly carrying out the procedure.

The medical device 202 may include additional components such as a microphone 220 to capture acoustic information of the patient 102 such as the sounds of the patient breathing, or sounds of their heart beating. Additionally, or alternatively, the medical device may further include one or more microphones to capture voice commands from the rescuers 104, 106.

Furthermore, a video laryngoscope 222 is also connected to the medical device 202, which may provide information used as a positioning parameter for the airway management system to determine the current step in the RSI procedure. Laryngoscopes enable rescuers to look at the back of the throat (oropharynx), voice box (larynx) and identify the vocal cords, which provide the critical landmark for insertion of an endotracheal tube into the trachea. Use of a video laryngoscope aids the user in visualizing critical anatomy while also allowing a range of patient-rescuer positions from which to view the airway and insert the endotracheal tube. Additionally, the video laryngoscope provides for a digital recording of the procedure that allows for secondary confirmation of tube placement and post-case review. In an alternative embodiment, the digital recording from the laryngoscope would allow for use of image analysis that could provide additional confirmation that the endotracheal tube was properly placed.

In one embodiment, the medical device 202 communicates with a central facility 224. The communication between the central facility 224 and medical device may be via wireless technologies, like Bluetooth, or wireless telephone networks (e.g., 3G/4G wireless mobile telecommunication networks), or possibly even the Enhanced 911 (or E911) network. The wireless networks are typically secured that require password authentication to access the wireless network. The central facility 224 may be third-party location that stores and/or analyzes information received from the medical device 202. The central facility is generally an emergency response center (e.g., 9-1-1 dispatch), back-end component such as a server, hospital, or ambulance, to list a few examples.

Figure 3A:
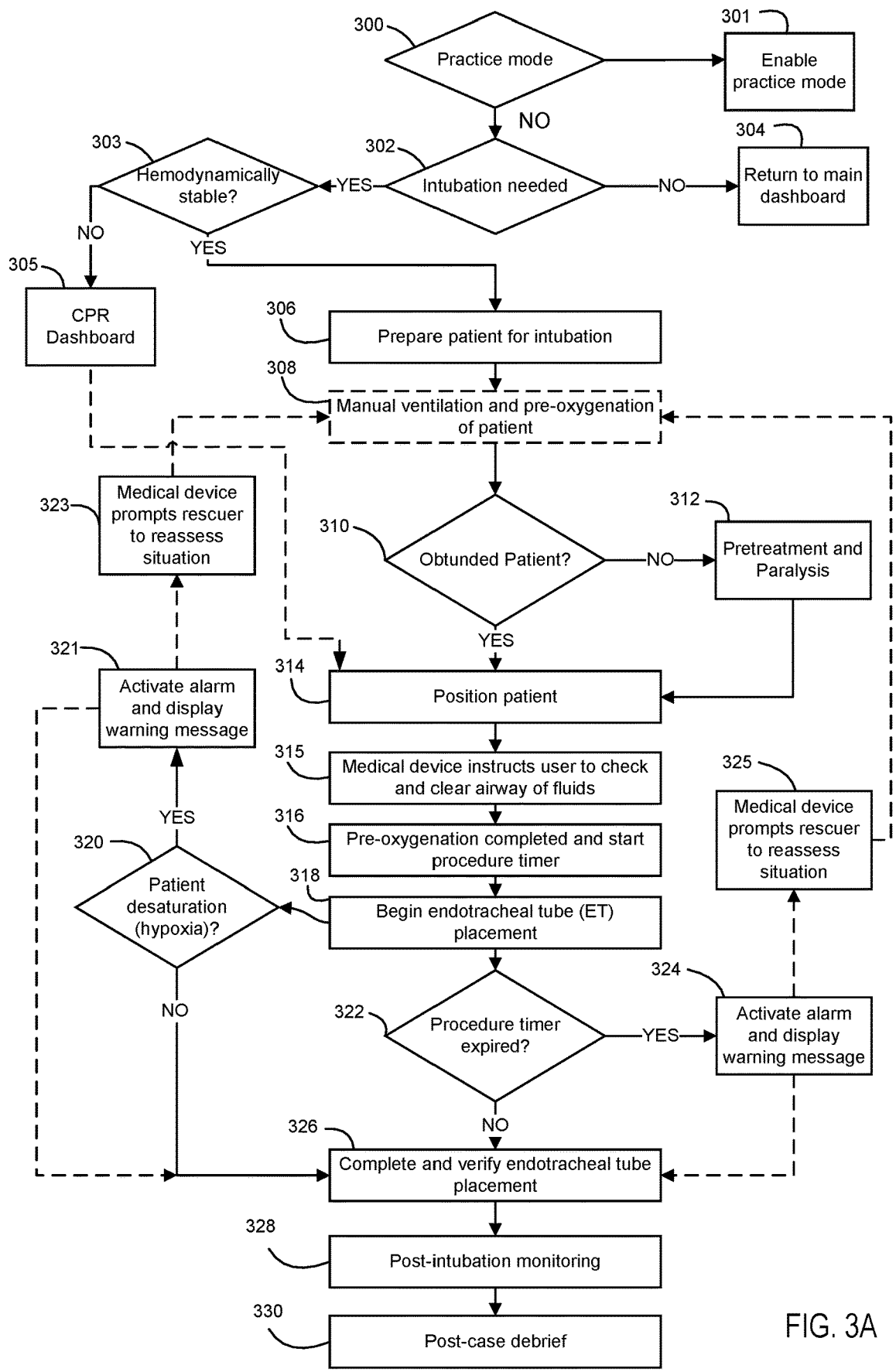
FIG. 3A is a flow chart illustrating steps performed during rapid sequence intubation in accordance with an embodiment.

FIG. 3A is a flow chart illustrating steps performed during an example intubation procedure (possibly rapid sequence intubation or RSI) in accordance with an embodiment. Specific embodiments, and detailed implementation are discussed below. Additionally, while the embodiments described herein are directed to tracheal intubation, aspects of the present disclosure may also apply to other methods of intubation (e.g., nasal intubation, intubation after performing a tracheotomy, emergency intubation procedures, amongst others). In general, the medical device 202 is able to identify which steps are being performed based on a combination of storing information related to which steps have already been performed, and which steps need to be performed. The device is further able to analyze changes in sensor data, and monitor actions being performed on the patient. Illustrated by way of non-limiting example, an advantage of airway management system is the ability to identify when tube placement begins based on the completion of steps leading up to tube placement (and the associated sensor data). In addition, information obtained from the sensors (e.g., intubation parameters such as oxygen ($O_2$) concentration, carbon dioxide ($CO_2$) concentration, gas flow, airway pressure, gas temperature, gas humidity as well as other physiologic and environmental data) are able to provide indications of caregiver progress in the intubation procedure, for example, the pausing in ventilations (e.g., due to a drop in oxygen presence/flow). In some embodiments, the temporary ceasing of ventilations coupled with image analysis of images captured by the laryngoscope 222 can be analyzed as a whole by the medical device to determine that the tube placement has begun. That is, in an example, while a lack of oxygen detected by the oxygen sensor may be an indication that ventilations have paused and the tube placement process has begun, video footage from the laryngoscope may be used as a confirmation of tube placement. Additionally, as shown in the illustrative embodiment, by way of example, steps which are required to be performed by the rescuers are denoted by dotted lines (e.g., step 308 and the manual ventilation and preoxygenation).

In a first step 300, the rescuer is optionally able to place the medical device 202 into a practice/training mode in step 301. This practice mode enables rescuers 104, 106 to practice using the medical device, attaching sensors, prior to using the device in a real-world emergency. Additionally, the device may also include simulations of an emergency situation that allows the rescuers to practice their response to changing medical emergencies. For example, while in practice mode, the medical device 202 displays an alarm indicating that an airway leak has occurred. In this practice mode, the rescuers would then be required to fix the problem (e.g., check the BVM for a bad connection or faulty component). Thus, the rescuers would be able to practice both the procedure as well as be able to more effectively troubleshoot common problems that can arise an emergency situation. Structured, regular practice that focuses on procedures, physical skills, use of the tools, and communication between rescuers is essential to ensuring and maintaining competency. In addition, the practice mode provides for digital documentation and scoring, e.g. performance time, task completion/failure, etc., of rescuer performance enabling formal objective documentation of rescuer readiness and skills maintenance activities.

In the next step 302, the medical device receives and analyzes sensor information to determine whether intubation is needed. The medical device 202 analyzes the received sensor information to identify common symptoms of acute respiratory failure including lack of breathing, agonal breathing, or gasping, to list a few examples. In this case, if the medical device determines that intubation is the best course of action given all of the information provided, it may display a message on its screen that suggests to the user that intubation may be required and/or the medical device may automatically proceed to the next step in providing further guidance in the overall intubation process.

Illustrated by way of a non-limiting example, information obtained by the airway sensor(s) 127 may be indicating to the medical device 202 that ventilation is being performed on the patient and/or oxygen is flowing to the patient, but the pulse oximeter 212 and capnography sensor 218 may indicate that the patient 102 is not adequately receiving the $O_2$ or exhaling $CO_2$. With this information, the medical device 202 is able to identify a range of possible conditions whereby the patient is not receiving adequate ventilation and/or oxygenation, which would result in a context-sensitive alarm that offers a prioritized list of conditions and associated interventions that the user should take to safely manage the patient and correct the failure. For example, if the device detects that manual ventilation is being administered to the patient (e.g., via signals from a flow sensor and/or oxygen sensor disposed within the patient airway), yet the breaths are shown not to be effective (e.g., the expired volume is not equal to the inspired volume and while oxygen is being administered, a significant drop in oxygen saturation levels is detected), then the medical device 202 may provide an indication or suggestion that there is a mask leak and the user should reposition the mask to ensure an adequate seal and breath delivery.

As medical and/or emergency situations are often chaotic and unpredictable, the rescuers 104, 106 will be able to override the diagnosis and recommendations of the medical device 202. Illustrated by way of example, a faulty or improperly placed sensor or leaking airway tube may generate data that is indicative that intubation is needed, while the rescuers 104, 106 own analysis and diagnoses are contradictory. In these types of situations, the rescuers 104, 106 will be able to override the medical device 202. Similarly, rescuers may arrive on-scene where a patient has already been intubated (without the medical device of the present system). In this case, the rescuers may simply wish to verify the placement of the tube and monitor the patient while they provide additional therapy or transport the patient. In this situation, the rescuers are able to skip to the relevant step in the procedure, e.g., post intubation monitoring (e.g., step 328).

Alternatively, in extreme situations where advanced medical personnel is not available, but time is of the essence, then rescuers with limited skills or experience may attach the plurality of the sensors 218 of the medical device 202, and based on sensor inputs provided to the medical device, the medical device may assist the rescuer in a differential diagnosis and/or may guide him/her through the entire procedure step by step, while simultaneously verifying that each step has been done correctly.

Returning to step 302, if it is determined that intubation is not needed (e.g., automatically by the medical device based on sensor inputs, or via a user input), then the medical device 202 returns to a main dashboard interface in step 304. If, however, it is determined that the patient 102 does need intubation, then the medical device 202 makes a determination whether the patient is hemodynamically stable in step 303. In general, a patient is hemodynamically stable if they show positive signs of healthy and effective blood circulation. In the present system, the medical device analyzes data from a combination of sensors (e.g., ECG, blood pressure, capnography, oxygen saturation, and airway flow) to determine if the person's heart function is normal and whether there is normal blood circulation at the extremities. For example, if the ECG signals exhibit regular QRS complexes indicative of depolarization of the right and left ventricles in a manner that would be expected to result in healthy blood flow to and from the heart, the medical device may determine that the patient is hemodynamically stable. Additionally, a non-invasive blood pressure may be taken via an automated blood pressure cuff (not illustrated). If the blood pressure of the patient is within acceptable limits (e.g., 90-120 systolic and 60-80 diastolic), then it may be an indication that the patient is more likely to be hemodynamically stable.

Figure 3B:
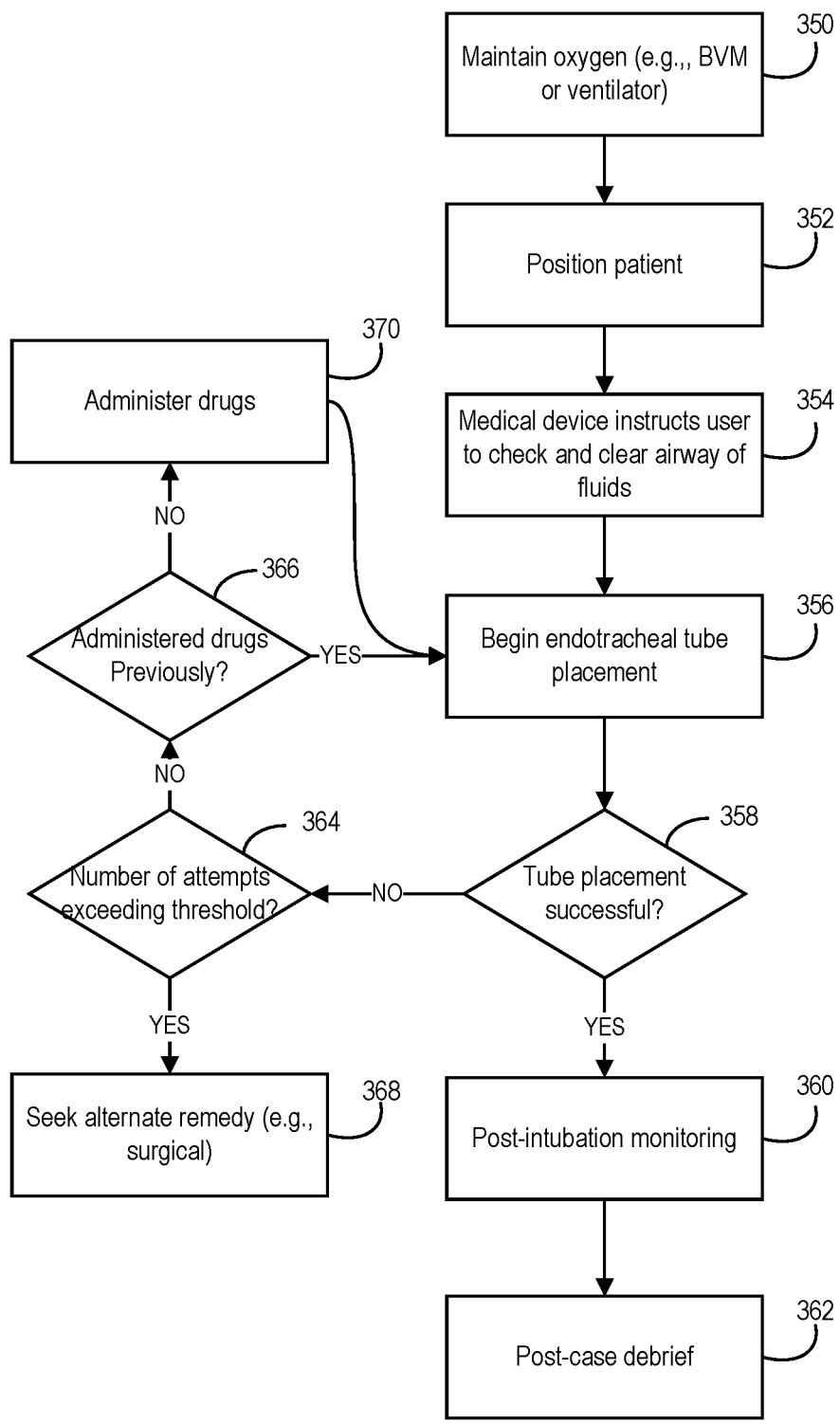
FIG. 3B is a flow chart illustrating steps performed during an intubation procedure involving less steps than that shown in FIG. 3A in accordance with an embodiment.

If the patient is determined not to be hemodynamically stable, then the medical device may be configured to recommend to the rescuer that chest compressions be given and/or automatically present a cardiopulmonary resuscitation (CPR) chest compressions dashboard or interface to guide the rescuers through chest compressions and possibly defibrillation in step 305. It should be noted, however, there are some patients that are not hemodynamically stable, but that do not require chest compressions (e.g. they need pharmacologic intervention and/or fluid resuscitation). In such a case, the rescuer may provide an input to the medical device that overrides the interface for guiding the rescuers toward the administration of chest compressions, and instead may administer the appropriate medication/fluids. Similarly, while accessing or utilizing the CPR dashboard in step 305, it may be detected by the medical device 202 (or become apparent to the rescuers who may provide an associated input to the medical device 202) that the patient requires an immediate intubation in response, without requiring all of the RSI steps described herein. In one example, the medical device (or rescuers) may detect SpO2 or ETCO2 values that indicate that oxygen is not reaching the patient's extremities and/or sufficient CO2 not being expelled from their lungs, respectively. In this situation, the medical device would automatically (or in response to an input from the rescuers) skip to step 314 to position the patient in order to begin the intubation procedure. FIG. 3B provides a flowchart illustrating the steps for a more limited protocol intubation. In some embodiments, a rescuer may simply bypass various steps of the overall RSI procedure by user input. For example, the rescuer may decide that there is insufficient time for a full preoxygenation procedure or drugs to be administered to the patient and, hence, may choose to bypass such steps or indicate that the steps were not carried out. Such decisions may be noted by the medical device and integrated into the patient care record.

If the patient is hemodynamically stable, then the patient 102 is prepared for intubation in step 306. As part of the preparation for intubation, shown in the next step 308, manual ventilation and preoxygenation of the patient begins to ensure that the patient is adequately hyperoxygenated prior to starting the procedure. In a typical implementation, immediately prior to intubation, the patient should be ventilated and preoxygenated for at least 3 minutes (e.g., 30 or more breaths) or for a longer period of time, e.g., 3 to 8 minutes. The purpose of this preoxygenation is to "fill" the patient lungs with oxygen while also expelling as much nitrogen as possible out of their lungs to create a "reservoir" to meet the metabolic oxygen demand during the apneic period as the endotracheal tube is placed. The medical device 202 automatically monitors the duration of ventilation as a gas parameter based on signals (e.g., flow rate and volume from flow sensor, presence of oxygen from oxygen sensor) from the airway sensor(s) while at the same time tracking the SpO2 signal as a physiological parameter to an increase consistent with preoxygenation. When the criteria for preoxygenation are achieved a signal made up of a specific audible signal and visual signal alert the user that intubation can be attempted.

In some embodiments, as discussed further herein, when preoxygenation is initiated, the medical device 202 may start a timer, pre-configurable for example between 2-10 minutes (e.g., 3-8 minutes, 3-5 minutes, etc.), that provides for a minimum amount of time during which preoxygenation should occur. That is, the rescuer should continue to give preoxygenation ventilation until the timer expires, and then move on to the subsequent step. The medical device 202 may detect that preoxygenation is occurring, for example, via a detected rise in oxygen sensed by an oxygen sensor placed in the path of the patient airway. As oxygen makes up about 21% of ambient air, when oxygen is given to the patient, the percent of detectable oxygen in the airway may rise up to 50% or greater (e.g., up to 60%, up to 70%, up to 80%, up to 90%, or greater). As the difference between the inhaled and exhaled oxygen decreases along with flow associated with manual ventilations, the medical device 202 may make a determination that preoxygenation has started. An associated rise in SpO2 (although delayed due to physiological processes) may provide further confirmation that oxygen is being administered. Once it is determined that preoxygenation is occurring, in certain embodiments, the preoxygenation timer discussed above may be initiated.

In one embodiment of the present system, a step 310 is implemented; in this step a determination is made of whether the patient is obtunded (i.e., unconscious). If the patient is not obtunded (i.e., conscious), then pretreatment and paralysis is performed in step 312. If the patient is obtunded, then there is no need for the sedation and paralysis step because the patient is already unconscious. In an alternative embodiment of the present system, there is no determination of whether the patient is obtunded. Regardless of the patient's consciousness, the rescuers 104, 106 immediately move to the sedation and paralysis of step 312. The benefit of skipping the obtunded patient analysis is that the drugs are fast acting and there is minimal additional risk in administering them regardless of the level of consciousness of the patient. Put another way, there are few situations in which the rescuers would not administer the drugs, so it far more efficient and safer to administer the drugs and begin the intubation procedure than it is to spend time determining the level of consciousness of a patient with acute respiratory failure.

Practically speaking, the medical device may collect information that will assist in making a determination of whether the patient is obtunded, for example, via cameras affixed to the device; however, the rescuer is typically in a better position to make that assessment. Accordingly, in some embodiments, the medical device may provide a prompt that reminds the rescuer to assess whether the patient is obtunded, so as to administer a suitable sedation treatment. Such a prompt may be given (e.g., as a display on the device screen, or audible prompt) only for a period of time, and then the medical device may move on to the next step, or the prompt may remain until a user provides an input to proceed to the next step in the overall process.

In general, the pre-treatment (e.g., sedation) and paralysis of the patient is to prevent issues with the tube placement (i.e., make the patient tolerate or compliant with the procedure). For example, gagging or vomiting can occur if the patient is conscious during the tube placement, which can significantly disrupt progress in tube placement. The patient is positioned in step 314. Generally, a preferred position is the "sniffing" position, which is commonly used during laryngoscopy. In general, the "sniffing" position requires flexion of the neck, extension of the head on the neck, and the ear canal to be aligned with the suprasternal notch. In addition, the medical device 202 may provide specific guidance for obese patients whose anatomy may require a modified position to optimize visualization of the airway and passage of the endotracheal tube where the traditional head-back "sniff" position may not be optimal. For example, the medical device includes the Rapid Airway Management Positioner (RAMP) provided by Patient Positioning Systems of Eugene OR, for use with obese patients. Such a device provides pneumatic control in safely raising or lowering the patient's body.

Prior to attempting intubation, the medical device may instruct (e.g., via visual and/or audible prompt) the user to check and/or clear the airway of bodily fluids (e.g., blood, vomitus and secretions) that could obscure the view of the airway and vocal cords in step 315. In addition, the medical device can detect the pause in ventilation while the rescuer checks the airway and in another embodiment the medical device would receive a signal from the medical aspirator that is used to perform oropharyngeal suctioning to clear bodily fluids from the airway. Following the procedure, the medical device 202, via the airway sensor(s), would detect the resumption of ventilation (e.g., via detectable presence of gas flow) and automatically reevaluate the preoxygenation criteria and indicate to the user the patient's readiness for intubation. In one example, the medical device identifies the pause based on the change in sensor data (e.g., ETCO2 waveform disappears) as well as the programing of the medical device which "knows" and "expects" that the rescuers will need to fluid checks, thus the temporary and brief change in data during preoxygenation is expected.

In step 316, preoxygenation is completed and a procedure timer may be initiated in response to the completion of preoxygenation (e.g., completion of preoxygenation may be based on an analysis of data from pulse oximeter 212, capnography sensor 218, and airway flow and pressure sensor (flow sensor) 221 in the airway sensor(s) 127). Such a procedure timer may be a subsequent timer to that initiated during the preoxygenation step. Once preoxygenation has been completed, the oxygen reservoir begins to be depleted once ventilation stops and so there is a relatively short window of time in which the intubation procedure must be completed to ensure that the patient is not dangerously deprived of O2. In step 318, the rescuers (or caregiver) begins the endotracheal tube (ETT) placement. Accordingly, this step 318 during ET tube placement should happen expeditiously before the oxygen reservoir is effectively exhausted.

Simultaneously, the medical device 202 monitors the procedure timer in step 322 and the O2 saturation levels in the patient in step 320 to determine if the patient hypoxemic (e.g., O2 saturation level is below 85-88%). If the procedure timer expires in step 322, then the medical device 202 activates an alarm and displays a warning message in step 324 indicating that the intubation attempt exceeded clinical norms. The warning may further include audible alarms such as sirens, tones, or voice commands indication that the procedure timer has expired. The alarm may further provide haptic feedback to the rescuer, e.g., via wrist-worn and/or heads up display devices. At this point, the rescuer performing intubation must make a decision whether to abort the procedure and manually ventilate and oxygenate the patient 102, as provided in step 308 or, assuming the procedure is nearly complete, override or disregard the warning and complete and verify the endotracheal tube placement in step 326. Following a failed intubation attempt the medical device 202 may prompt the rescuer to reassess multiple criteria to optimize the probability of success on their next attempt in steps 325 and 323. Returning to step 320, if the O2 saturation falls below a threshold (e.g., 85-88%, 85-93%, 88-93%, 88-91%, or some other configurable amount) or exhibits a rapid decrease and/or if an indicator of oxygen reserve (e.g., oxygen reserve index) falls below a threshold (e.g., 10-50%, 10-30%) or exhibits a rapid decrease, then the rescuers must make a decision, as before, whether to abort the procedure and manually ventilate and oxygenate the patient 102 in step 308 or override the warning and complete and verify the endotracheal tube placement in step 326. Following the standard of care, the medical device 202 may be configured to allow for three (3) intubation attempts before prompting the user to use an alternative supraglottic airway as an alternative to an ETT. In various embodiments, the medical device 202 may count the number of attempts of intubation that has occurred and provide an indication for how many intubation attempts have occurred. The medical device 202 may detect that the rescuer has gone back to step 308, for example, by sensing that the BVM is being used for manual ventilations (e.g., accelerometers on the BVM, air flow from a flow sensor, oxygen detection by oxygen sensor in patient airway). Additionally, a separate dashboard (not shown) may be presented for a patient that required multiple intubation attempts. In this situation, the medical device 202 provides additional feedback and prompts to the user regarding patients that are difficult to intubate. For example, alternative head positions, different tube sizes, or seeking assistance of a more experience rescuer.

In the case of either a successful intubation or a failed attempt, the medical device 202, via the airway sensor(s) detects the return of ventilation using the flow signal. For a successful intubation, the airway sensor(s) detects removal of mask from the module and then follows the procedure described below to verify endotracheal tube placement. A failed attempt is indicated by the presence of the mask whereby the medical device 202 prompts the user to reassess the situation, 325, (e.g., patient position, additional clearing of the airway, a change in rescuer, etc.) while at the same time ensuring preoxygenation and ventilation are occurring based on the airway flow signal.

In the next step 328, post intubation monitoring is performed to ensure that, for example, the tube was placed in the patient's airways, and not in their esophagus. This step 328 may include active monitoring of the intubation parameters (e.g., patient vital signs, graphical trends of vitals, SpO2, ETCO2, heart rate, respiratory rate, ECG, etc.). Lastly, in step 330, the medical device 202 gathers and presents information for a post-case debriefing to allow the rescuers to record and/or review information related to the procedure, e.g., prompting the user to record the depth of the ETT placement as well as other relevant information associated with the procedure.

FIG. 3B is a flow chart illustrating steps performed during an emergency intubation that involves less steps than the protocol shown in FIG. 3A, in accordance with an embodiment.

As detailed above, there may be some scenarios in which rescuers need to skip one or more step of during rapid sequence intubation and perform an intubation more quickly without all of the steps of the RSI. Accordingly, the rescuer may choose to bypass certain steps that he/she deems to be unnecessary in view of the urgency of the situation. Such steps may be bypassed by rescuer input into the medical device and, in some cases, the decision(s) may be recorded by the medical device for integration into the patient care record. In the first step 350, the rescuer maintains oxygen supply, such as with a BVM or using the portable ventilator (e.g., provided to the patient via a sealed mask, nasal cannula, or other method). In the next step 352, the rescuer positions the patient for intubation. As detailed previously, this may include positioning the patient in the "sniffing" position, which requires flexion of the neck, extension of the head on the neck, and the ear canal to be aligned with the suprasternal notch. Next, the medical device 202 may instruct (e.g., via visual and/or audible prompt) the rescuer to check and/or clear the airway of bodily fluids (e.g., blood, vomitus and secretions) that could obscure the view of the airway and vocal cords in step 354.

In the next step 356, the rescuer begins the endotracheal ET tube placement. As before with rapid sequence intubation, this procedure should happen expeditiously as the patient's oxygen reservoir may be effectively exhausted or the patient may already have undergone some amount of time without oxygen.

In the next step 358, the medical device 202 determines whether tube placement was successful. Typically, this verification is accomplished by measuring one or more physiological parameters (e.g., presence of CO2 waveform, sufficient change in transthoracic impedance) of the patient along with auscultation of the patient at different sites. Possible methods for verifying tube placement are described in detail below with respect to FIGS. 15A-15G, although other methods are possible.

If the tube placement was successful, then the medical device 202 may move into post-intubation monitoring in step 360. During post-intubation monitoring, the medical device 202 may perform regular checks to confirm that the ET tube remains properly placed. For example, the device may measure one or more physiological parameters similar to that used during the initial ET tube placement at regular intervals to ensure that the ET tube does not become dislodged. Additionally, a post-case debrief can be performed in step 362 as well, where recorded parameters, waveforms, and other information associated with the medical event are made accessible for review. As detailed before, step 360 may include active monitoring of certain intubation parameters (e.g., patient vital signs, graphical trends of vitals, air flow in the patient's airway, SpO2, ETCO2, heart rate, respiratory rate, ECG, etc.) via the display on the medical device and/or on the portable computing device 225. Similarly, the post-case debriefing of step 362 allows the rescuers to record and/or review information related to the procedure.

Returning to step 364, if the tube placement was not successful, then the medical device 202 may determine if a certain number of attempts exceeding a threshold (e.g., three or more attempts) have been made at intubation in step 364. If a number of attempts exceeding the threshold have been made, then the medical device 202 provides an indication or alert to seek an alternative remedy (e.g., a tracheotomy, other course of action) in step 368. The attempts may include attempts made from multiple users, or possibly only attempts made by a single user (e.g., most senior rescuer, specialist).

If a number of attempts less than the threshold have occurred, then the system determines whether drugs (e.g., paralytics) have been provided in step 366. If the drugs have previously been administered, then the medical device 202 reverts back to step 356 to initiate another attempt at endotracheal tube placement. While not illustrated, the medical device 202 may display an attempt counter and/or other message indicating whether to continue with another attempt.

If drugs have not been previously administered, then the medical device 202 may provide an indication, such as a reminder or suggestion, to provide drugs (e.g., paralytics) in step 370. It should be noted that the drug administration may or may not be needed. Likewise, they may or may not even be available. As such, the final decision to provide the drugs is made by qualified medical personnel. In certain embodiments, the medical device 202 may provide a reminder or suggestion to administer an appropriate drug, for example, according to a default protocol, and the caregiver may follow or ignore the suggestion/reminder. Such a suggestion or reminder may remain on the display of the medical device, may disappear after a certain time period, or remain disappear when the medical device receives an input for the suggestion or reminder to be removed. As further detailed below, the medical device 202 may provide dosage information, for example, based on the actual height or weight, and/or ideal body weight of the patient (depending on the medication and dosage requirements).

Figure 4A:
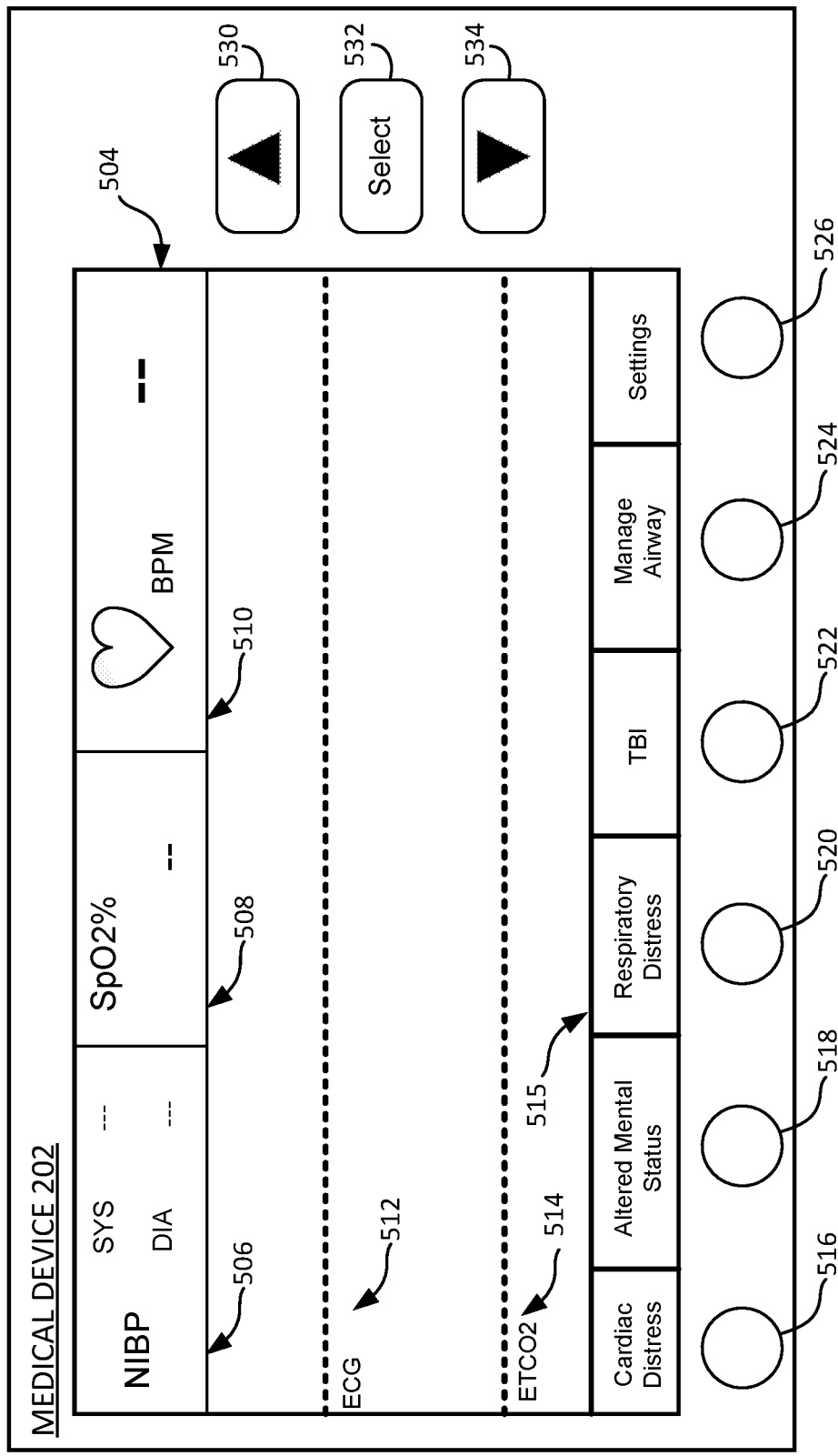
FIG. 4A is an exemplary user interface (dashboard) of a medical device in accordance with an embodiment.

FIG. 4A is an exemplary user interface of the medical device 202. In the illustrated embodiment, the medical device 202 includes a display 504 for displaying patient information in a graphical user interface.

The graphical user interface presents relevant information to rescuers concerning the patient. For example, window 506 displays noninvasive blood pressure (NIBP) including systolic and diastolic values, window 508 displays peripheral oxyhemoglobin saturation (SpO2) and window 510 displays the patient's heart rate in beats per minute (BPM).

The display 504 further includes the ability to display electrocardiogram (ECG) waveforms and end-tidal carbon dioxide (ETCO2), which is the maximal partial pressure of CO2 at the end of an exhaled breath of the patient. As discussed further below, trending of patient vitals may also be provided by the medical device.

Additionally, the illustrated embodiment of the medical device 202 includes a series of soft keys 516-526 and associated display windows 515. The medical device 202 further include arrow keys 530, 534, and a select button that enables a user to scroll and select options presented in the interface. In the illustrated embodiment, the soft keys are programmed to enable a user to select between different "dashboards," for assisting the user in diagnosing and ultimately carrying out the most effective treatment for the patient. Each dashboard may be selected depending on the particular situation at hand, and may display information relevant to that situation. Such dashboards include, for example, cardiac distress, altered mental status, respiratory distress, traumatic brain injury, or other settings based on a library of patient conditions and associated dashboards. Pressing any of the soft keys will override the medical device 202, and immediately take the rescuers to the desired dashboard for assisting the rescuer facing that particular patient situation. The graphical user interface and the information presented to the user would change based on which dashboard is selected, an example of the dashboard suitable for treating a patient who has suffered from traumatic brain injury is provided below in FIG. 4B. Similarly, to the above, selection of an airway management dashboard, e.g., via selection 524, also accessible from one or more of the other dashboards, may immediately bring the medical device into the process flow generally provided by FIG. 3 and further discussed herein. In some cases, the medical device may be in a particular dashboard mode, and if a determination is made that the patient is in need of intubation, the medical device may then proceed down the airway management pathway, or may provide a suggestion on the user interface for the user to confirm to move forward with the intubation procedure.

In an alternative embodiment, the medical device 202 utilizes a touch screen display rather than soft keys. In this embodiment, all, or nearly all of the front face of the medical device is a touch screen display device and the soft keys are removed. In yet another embodiment, the medical device 202 includes one or more dials that enable the rescuers to change dashboards, functionality of the medical device (e.g., set the medical device to be in defibrillator mode, monitor mode, ventilation mode, CPR mode), make selections, or change which information is displayed.

Figure 4B:
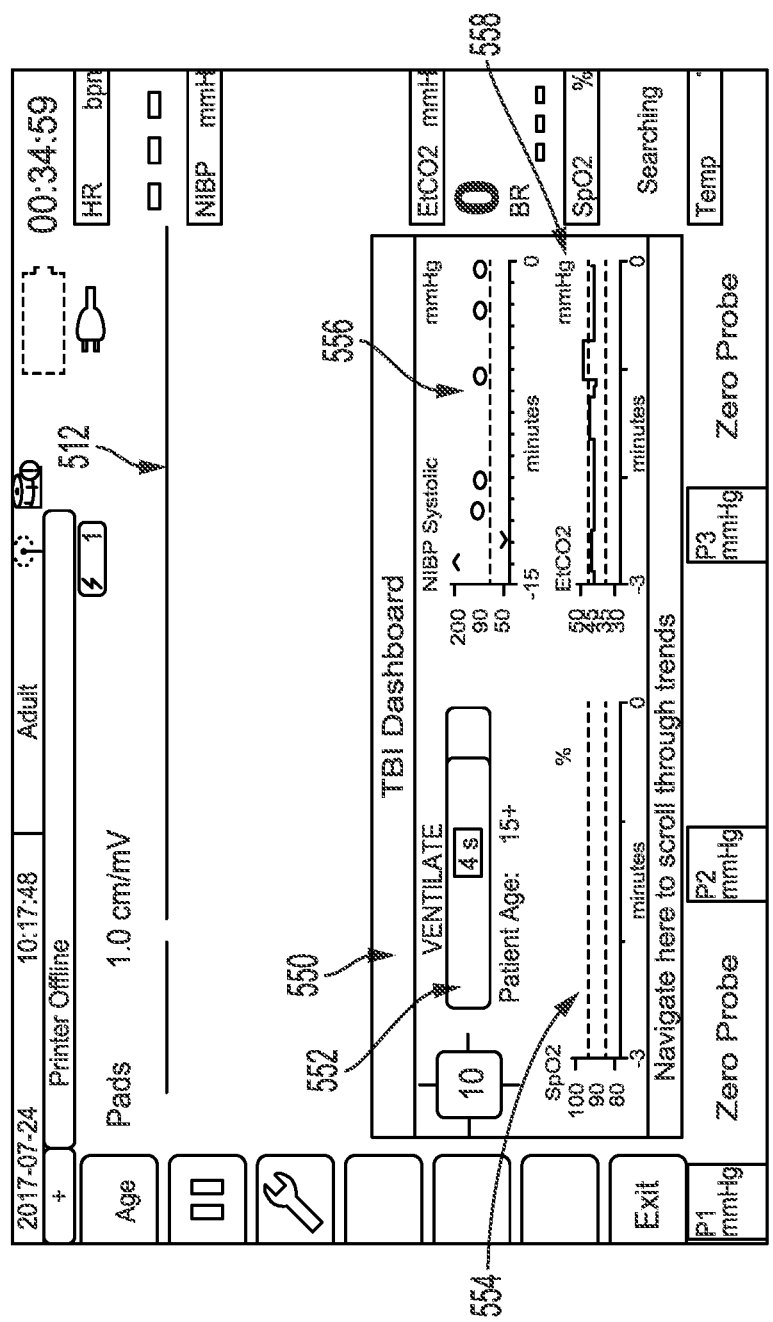
FIG. 4B is an exemplary user interface (dashboard) of a medical device for treating a traumatic brain injury (TBI) patient in accordance with an embodiment.

FIG. 4B is a screenshot of a non-limiting, current implementation of a traumatic brain injury (TBI) dashboard 550 that would be displayed in response to a rescuer selecting the TBI dashboard soft key 522. In this particular example, the TBI dashboard 550 includes a ventilation timer and status bar that provides an indication of when to ventilate next. Other ventilation parameters for providing ventilation feedback to the rescuer who is providing manual ventilation may be provided, such as tidal volume of each positive pressure breath and the rate of ventilations (e.g., in breaths per minute).

Additionally, the TBI dashboard 550 further displays trends such as the SpO2 trend 554 of the patient 102, a NIBP trend 556, and EtCO2 558. Trends are useful in helping to determine and/or predict the patient's clinical progression. For example, patients' oxygen saturation will rarely drop from normal levels to hypoxemic levels instantly. Rather, there is typically a trend of falling oxygen saturation (desaturation), which is an indication that patient may soon be in danger. If the device is only monitoring or displaying "instant" oxygen saturation levels and/or only analyzing whether the patient is above a predefined threshold (e.g., 88 to 94%), then the device will not generate an alarm until after the patient has fallen below the threshold. Thus, it is beneficial to monitor trends, in addition to "instant" oxygen saturation levels to enable the medical device 202 to identify developing issue and allow the rescuers to intervene prior the dangerous situation (e.g., reinitiate manual ventilation). Obviously, identifying similar trends with respect to heart rate, ETCO2, and blood pressure would also be beneficial for similar reasons, for example, as compared to baseline or previous vital sign values. In addition to displaying sensor data the medical device 202 may also use changes in the audible tone and/or frequency to indicate changes in the physiologic parameters or airway gas parameters. This allows rescuers to maintain their focus on the patient while alerting them to changes in the patient's condition.

While the reference numerals have been omitted for clarity of the figure, the embodiment of FIG. 4B includes (e.g.) windows displaying oxygen saturation, noninvasive blood pressure (NIBP), heartrate, as detailed in FIG. 4A.

Figure 4C:
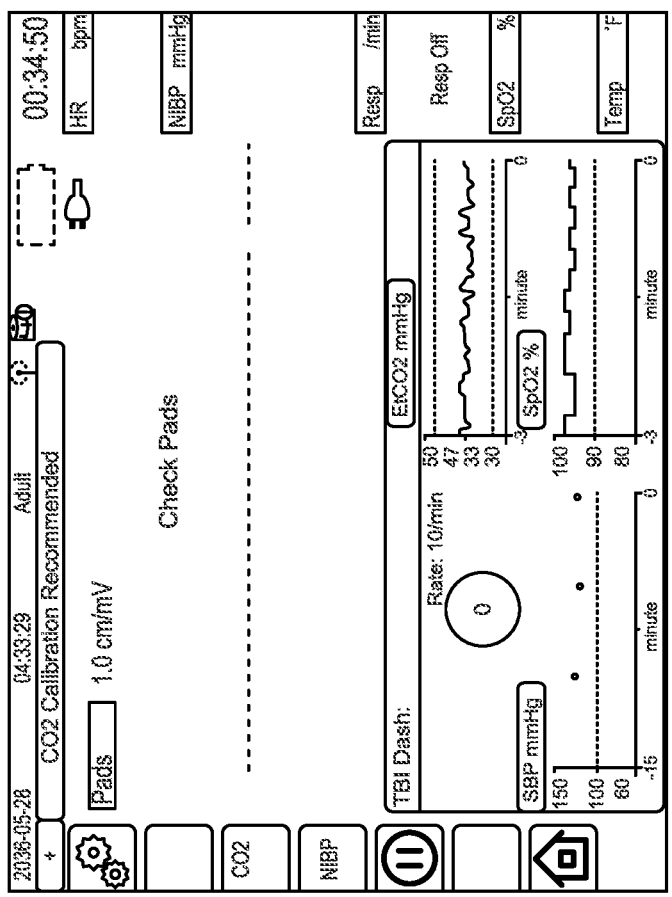
FIG. 4C is an exemplary alternative user interface (dashboard) of a medical device for treating a traumatic brain injury (TBI) patient in accordance with another embodiment.

FIG. 4C is an exemplary alternative user interface (dashboard) of a medical device for treating a traumatic brain injury (TBI) patient in accordance with another embodiment. This dashboard illustrates the flexibility of the dashboard and a possible alternative display, showing relevant parameters, for example, trending ETCO2, trending blood pressure readings, trending SpO2 values, and ventilation feedback.

Figure 5:
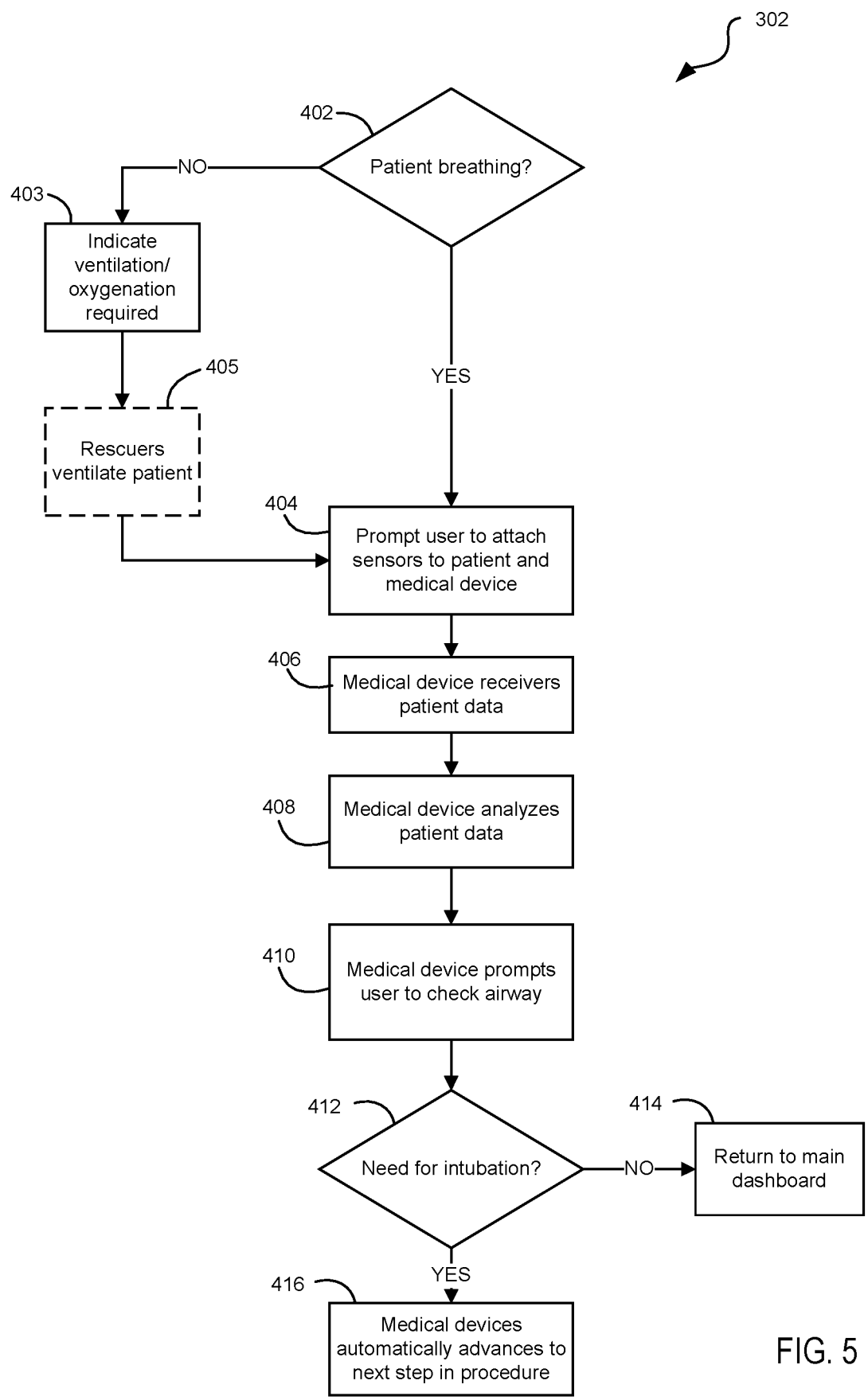
FIG. 5 is a flow chart illustrating steps performed during a determination of whether a patient needs rapid sequence intubation in accordance with an embodiment.

With reference back to step 302 of FIG. 3, FIG. 5 is a flow chart illustrating steps performed during a determination of whether a patient needs rapid sequence intubation in accordance with various embodiments.

In the first step 402, the rescuer encounters the patient and determines if the patient is breathing. This step is essentially a differential diagnosis performed by the rescuer to determine whether the patient needs CPR chest compressions, ventilations, defibrillations, or some other appropriate emergency treatment. If the patient is not breathing, then in step 403 the medical device may optionally indicate that assisted ventilation and/or oxygenation is required and the rescuers ventilate the patient in step 405. Or, once the rescuer determines that ventilations are required and subsequently administers positive pressure breaths, the medical device may detect that ventilations are being given (e.g., via an air flow sensor positioned in the patient airway, optionally included along with the BVM and/or airway sensor(s)). In step 404, the medical device prompts the rescuer to attach sensors (e.g., one or more of sensors 210-221) to the patient 102, so as to be communicatively coupled with the medical device 202. The medical device 202 then receives and analyzes the intubation parameters obtained from the sensors (e.g., physiologic, non-physiologic, airway gas measurements) in steps 406 and 408, respectively. In certain embodiments, once the medical device receives data from the one or more sensors attached to the patient, the medical device then advances to the next step in determining whether there is need for intubation.

As the medical device is receiving and analyzing the patient data, the medical device 202 may also optionally display a prompt reminding the rescuer to check the patient's airway in step 410. In addition to the prompt to check the patient's airway, the medical device 202 may further provide a prompt for the rescuer to suction/clear the airway if needed. Such a prompt may be a reminder for the rescuer to check whether the airway needs to be suctioned or cleared, to prevent aspiration and facilitate intubation.

In step 412, the medical device 202 determines if the patient 102 requires intubation. In general, the determination whether the patient requires intubation may be a determination of whether the patient has some form of acute respiratory failure (e.g., lack of breathing, apnea, gasping, labored or agonal breathing, etc.) or some other condition that could affect the patency of the airway (e.g. facial trauma or burns). In one implementation, this is done by initially placing the BVM, which may include one or more of the airway sensor(s), over the patient's mouth and attaching a pulse oximeter 212 to the patient 102. Based on the measured sensor data, the medical device 202 automatically analyzes the patient breathing (or lack thereof) and oxygen saturation to determine if measured the overall combination of sensor data (e.g., inspiratory flow, expiratory flow, ETCO2 waveform, oxygen saturation) are indicative of acute respiratory failure. Accordingly, depending on data collected from the sensor(s) associated with the medical device 202 (e.g., one or more of ETCO2, oxygen saturation, flow rate), the medical device may make a determination of whether intubation of the patient is needed and, hence, may provide a suggestion for the rescuer to consider moving forward with the intubation process. For example, an ETCO2 value greater than 50 mm Hg (millimeters of mercury) coupled with an oxygen saturation level below 85 to 88% may be indicative of acute respiratory failure. Additionally, the medical device 202 may further analyze the flow rate of gas within the patient airway to determine whether pattern is regular and tidal volume and respiratory rate are able to provide for adequate ventilation or are indicative acute respiratory failure. In various embodiments, the medical device 202 may compare airway gas measurements in the patient airway to the recommended flow volume for the patient height, weight and gender had been met (e.g., an adult male should have inspiratory/expiratory flow volumes of about 400 mL), which may inform the determination by the medical device 202 of whether the patient requires intubation. Or, rather than an automatic determination, a rescuer may simply provide an input into the medical device 202 that intubation is required, and the context-relevant information and promptings may be activated.

If the medical device 202 determines that the patient does not require intubation, then the medical devices returns to the main dashboard, e.g., the graphical user interface shown in FIG. 4 that guides the rescuers 104,106 management and monitoring of the patient in step 414. If the medical device 202 determines that the patient does need intubation, then medical device may prompt or provide a recommendation to the user for intubation and/or may automatically advance to the next step in the procedure. This is in response to changes in sensor data and/or actions being performed by the rescuers which are indicative that the rescuer has initiated the next step in the intubation procedure in step 416.

Figure 6A:
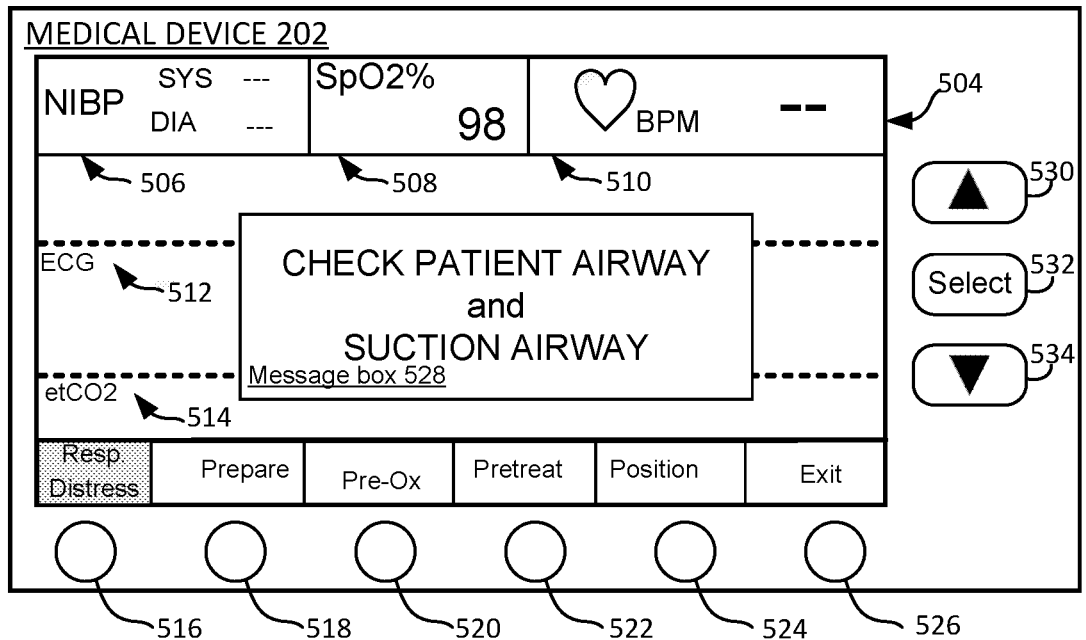
FIGS. 6A and 6B are exemplary user interfaces of a medical device during a determination of whether the patient needs intubation using rapid sequence induction.
Figure 6B:
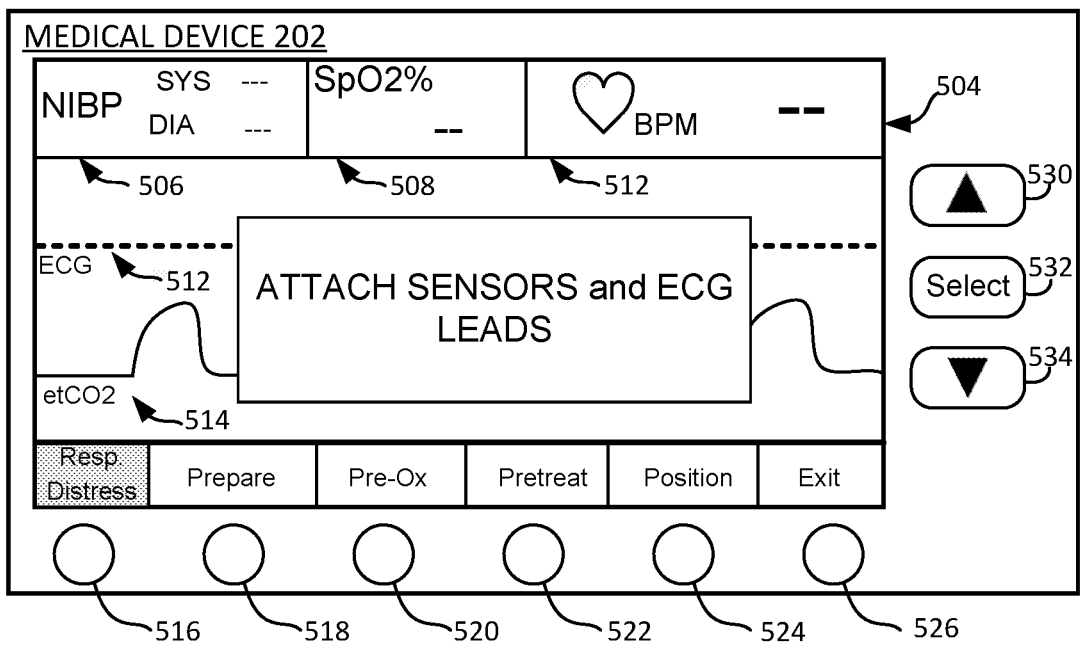

FIGS. 6A and 6B are exemplary user interfaces (or dashboards) of the medical device 202 displayed during the determination of whether the patient needs rapid sequence intubation.

As shown in the illustrated example and described with respect to the steps in FIG. 5, the medical device 202 displays prompts or reminders to the rescuers prior to, during, and after the intubation procedure. In the illustrated figures, a message box 528 prominently displays prompts and/or reminders to the rescuers 104, 106 (e.g., to check patient airways, section airways to remove bodily fluids/secretions, and to attach sensors and ECG leads). Additionally, the soft keys and their associated text and/or touchscreen inputs identify which step is currently being performed by highlighting the current step in the intubation procedure. Additionally, the text displays which steps are next in the procedure (slowing the rescuers to override the procedure as the medical situation dictates).

In an alternative embodiment, the medical device 202 prompts the rescuers 104, 106 and requires the rescuers 104, 106 to confirm completion of the steps in order to advance the medical device to the next step in the procedure. This is to ensure the medical device does not inadvertently move to a new step before the rescuers have completed the current step. For example, after preoxygenation has been completed and the rescuers begin tube placement, the ETCO2 waveform will change (and possibly disappear) as the patient is no longer receiving manual ventilations and/or oxygen. If, however, there was a sensor failure (or other incorrect sensor reading), the medical device 202 may be configured to automatically move to the next step in response to the changed sensor reading, which appears to indicate that preoxygenation was stopped by the rescuers. By including prompts and requiring the rescuers to confirm the completion of the steps, any potential harm from false positives is eliminated.

Figure 7:
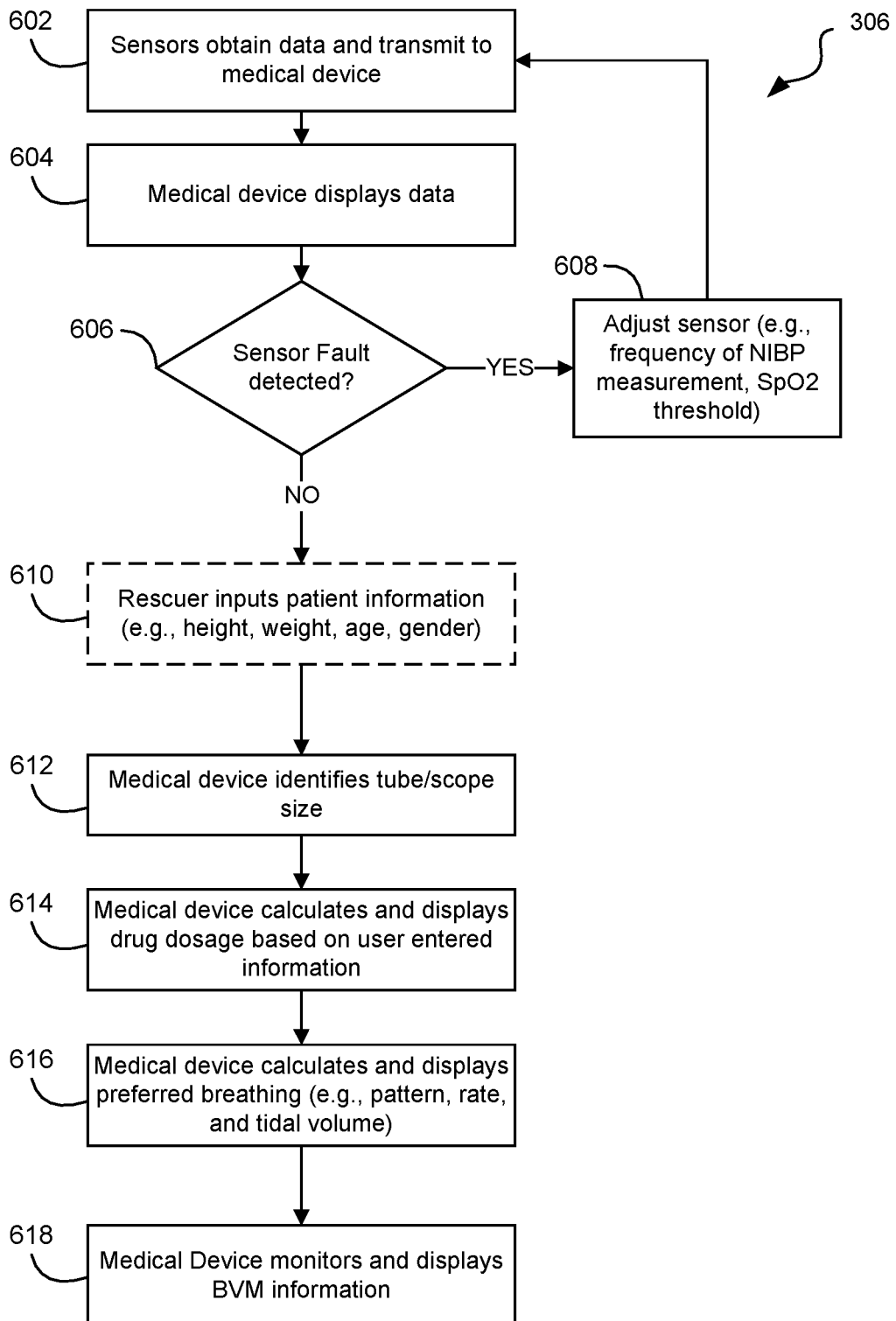
FIG. 7 is a flow chart illustrating steps performed while preparing a patient for a rapid sequence intubation procedure in accordance with an embodiment.

FIG. 7 is a flow chart illustrating typical steps performed while preparing the patient 102 for a rapid sequence intubation procedure in accordance with embodiments discussed herein.

In the first step 602, the plurality of sensors (e.g. sensors 210-221), for example of the medical device 202 obtain the patient data (e.g., physiologic, non-physiologic, airway gas measurements) and transmit the obtained data to the medical device 202 to be displayed on the screen of the display 504. Some examples of information provided to the medical device may include NIBP, SPO2, ETCO2, heart rate, respiratory rate, and tidal volume. Next, in step 604 the medical device 202 may display the received patient data in the display 504.

The medical device 202 may determine if there was a sensor fault (e.g., sensors need adjustment) in step 606. If the sensors need adjustment, then (e.g.) the sensor is adjusted (or replaced) depending on the fault. In any case a context-sensitive alarm is triggered alerting the user to the fault or failure while providing instructions to resolve or mitigate the fault or failure. However, if the sensors do not need adjustment, then the medical device 202 prompts the rescuers to enter patient information, such as height, weight, age, and gender in step 610. This patient information is beneficial because a number of calculations may be determined based on the patient's information. For instance, the dosage of drugs required may differ based on patient information (e.g., larger patients may require larger drug dosages than smaller patients). Or, the appropriate ET tube size may be different for different types of patients (e.g., a child may require a smaller ET tube as compared to an adult).

Next, in step 612, the medical device 202 identifies the tube and laryngoscope size based on the entered information from step 610. Alternatively, the rescuers may make the determination of the tube or laryngoscope scope size based on their own assessment of the patient 102, which may or may not differ from the tube or scope size recommended by the medical device.

Next, based on the patient's height, weight, age, and gender, the medical device 202 may calculate and display the recommended drug dosage in step 614. Commonly used drugs include: Etomidate, Fentanyl, Ketamine, Midazolam, Propofol, Succinylcholine and Thiopental. For example, a typical dosage for Etomidate may be 0.3-0.4 mg/kg. In various embodiments, the drug dosage calculation based on entered patient information may be pre-configured by a medical professional. Preferably, the rescuers would follow the recommendations of the medical device 202 whose programing reflects the process defined by the local or organizational medical guidance, but the rescuers are always able to override the recommendations of the medical device.

Next, in step 616, the medical device 202 calculates and displays indicate the preferred pattern of ventilation, breathing rate and tidal volume, for the patient 102 based on the entered patient information and best practice information stored in the memory 209 of the medical device. These ventilation parameters may be used by the medical device 202 to provide feedback to the rescuer during manual ventilation, so that the rescuer is better able to provide ventilation at a rate and tidal volume appropriate for the patient. Lastly, in step 618, the medical device 202 monitors and displays BVM performance information in the display of the medical device 202 in step 618. For example, the medical device 202 monitors for deviations from the prescribed patterns (e.g., waveform), rate (e.g., breaths per minute) and tidal volume (e.g., mL). An alarm or other feedback may be triggered to alert or otherwise better guide the user in the event the prescribed pattern of ventilation is not followed or if other conditions (e.g., mask leak or high airway pressure), which could affect patient safety, are detected.

Figure 8A:
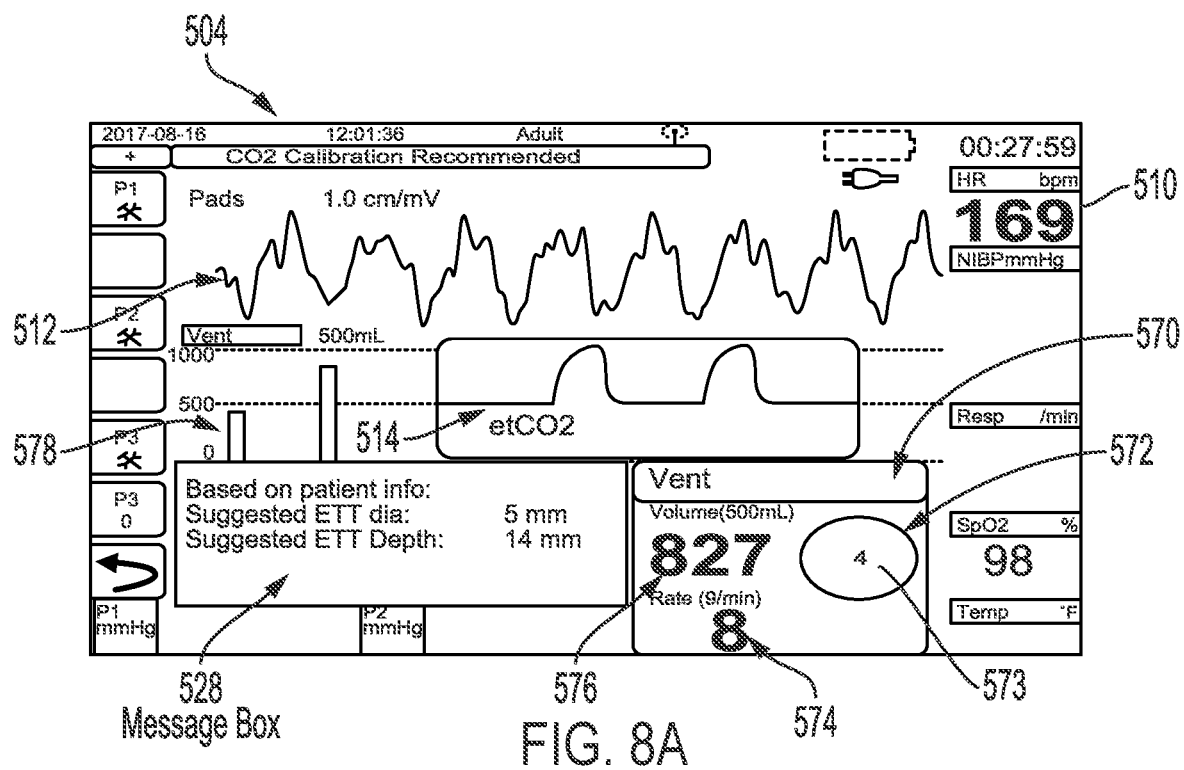
FIGS. 8A and 8B are exemplary user interfaces (dashboards) displayed on a medical device during the preparation of a patient for rapid sequence intubation in accordance with an embodiment.
Figure 8B:
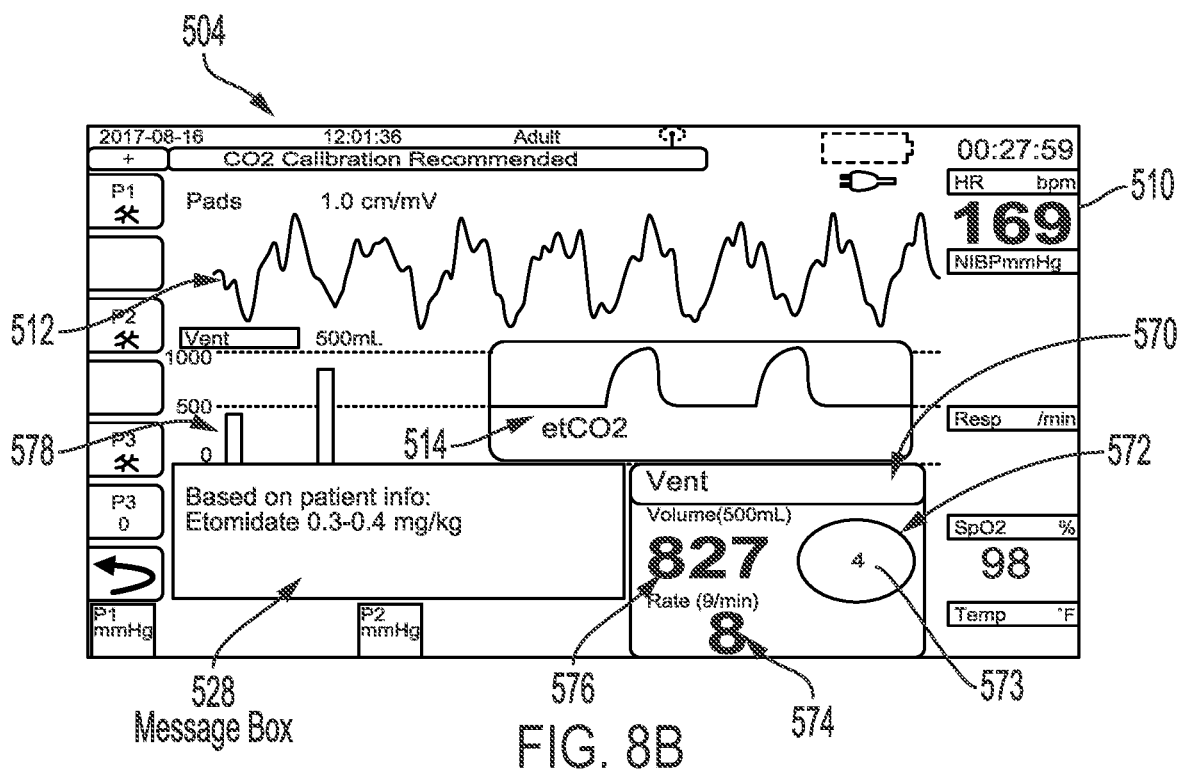

FIGS. 8A and 8B are exemplary dashboards (e.g., user interfaces) displayed on the medical device 202 during the preparation of the patient for rapid sequence intubation.

FIG. 8A illustrates an exemplary ventilation dashboard 570, which includes an animated indication of ventilation 572, which provides real-time feedback to the user regarding their performance with the BVM. In the illustrated example, the indicator 572 is a circle, which fills as the ventilation bag 112 is squeezed to deliver a breath to the patient. If the rescuers are delivering the appropriate tidal volume, then the entire circle fills. If the delivered tidal volume is less than the target volume, then only part of the circle fills. And if the rescuers deliver an excessive tidal volume, then the circle fills complete, and gives a notification that an excessive tidal volume has been delivered (e.g., possible over-filling, color change, warning message of excessive volume). Additionally, the color of the circle may change from, e.g., green to red or yellow when the user is not ventilating at the proper breathing rate. An animated timer 573 provides a countdown indication for when to deliver the next ventilation. Additionally, a volume indicator 576 displays the desired and/or actual tidal volume delivered (in this particular example, the desired tidal volume is preconfigured and the actual tidal volume delivered is displayed). Similarly, the ventilation tracker 578 shows when breaths were delivered and their respective tidal volume in bar graph form. In the illustrated example, the ventilation tracker 578 is shown in place of the ETCO2 waveform; however, in alternative embodiment, the ventilation tracker 578 and the ETCO2 waveform may be shown at the same time concurrently.

The dashboard 570 further displays desired and/or actual rate of ventilation 574, which display the number of breaths per minute that rescuers should deliver to the patient. In this particular example, the desired rate of ventilation is preconfigured and the actual ventilation rate is displayed.

While not expressly shown in the figures, for patients that are undergoing agonal breathing and may benefit from assisted ventilation, the ventilation feedback may provide cues for the rescuer to provide such assistance. For instance, data from the sensor(s) may provide some indication that the patient is breathing (e.g., flow sensor may detect positive or negative pressure arising from the patient), and so may then provide a cue (e.g., audible, visual, haptic) for the rescuer to immediately initiate a positive pressure breath in support of the patient's effort.

FIG. 8A further illustrates an example of how the medical device 202 is able to suggest an endotracheal tube (ETT) size based on, e.g., the patient's information (e.g., height, weight, age and gender). In general, there are many different standard tube sizes. Which size tube is required or preferred, is generally based on the patient's information. Illustrated by way of example, in younger children, the typical diameter for children (in millimeters) is calculated as: (age in years/4)+4; and the depth of the tube is calculated as: (age in years/2)+12. Thus, a 4 year-old will need a tube that is (4/4)+4 or 5 mm in diameter and 5/2+12 or 14.5 cm, which rounded down to 14 cm. Teenagers and adults typically have less variations, but still have some variations. For example, a teenage male might require the same size an adult female (e.g., a 6.5 mm (diameter) by 18 mm (depth)). Whereas, an adult male (or large teenage) might need an 8 mm depth by 21 mm (depth) tube, for example. Additionally, the patient's information could also be used to recommend the size of an alternative airway, e.g. for a laryngeal mask. For ventilation parameters (e.g. rate, tidal volume) the medical device 202 uses the adult patient's height (centimeters or inches) and sex to determine the required tidal volume and ideal respiratory minute volume which is then divided by tidal volume to determine the respiratory rate.

In the illustrated embodiment, once the patient information is entered, the suggestion tube size is subsequently presented in message box 528. In an alternative embodiment, the information may be provided audibly and/or broadcast to the alternate interface devices (e.g., wrist-worn devices 120, 122 or wearable heads-up display devices).

FIG. 8B further illustrates how the medical device 202 is able to suggest dosage information based on the patient's height, weight, age and gender. As before, upon receiving the patient information, the suggested dosage may be presented in message box 528 in the display 504 of the medical device 202. The information may be presented as the specific dosage amount (e.g., 30 mg based on a 100 kg patient based on guidance of 0.3 mg/kg to be administered) or may provide the dosage ranges. Additionally, some medication dosages are based on the patient's actual weight (i.e., current measured or estimated weight), or their ideal body weight, which is function of their height and gender. Similarly, other treatment aspects such as breath volume are dependent on ideal body weight. In one example, the patient measured weight could be obtained from an electronic litter (or gurney) that is capable of measuring the height and weight of the patient on the device. These devices may then communicate wirelessly to the medical device 202 or portable computing device 225.

While the reference numerals have been omitted for clarity, the embodiments of FIGS. 8A and 8B include windows displaying ECG, oxygen saturation, NIBP, heart rate, respiratory rate, temperature, as detailed with respect to FIG. 4A.

Figure 9:
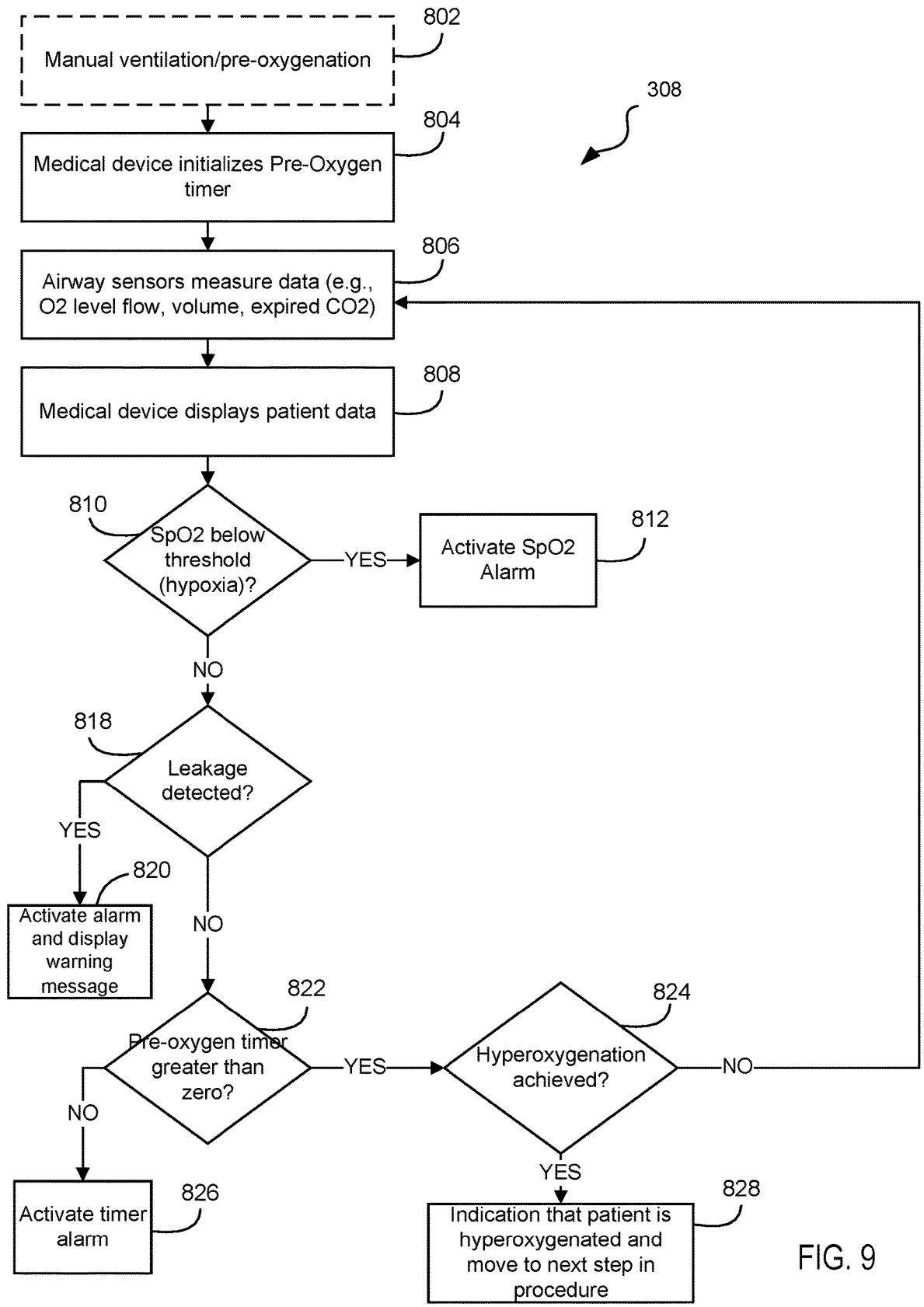
FIG. 9 is a flow chart illustrating steps performed during the preoxygenation of a patient during a rapid sequence intubation procedure in accordance with an embodiment.

FIG. 9 is a flow chart illustrating typical steps performed during the preoxygenation of the patient 102 during a rapid sequence intubation procedure in accordance with embodiments presented herein.

In the first step 802, rescuers provide oxygen to the patient via manual ventilation. As discussed above, the medical device 202 may provide manual ventilation feedback so that the rescuer is more likely to stay within the desired range of ventilation rate and tidal volume. Next, in step 804, the medical device 202 initializes a preoxygenation timer. This preoxygenation timer is based on a recommendation that patients should be preoxygenated for at least three (3) minutes prior to intubation to ensure that the patients have enough oxygen "stored" in their body during the intubation procedure. In addition, the duration of preoxygenation can be modified based on data from the O2 sensor(s) positioned in the patient airway and/or based on the rate at which the patient's lung denitrogenates and becomes a fully saturated anatomical O2 reservoir. In various embodiments, the timer is started automatically in response to one or more of the sensors (e.g., the O2 sensor 210, capnography 218, or flow sensor 221) indicating that ventilation and/or oxygenation is being delivered to the patient 102. For instance, once the oxygen sensor (e.g., provided with the airflow sensor module and/or BVM) senses an appreciable increase or acceptable amount of oxygen present in the patient airway, then the medical device 202 may make a determination that preoxygenation has begun and, hence, may start the preoxygenation timer as a reminder to the rescuer that ventilations should be given at least for the allotted period of time. That is, the medical device 202 may remind the rescuer to continue giving manual ventilations until the timer has expired. In step 806, the O2 sensor positioned in the patient airway measures relevant data, such as oxygen amount or concentration in the air flowing in the airway and then in step 808 the data is transmitted to the medical device 202 and displayed and/or transmitted as described above. As noted above, since oxygen makes up about 21% of ambient air, during preoxygenation, the percent of oxygen in the exhaled gas will increase (e.g., 50% or greater, up to 60%, up to 70%, up to 80%, up to 90%, or greater). The rate of flow detected in the patient airway may also be a positive indication for the medical device 202 to determine that preoxygenation is occurring. Hence, the medical device 202 may use oxygen detection and/or flow rate as indicators of the step of preoxygenation. Similar to the dashboard shown in FIG. 4B or 4C, the medical device 202 may display trending information for SpO2, NIBP, ETCO2 and/or other relevant data in this step in the procedure. During preoxygenation, it may be helpful for patient vitals such as oxygen saturation (e.g., SpO2) to be prominently displayed so that it can be confirmed that the level of oxygen saturation of the patient is increasing or otherwise remaining at an acceptable level. In related embodiments, the medical device 202 would present a composite, based on an aggregated calculation of the physiologic signals, to present a preoxygenation index that indicates the extent to which the patient is preoxygenated. This index could use a value-based indication or a quantized scale (e.g. red, yellow, green) to guide the rescuer as to when intubation should be attempted.

In step 810, the pulse oximeter 212 of the medical device 202 monitors the SpO2 of the patient and determines if the value is below a threshold (e.g., levels associated with hypoxemia, such as below 88 to 92%). Alternative embodiments monitor trend of oxygen saturation, ETCO2, and NIBP, to list a few examples. If the SpO2 is below a set threshold level, then the medical device 202 may activate an alarm in step 812. If the SpO2 remains above the set threshold (i.e., not hypoxemic), then the medical device 202 may further determine whether a leakage is detected in step 818. If a leakage is detected in step 818, then an alarm is activated and a warning message is displayed in step 820 that a leakage is present included instructions on how to resolve the leakage.

If leakage is not detected, then the medical device 202 determines if the preoxygenation timer is greater than zero in step 822. While the leakage detection step is shown as step 818, in a typical implementation, leakage detection may be implemented anytime the patient 102 is connected to a device delivering ventilation and/or oxygen (e.g., BVM or ventilator). In general, leakage may be detected by analyzing the inspiratory and expiratory flow patterns or rates, and pressure signals by the flow sensor 221. Ideally, the inspiratory and expiratory tidal volumes should be approximately equal. If the expiratory tidal volume is significantly smaller than the inspiratory (e.g., 400 mL inspiratory and only 150 mL expiratory), then the medical device 202 may determine that a leak is present and trigger and alarm with mitigation instructions.

If the preoxygenation timer is not greater than zero (i.e., timer expired), then the medical device 202 may activate an alarm in step 826 indicating that the preoxygenation timer has expired. This time is a general reminder or guideline to ensure that patient is preoxygenated for at least three minutes. Depending on the patient condition, saturation levels or breathing pattern, preoxygenation may take longer. In one embodiment, the timer automatically readjusts based on measured oxygen saturation values and acts as more of a prediction of how long until hyperoxygenation has been achieved. In some embodiments, while not expressly shown in the figure, once the timer has expired, the medical device 202 may make a determination of whether a suitable level of hyperoxygenation has been achieved, as discussed below.

If the preoxygenation timer is greater than zero, then the medical device 202 may make a determination of whether hyperoxygenation and/or denitrogenation hyperoxygenation in the patient 102 is achieved in step 824. This may be determined based on signals measured by the airway sensor(s). In general, air is comprised of (about) 21% oxygen and 79% nitrogen (and some other trace gases). Thus, unenriched ventilation with air does not maximize the lung's ability to store oxygen. The goal of preoxygenation is to replace as much nitrogen from the patient with oxygen and create an oxygen reserve, for supplying oxygen to the patient during the apneic/nonventilated period during endotracheal tube placement. In a preferred embodiment, in which the BVM or ventilator is delivering enriched oxygen, the airway management system is verifying, e.g., that the inspiratory flow is 100% oxygen and the expiratory flow is, e.g., ~90% oxygen (i.e., the vast majority of expelled gas is oxygen, which indicates the oxygen reserve is full). If the patient is not expelling greater than 90% oxygen, for example, then the patient is determined to not be hyperoxygenated.

If the patient is sufficiently hyperoxygenated, then the medical device 202 provides an indication that patient is hyperoxygenated and may then move to next step in intubation procedure in step 828. If the patient is not hyperoxygenated, then the medical device 202 may return to step 806 to continue measuring ventilation and O2 delivery to the patient. While the illustrated embodiment of steps FIG. 9 is illustrated as a series of sequential steps, the medical device 202 typically is monitoring, e.g., the SpO2, leakage, and the timer substantially simultaneously. When preoxygenation is completed, the medical device 202 may initialize a subsequent procedure timer (discussed further below), which sets forth a period of time in which the ET tube should be properly positioned. If the procedure timer expires and the ET tube is not properly placed, then the patient is at risk of desaturation due to depletion of the oxygen reservoir within the lungs of the patient.

Figure 10A:
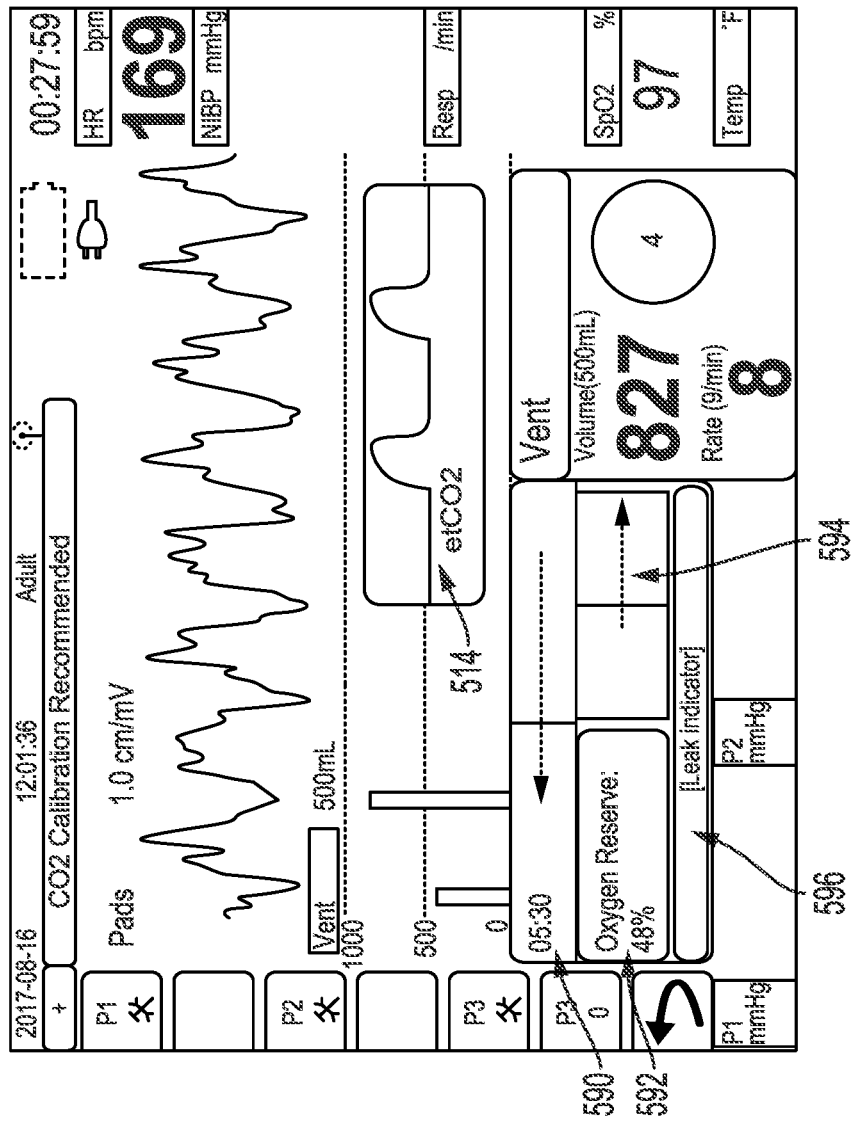
FIG. 10A is an exemplary user interface displayed on a medical device during the preparation of a patient for rapid sequence intubation showing an alarm indication in accordance with an embodiment.

FIG. 10A is an exemplary user interface displayed on the medical device 202 during the preparation of the patient for rapid sequence intubation. The illustrated embodiment displays a preoxygenation timer 590 and an oxygen reserve indicator 592. Preoxygenation timer 590 provides a numerical timer and/or a visual indicator of how much time remains (e.g., the bar slowly drain in accordance with remaining time. Similarly, the oxygen reserve indicator (ORi) which provides an estimation of "how full" the patient oxygen reserve is. The oxygen reserve indicator may provide a numerical value and/or a progress bar 594. As discussed above, this information may be based on expiratory flow measured by the airway sensor(s) 221. Lastly, the dashboard may include a leakage alarm 596, which will display a message in response to the detected leak. Additionally, the medical device 202 may be programmed to provide distinctive audio tones upon, e.g., expiration of the preoxygenation timer 590 or fulfilling of the capacity determined by ORi 592.

Figure 10B:
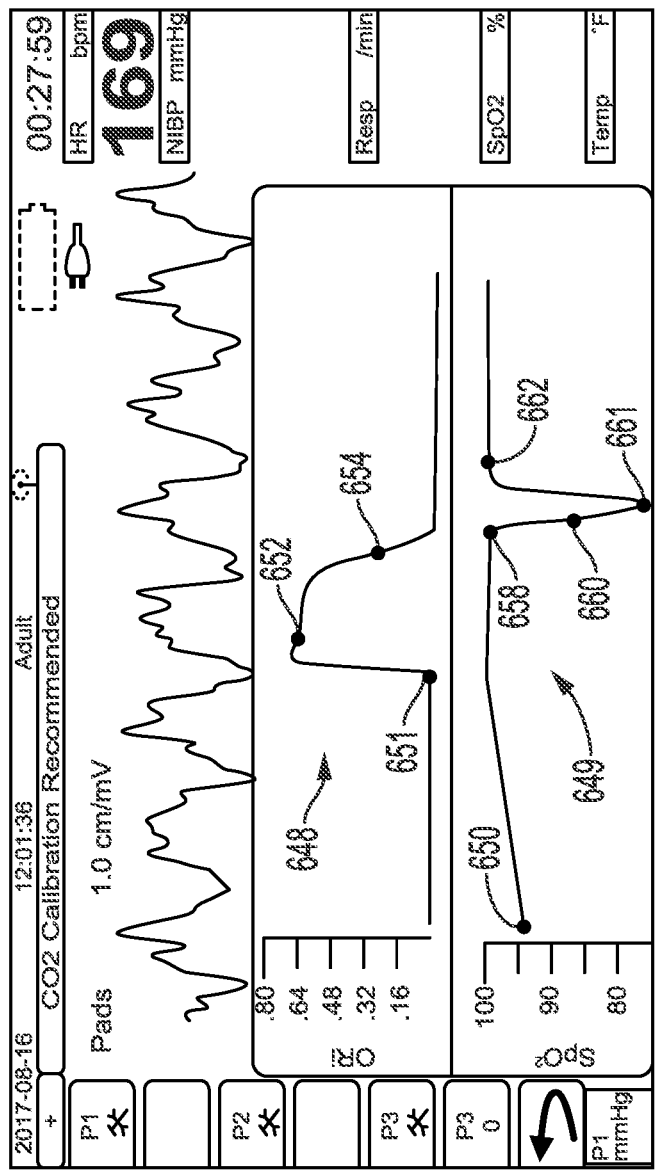
FIG. 10B is an additional exemplary user interface displayed on a medical device during an intubation procedure in accordance with an embodiment.

FIG. 10B is an additional exemplary user interface that may be displayed on the medical device 202 during the intubation procedure. In the illustrated example, the display 504 of the medical device 202 displays an oxygen reserve indicator (ORi) 648, which is an intubation parameter that provides information on the amount of oxygen reserve a patient has during the intubation procedure. Additionally, the medical device 202 further provides a visual representation of SpO2 649. In one example, the ORi is a unit-less scale between 0.00 and 1.00 (where 1 is full oxygen reserve and 0 is an empty reserve).

Each of the points represents a step (or event) that occurs during intubation. For example, point 650 represents the point at which the patient 102 begins receiving manual ventilation and oxygen. As shown in the figure, the patient's SpO2 starts off around 95% and slowly begins to climb toward 100%. Then, at point 651, the patient begins the preoxygenation step and the oxygen reserve begins to fill. Point 652, shows the point at which preoxygenation was completed and oxygen reserve begins to deplete (e.g., the rescuers have begun the intubation process and are no longer providing ventilation). As illustrated, the decline generally starts slowly, and then begins to descend rapidly. Point 654 represents when an alarm would be activated. As the oxygen reserve depletes, the SpO2 also begins to decline. Point 658 illustrates a point at which the SpO2 begins to decline and Point 660 represents the point at which an SpO2 threshold is passed (e.g., between 88 to 92%). Point 661 represent a point at which the intubation should be completed (or aborted) and the rescuers 104, 106 began ventilating and providing oxygen to the patient to correct the hypoxemia. Lastly, point 662, represents the point at which the patient is back SpO2 is back to normal levels (e.g., approximately 94%).

An example of a device capable of measuring SpO2 and calculating the oxygen reserve index is the Radical 7, Rainbow SET (Signal Extraction Technology) by Masimo from Irvine, California.

Figure 11:
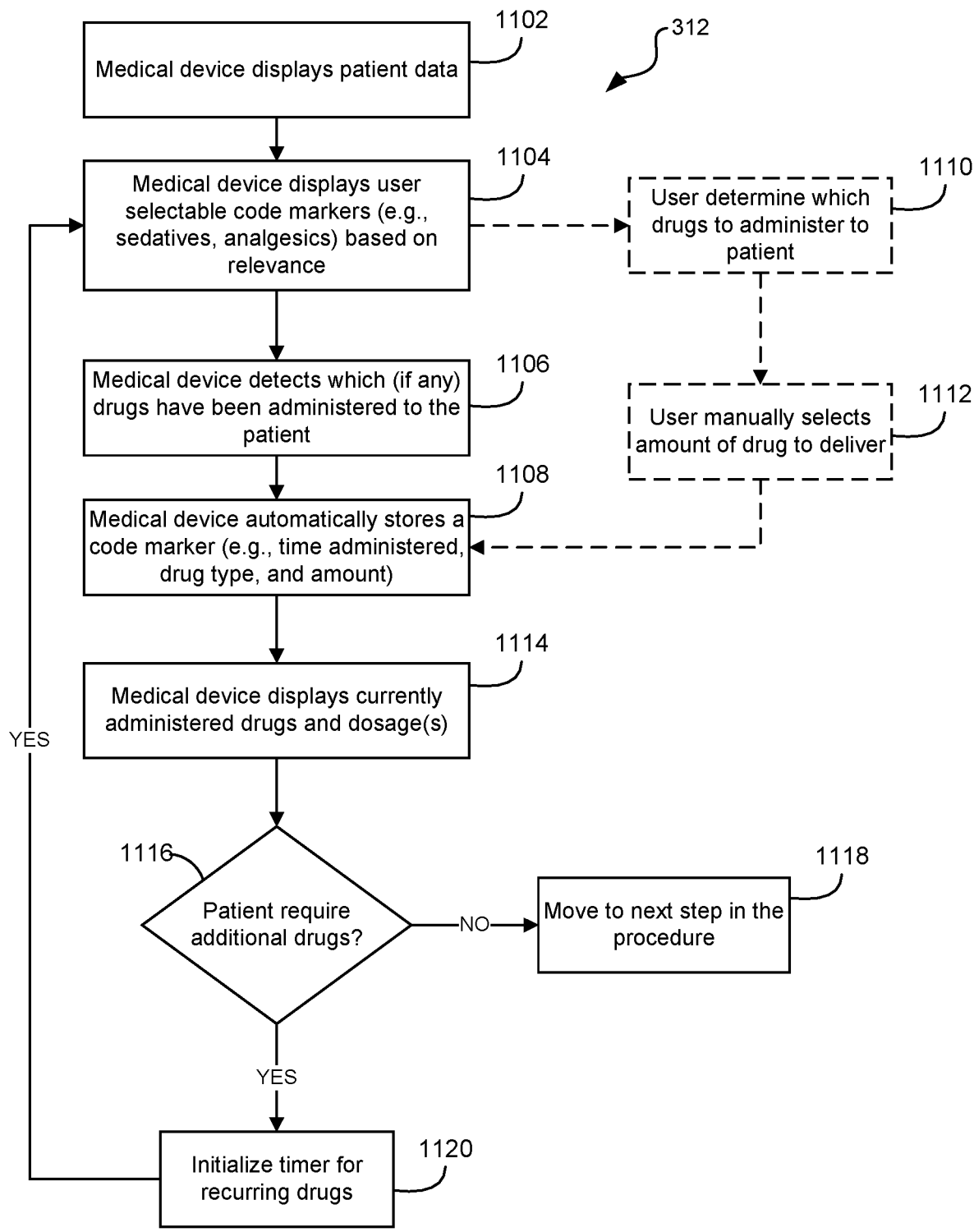
FIG. 11 is a flow chart illustrating steps performed during the pre-treatment and paralysis of a patient during a rapid sequence intubation procedure in accordance with an embodiment.

FIG. 11 is a flow chart illustrating typical steps performed during the pretreatment (e.g., sedation) and paralysis of the patient 102 during the rapid sequence intubation procedure in accordance with embodiments of the present disclosure.

In the first step 1102, the medical device 202 displays patient data in the display 504. In the next step 1104, the medical device 202 displays user selectable event or code markers (e.g., sedatives, analgesics) based on relevance to the current step in the procedure. The code markers provide a record of which drugs were administered to the patient and the time, date and route of delivery. Once a relevant code marker is selected, this information is saved in the memory of the medical device and is retrievable for later analysis or documentation of the drugs and treatments provided to the patient during the rescue. In certain embodiments, the rescuer may provide a manual input (e.g., voice input, touchscreen, keypad, buttons/softkeys, external computing device, etc.) to select the particular code marker. In other embodiments, the medical device may be provided with an indication that a particular drug has been administered, and so a code marker may be recorded. For example, as discussed below, the medical device may scan a bar code or detect an RFID associated with a particular drug to be administered and may log the code marker at that time.

In an alternative embodiment, the rescuers may have considerable experience and are extremely proficient in rapid sequence intubation. In this scenario, the rescuer may override suggestions provided by the medical device (e.g., via user input), and the rescuer may determine which drugs to administer to the patient 102 in step 1110. Similarly, in step 1112, the rescuer manually selects amount of drugs to deliver.

Returning to step 1106, the medical device 202 detects which (if any) drugs have been administered to the patient (e.g., via manual input, bar code scan to confirm the type and amount of drug for administration) and the automatically stores a code marker (e.g., time administered, drug type, and amount) to memory in step 1108. In one embodiment, each syringe includes a barcode or radio frequency identification (RFID) chip, for example and the medical device includes a corresponding barcode reader. The rescuer(s) 104, 106 scan the syringe prior to administration and the medical device stores a record of which medication was given along with a time and date stamp.

In step 1114, the medical device displays currently administered drugs and dosage(s) to enable the rescuer to view which drugs were administered. In the next step 1116, the medical device determines if the patient requires additional administrations of the drug. If the patient requires additional administration of the drug, then the medical device 202 initializes a timer in step 1120 to provide an indication to the rescuer of when recurring medication needs to be administered. If the patient does not require additional medications (e.g., the patient is properly sedated), then the medical device 202 moves to the next step in the procedure in step 1118.

Figure 12:
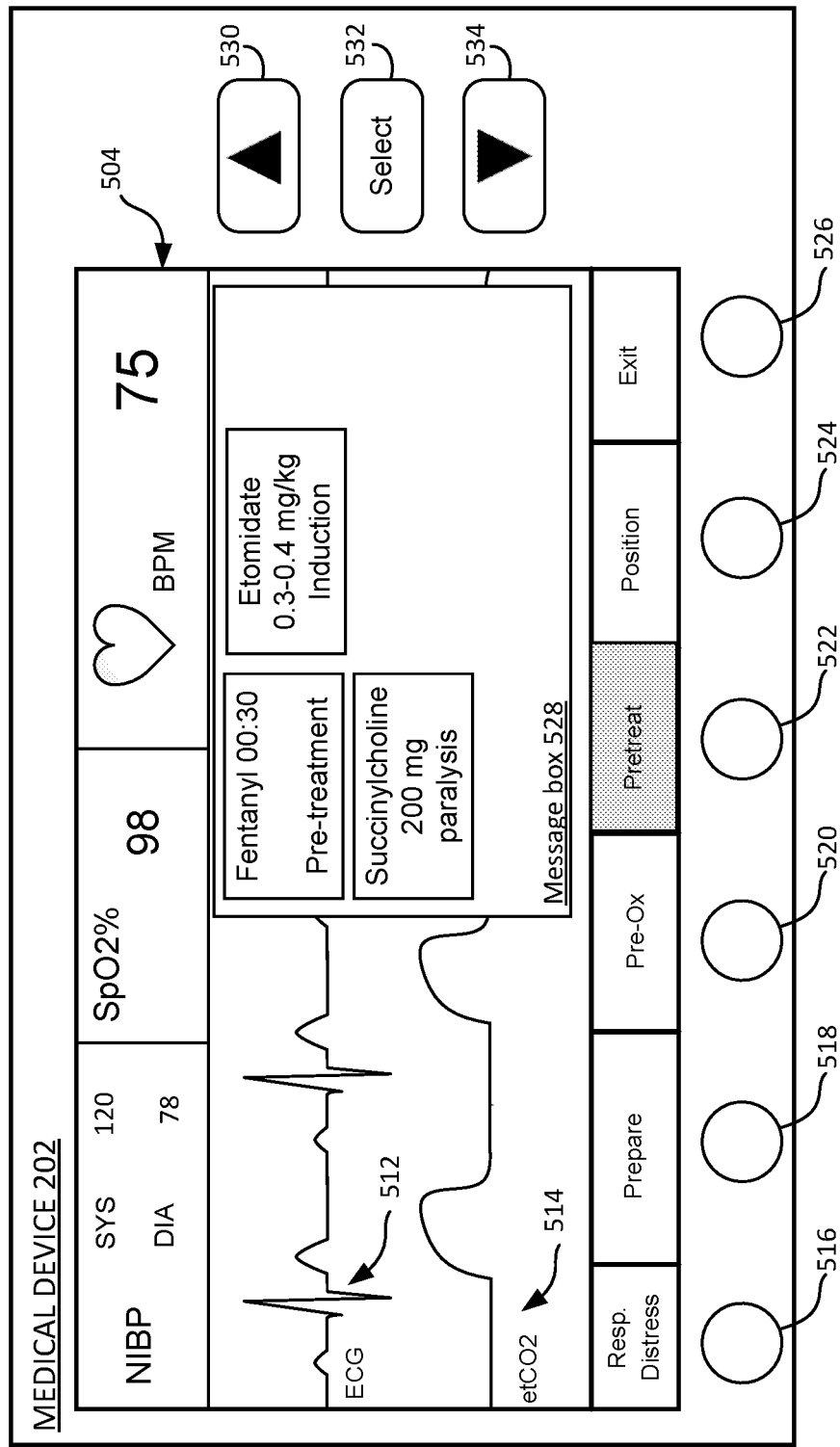
FIG. 12 is an exemplary user interface displayed on a medical device during the preparation of a patient for rapid sequence intubation in accordance with an embodiment.

FIG. 12 is an exemplary user interface displayed on the medical device during the preparation of the patient for rapid sequence intubation. In the illustrated example, code marker information associated with drug administration is presented in message box 528. As detailed previously, the dosage information could be the specific amount (based on the patient's height, weight and/or gender) or just the dosage range.

Figure 13:
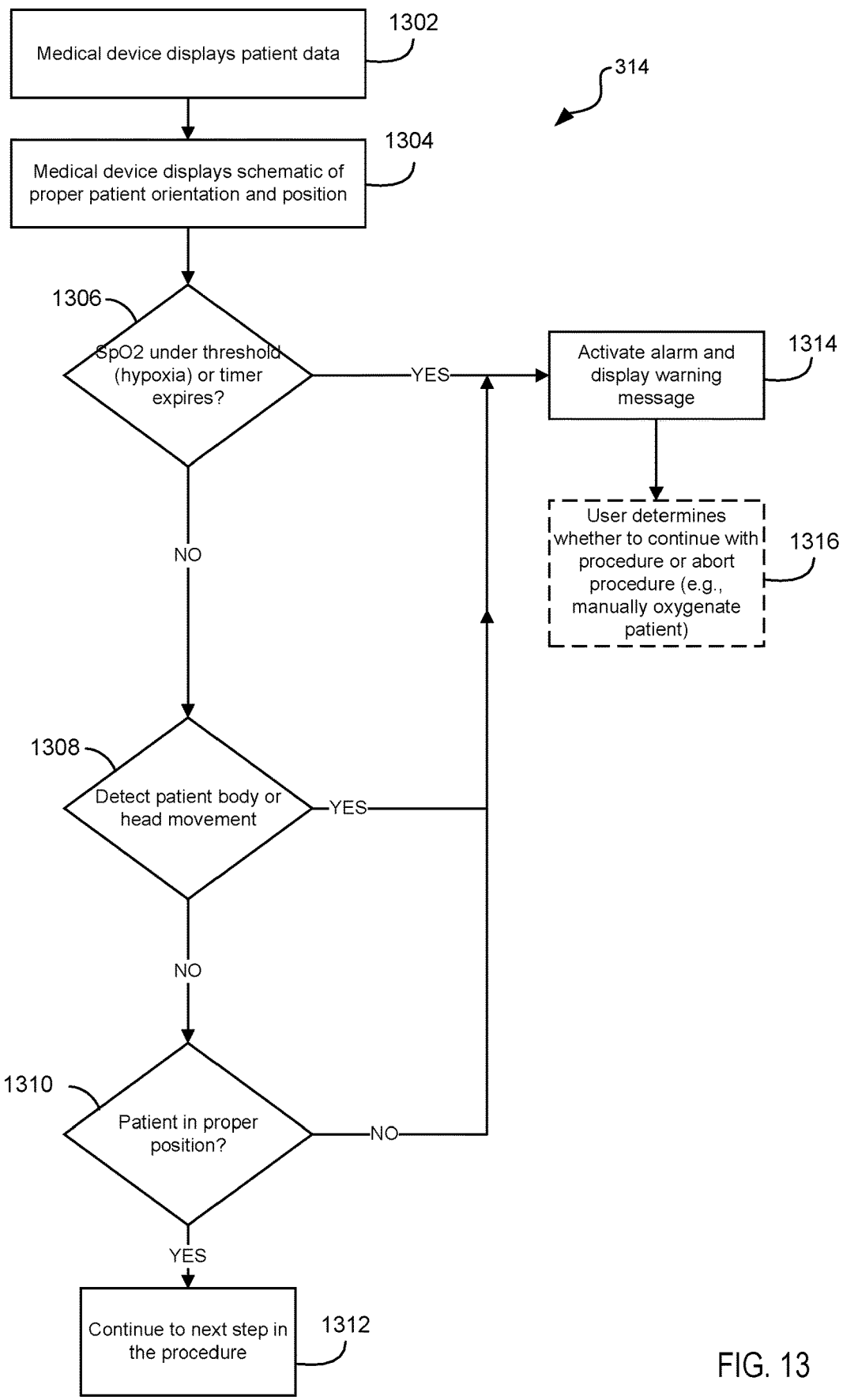
FIG. 13 is a flow chart illustrating steps performed during the patient position steps of the rapid sequence intubation procedure in accordance with an embodiment.

FIG. 13 is a flow chart illustrating typical steps performed during the patient positioning steps of the rapid sequence intubation procedure in accordance with embodiments presented herein.

First, in step 1302, the medical device 202 displays patient data in the display 504. In the next step 1304, the medical device 202 displays a schematic of proper patient orientation and position to perform the intubation or an alternative based on the patient information, e.g. weight, height and sex. In the next step 1306, the medical device 202 determines if the SpO2 is under the threshold (e.g., hypoxemia) or if the timer has expired. If the patient is hypoxemic or the procedure timer has expired, then the medical device 202 activates an alarm and displays a warning on the display 504 in step 1314. In some embodiments, an alarm/notification may be provided before the patient becomes hypoxemic, e.g., when the SpO2 falls below a threshold (e.g., 90 to 92%) that is typically higher than that which would be considered hypoxemic, indicating that the patient is at risk of desaturation. The apneic period after preoxygenation, during intubation is particularly sensitive because the only source of oxygen for the patient's tissues is coming from the oxygen reservoir built up in the lungs. As a result, the medical device 202 times the apneic period and provides a time-based alarm if the user exceeds the time prescribed by the local medical guidance (e.g. 30 to 60 seconds). Similarly, in step 1308 the medical device 202 detects if the patient's body or head movement has moved the patient out of proper positioning. In one embodiment, the medical device 202 includes one or more cameras (not shown) and implements image analysis processing to identify features (head, torso, arms) of the patient to guide position of the body. In another embodiment, motion sensors are placed on the patient's torso and record patient movements (e.g., 12 ECG leads, which are placed on the patient's body may further include position sensors to measure relative positions and identify the position of the patient).

In yet another alternative embodiment, the medical device 202 simply displays an image of proper position (e.g., the sniffing position) and how to align the body, for the rescuer to compare proper positioning with actual positioning of the body. Likewise, the medical device 202 is able to display a variety of images based on the previously entered height, weight, age and gender information. The images may be displayed for a preset period of time, or until the rescuers indicate that positioning has been completed.

If the patient's head or body moves in a way that brings the patient out of a suitable position for intubation, then the medical device 202 may activate an alarm and display a warning in step 1314. Generally, after an alarm, the rescuers 104, 106 will make a determination of whether to continue with the procedure (e.g., complete intubation) or whether to abort the procedure and, e.g., manually ventilate and oxygenate the patient 102 in step 1316.

Lastly, in step 1310, the medical device 202 determines if the patient 102 is in proper position to begin intubation, for example, via image/video information captured by cameras incorporated in or otherwise associated with the medical device, and/or motion or positioning information provided by motion sensors on the patient body. Alternatively, using data from the patient liter or stretcher that provides patient position information. If the patient 102 is in proper position (e.g. "sniffing" position or "RAMP" position), then the medical device 202 continues to the next step in the intubation procedure in step 1312. If, the patient is not in proper position, then the medical device 202 displays the warning from step 1314. In an alternative embodiment, the medical device 202 may also be able to aid the rescuer in positioning. For example, the medical device 202 may be able to provide visual or audible feedback to guide the position of the patient into correct position for the intubation.

Typically, each warning is specific to the issue detected (e.g., SpO2, timer expired, head movement, etc.). Additionally, the medical device 202 will typically provide suggestions for how to correct the issue, rather than presenting binary choices of aborting the procedure or continuing despite the warning.

Alternatively, in another embodiment, the warning is a general warning that is not specific the identified issues. While the illustrated embodiment depicts the warning being displayed visually to the rescuer via the display 504, the warnings could also be audible warnings generated from, e.g., speakers of the medical device 202.

Figure 14A:
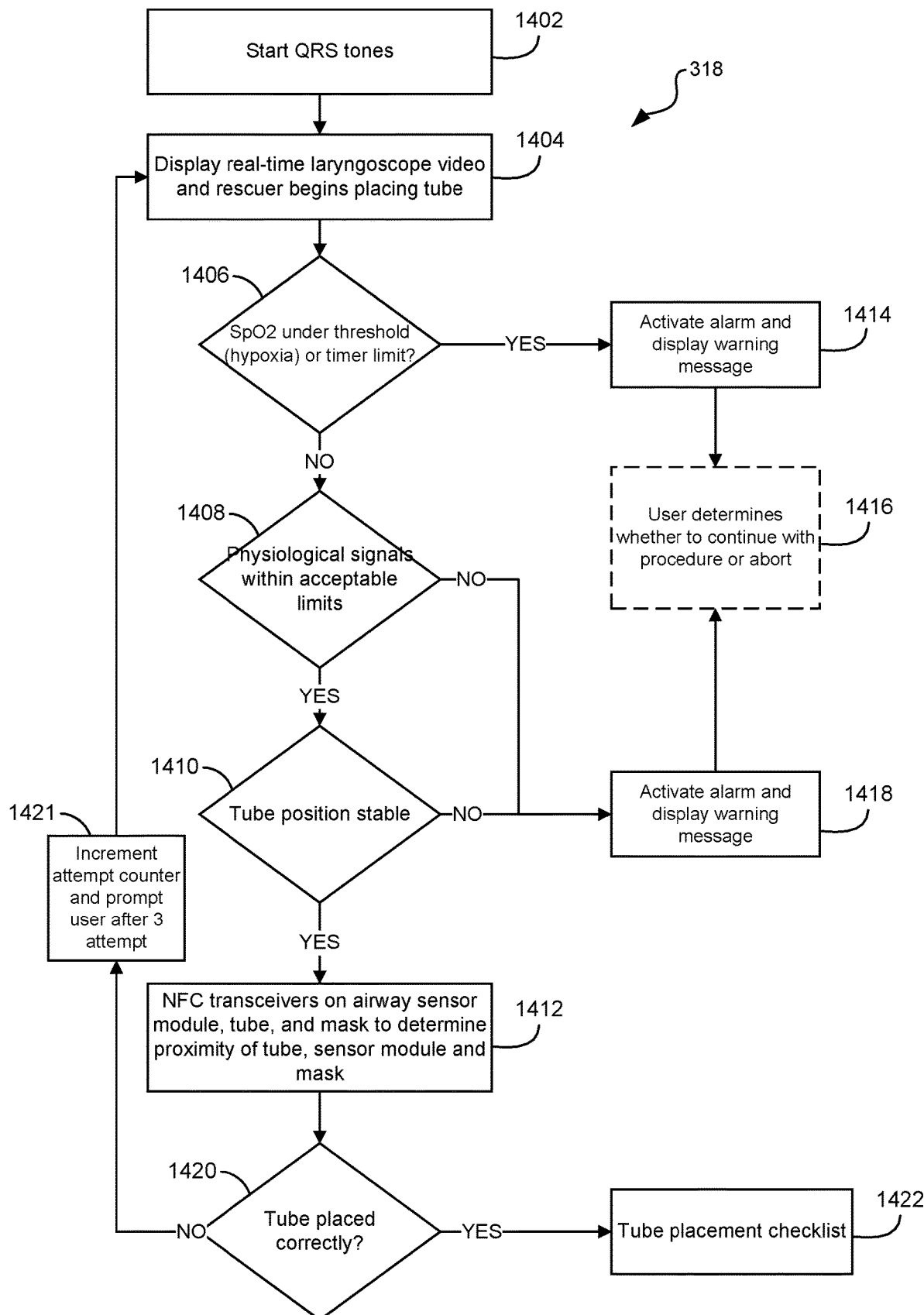
FIG. 14A is a flow chart illustrating steps performed during the placement of an endotracheal tube during a rapid sequence intubation procedure in accordance with an embodiment.

FIG. 14A is a flow chart illustrating typical steps performed during the placement of the endotracheal tube during a rapid sequence intubation procedure, or other intubation procedure, in accordance with embodiments described herein.

To verify that the intubation tube is properly placed, or remains properly placed, the medical device may employ various criteria, examples of which are described in more detail further below. In general, such criteria may be predetermined, set as default, or otherwise preconfigured in the medical device, or in some cases, a user may simply provide an input to the medical device as verification that the tube has been properly placed or remains in place. Alternatively, the medical device may employ various sensors and appropriate predetermined criteria to verify proper placement of the ET tube. Such criteria may be applicable for when the intubation tube is initially placed and/or when the intubation tube is already placed and the patient is continuously being monitored for any conditions that require an alert (e.g., intubation tube dislodgement). In some cases, the criteria may differ depending on whether the tube is initially being placed, or whether the patient is being monitored for possible tube dislodgement. Described further below, the predetermined criteria may involve various thresholds, timers, ranges, averages, and/or baselines that are utilized by the medical device to determine if, or when, physiological parameters are within acceptable operating parameters. Various examples of criteria, which are generally described as thresholds, ranges, timers, and baselines, are non-limiting, and other types of predetermined criteria may also be implemented.

In step 1402, the medical device 202 may optionally play (audibly) tones that convey SpO2 information in accordance with QRS pulses, with the frequency of the tones varying based on the SpO2 saturation. For instance, the medical device may track QRS complexes in the ECG and emit a tone corresponding to each QRS peak. The frequency of the tone may be higher or lower depending on the particular level of oxygen saturation detected, such as SpO2 level. For example, in such a configuration, as the oxygen saturation level decreases, the associated tone(s) played when the QRS complex is detected goes lower in frequency until the alarm threshold is reached, which would trigger an alarm. In one embodiment, the threshold level is a user-configurable parameter that is programmed into the device prior to being deployed for use. Additionally, or alternatively, the medical device is pre-configured with default threshold values (e.g., between 85-88%, between 85-93%, between 85-91%, between 88-91%). As discussed above, the threshold values during this step in the overall procedure may be set higher (e.g., 91% during intubation) than would normally be the case during regular monitoring (e.g., 88% during monitoring post-intubation) because of the elevated risk of desaturation at this stage. In yet another embodiment, the medical device 202 includes an option to silence the alarm if, for example, the threshold is not able to be exceeded even with ventilation and oxygenation.

Or, if the oxygen saturation level maintains a consistent level, the associated tone(s) played with the pulse/QRS peak with remain about the same frequency. As a result, the rescuer will be able to obtain an audible indication of the patient's oxygen saturation at regular intervals, according to the heart beat of the patient.

In the next step 1404, the medical device displays a real-time laryngoscope video as the rescuer begins placing the endotracheal tube. In the next step 1406, as the ET tube is being placed, the medical device 202 continues to monitor patient vitals, in particular, to track any potential risk of desaturation, due to depletion of the oxygen reservoir. For instance, during the procedure, the medical device 202 determines if the SpO2 is under the threshold (hypoxemia) or if the procedure timer has expired. If the SpO2 is under the threshold or the procedure timer has expired, then the medical device 202 activates an alarm and displays a warning message to the rescuers in step 1414. The rescuers must then determine whether to continue with the procedure or abort the procedure in step 1416. If the SpO2 is not under the threshold and the procedure timer is not yet expired, then the medical device continues to determine if the physiological or airway gas measurement signals are within acceptable limits in step 1408.

If the physiological or airway gas measurement signals are not within acceptable limits, then the medical device 202 activates an alarm and displays the warning message in step 1418. If the physiological or airway gas measurement signals are within acceptable limits, then the medical device 202 determines if the tube placement is stable in step 1410. If there is unwanted movement, then the medical device 202 activates an alarm and displays the warning message in step 1418. For example, as provided above with respect to step 1406, if the SpO2 is outside of acceptable limits, then an alarm and/or warning notification may be provided. As discussed, this alarm may be triggered if oxygen saturation levels fall below a particular threshold. In some case, the medical device may be configured such that the further the oxygen saturation is below the set threshold, the more intense the alarm and/or notification (e.g., louder audible sound, stronger haptic vibration, flashing visual with optional color change in the visual display, colored highlighting of a box on the display to yellow or red depending on the severity of the alarm with yellow indicating a warning and red being more severe than yellow).

In certain embodiments, this alarm may be triggered if oxygen saturation levels exhibit a dramatic downward trend. For instance, if the SpO2 levels falls from 95% to 90% within a short time period (e.g., within 5-10 seconds), then the medical device 202 may make a determination that the patient is at risk of desaturation and may then trigger an alarm or warning notification. Or, if the oxygen saturation levels exhibit a significant drop (e.g., 5-10%) over the course of the overall procedure from a generally constant baseline, then the medical device may also determine that the patient is at risk of desaturation, and so trigger the alarm/notification. As an example, after preoxygenation, the patient's oxygen saturation levels may remain relatively high, e.g., 97%, and a baseline may be established. Then after a period of time (relatively long or short), if the oxygen saturation level drops from 97% to 91%, then the medical device may trigger an alarm/notification of a risk of desaturation. In this case, while 91% may be within an acceptable threshold for the general population, such a significant drop in oxygen saturation from a relatively high initial level may be cause for concern that the tissues of the patient are not receiving typically accustomed amounts of oxygen for healthy function.

The alarm thresholds of the medical device may be configurable by a user, for example, prior to use in an emergency. For example, an alarm and/or notification threshold may be 88%, 89%, 90%, 91%, 92%, 93%, or another appropriate value given the use scenario (e.g., local medical guidance). In certain embodiments, the alarm/notification thresholds may differ depending on whether the medical device is being used in an active intubation mode (e.g., intubation process is happening), which may be distinct from a monitoring mode (e.g., tube has already been placed and the patient is being monitored for high risk events such as sudden desaturation, swings in blood pressure or heart rate, etc.). As discussed above, the patient may be at higher risk of desaturation when being actively intubated as compared to when the tube has already been placed. Accordingly, the trigger(s) for a desaturation alarm/notification may be more sensitive during placement of the tube than during a post-intubation monitoring state. The medical device may further be able to allow the rescuer to silence the alarm(s)/notification(s) if desired (e.g., oxygen saturation levels remain relatively low during preoxygenation, yet desaturation has not yet occurred).

In some embodiments, one or more of the airway sensors (e.g., flow sensor) and the ET tube may be outfitted with near-field communication (NFC) transceivers, to detect whether they are in close proximity. When the ET tube is placed, the mask may be removed from the patient, but the airway flow sensor may still remain in the patient airway so as to provide airway gas measurements. If the tube placement is stable, then NFC transceivers on the airflow sensor module and the ET tube may be used to provide an indication to the medical device that they have been assembled and are being used to deliver oxygen to the patient. Accordingly, the indication that the airway flow sensor and the ET tube are placed in and remain in close proximity for an extended period of time (e.g., 1 to 5 minutes), e.g., as confirmed by NFC sensor detection there between, may be used by the medical device to determine whether the ET tube has been placed in an appropriate position relative to the patient.

In the next step 1420, the medical device 202 determines if the tube is placed. Typically, this is accomplished by analyzing the data from the sensors such as the flow sensor, and capnography sensor to ensure that gas is flowing at appropriate rates/volumes in the patient airway, and verify ETCO2 waveforms (e.g., normal waveform returns, indicating that inspiratory and expiratory flows have returned), which indicate that the intubation procedure was successfully completed. In one embodiment, the medical device 202 identifies proper placement when ETCO2 is below 45 mmHg, when the ETCO2 waveform has the correct size, rate, and amplitude, and the oxygen and/or flow sensors are measuring 400 mL in inspiratory and expiratory flow. In various embodiments, oxygen saturation levels (e.g., from SpO2) are also provided to verify intubation tube placement. While oxygen saturation levels may be relatively delayed due to physiological processes, such measurements will be provided during post-intubation monitoring of the patient. Though, flow sensor measurements of flow rate and volume in the patient airway may be used by the medical device (e.g., confirming a minimum level of flow there through) for verifying intubation tube placement. Additionally, impedance measurements coupled with auscultation may be another way to verify ET tube placement. In this method, measurements of changes in transthoracic impedance are used to verify that air is entering the lungs via the trachea, as opposed to entering the stomach via the esophagus.

In addition, the medical device 202 could use image processing to analyze data from the video laryngoscope to determine if, for example, the ETT passed between the vocal cords. If the tube was not placed properly, then the device returns to the step 1404 and the rescuer needs to begin placing the tube again.

In the next step 1421, the medical device 202 maintains a failed attempt counter, which keeps tracks of the number of failed attempts. This counter serves multiple purposes. For example, after a first failed attempt the medical device prompts the rescuers re-check previous steps such as evaluate bodily fluids in the airway, patient positioning, change of user, laryngoscope blade change, and/or use of a bougie or mucosal airway tool. Prehospital data demonstrates, addressing these issues before the second intubation attempt significantly increases the probability of 2nd attempt success. Accordingly, if the first intubation attempt was unsuccessful, a more senior rescuer may then be chosen to perform the second intubation attempt. Then, after a third failed attempt, or a subsequent failed attempt as determined by the device configuration, the medical device prompts or otherwise suggests that the rescuers use an alternative supraglottic airway as an alternative to an ETT.

If, the tube was placed correctly, then the medical device moves to the tube placement checklist in step 1422.

Figure 14B:
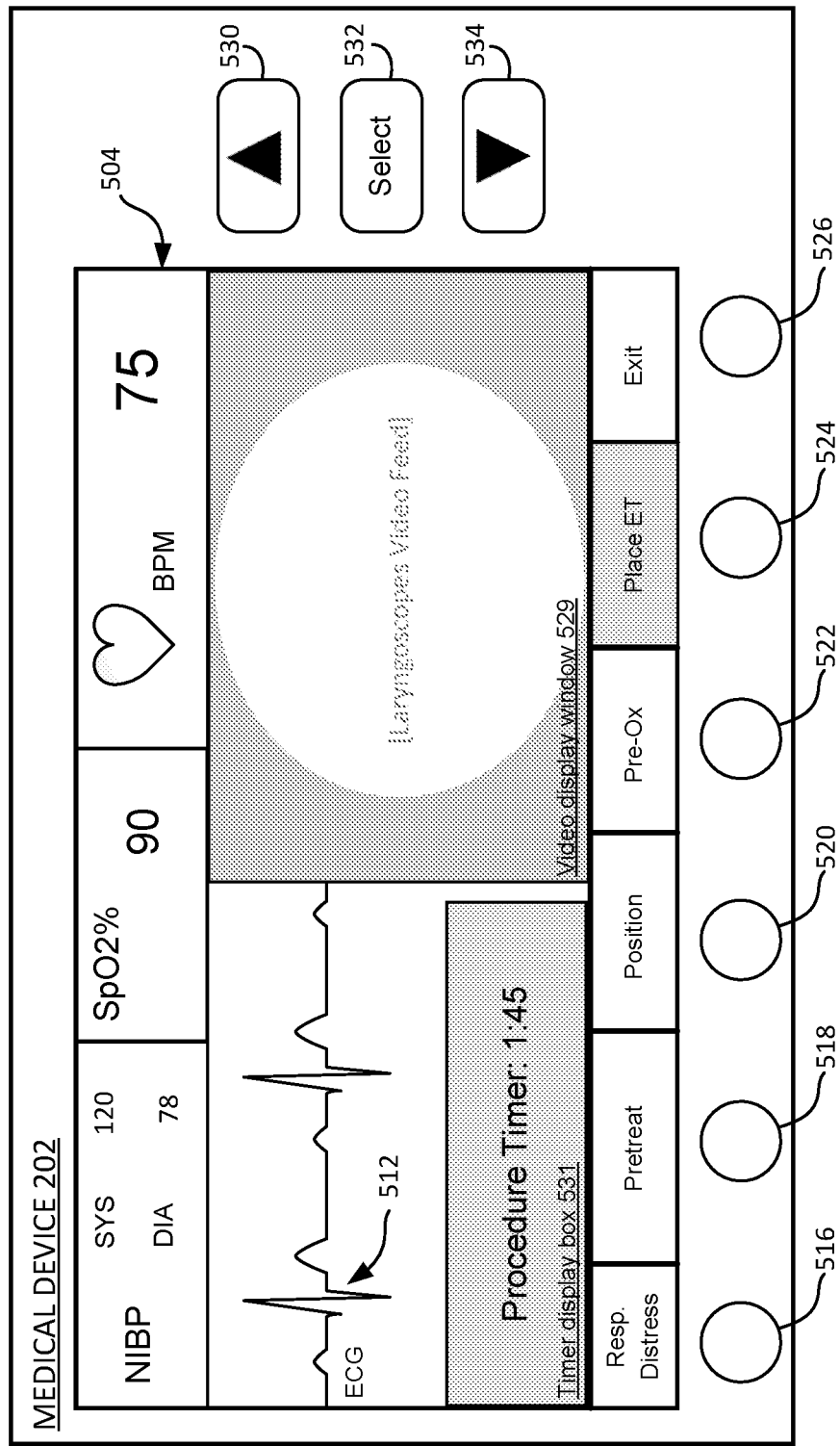
FIG. 14B is an exemplary user interface displayed on a medical device during the tube placement of a rapid sequence intubation procedure.

FIG. 14B is an exemplary user interface displayed on the medical device 202 during the endotracheal tube placement procedure.

In the example embodiment illustrated, key information such as NIBP, SpO2, heart rate, and the procedure timer 531 are displayed. As discussed herein, this procedure timer provides a countdown (e.g., from 3 to 8 minutes, depending on how the procedure timer feature is configured) indicating how long the rescuers have to preoxygenate before performing intubation. For instance, and as discussed herein, if the procedure timer expires, then the medical device 202 may generate an alarm or warning message to the rescuer that the timer has expired, prompting the rescuer to consider whether to continue forward with the procedure, go back to the preoxygenation stage, or perform another task. Additionally, if the rescuer uses a laryngoscope, a real-time video feed from the laryngoscope is displayed 529. In the illustrated embodiment, the video feed is only displayed on half of the display 504. In alternative embodiments, the video feed may cover the entirety of the display 504 or an even smaller portion of the display in other embodiments. In still yet other embodiments, the video feed may be transmitted to another device entirely (not pictured), such as a second medical device 202, a tablet, or a remote medical monitoring and guidance location, for example.

FIGS. 15A-15G illustrate several embodiments that may be implemented in verifying tube placement. Specifically, these figures illustrate examples of tube placement verification using capnography sensors to measure ETCO2 or lead/pad to measure transthoracic impedance.

Figure 15A:
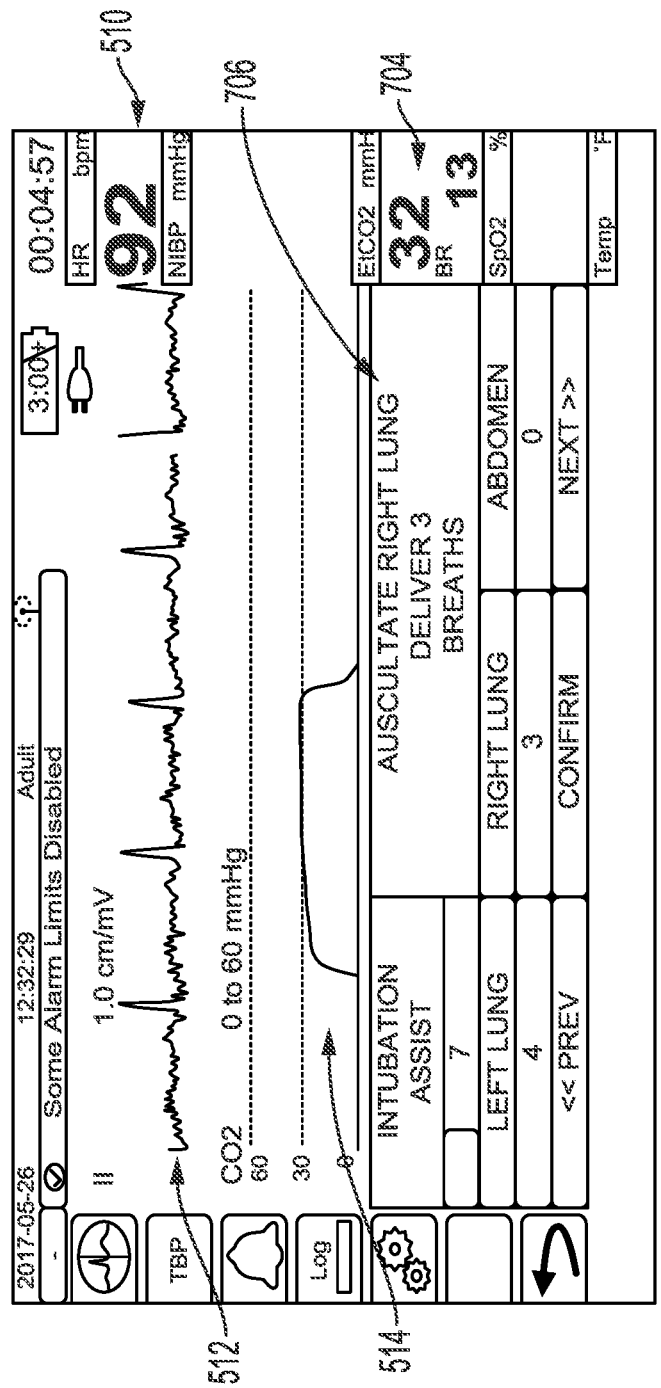
FIG. 15A is an exemplary user interface displayed on a medical device during the tube placement of a rapid sequence intubation procedure.

FIG. 15A is an exemplary user interface (dashboard) displayed on the medical device during the tube placement of an intubation procedure. The display includes specific prompts 706 directly related to specific steps being performed during the intubation using a combination of impedance measurements and auscultation by the rescuer to determine whether the ET tube has been correctly placed. Examples of this overall procedure for verifying ET tube placement are described in U.S. Patent Publication 2014/0180138, filed on Dec. 17, 2013, entitled "Ventilation Monitoring," which is hereby incorporated by reference in its entirety. Additionally, the illustrated example displays other relevant information such as ECG 512, ETCO2 waveform, 514 heart rate window 510, ETCO2 window 704, which shows the ETCO2 value (e.g., 32 mmHg). In general, auscultation may include manual listening of sounds from the heart, lungs, or other organs, typically with a stethoscope, or may involve other methods such as acoustic cardiography performed by a device such as an Audicor® RT 4.0 AM sensor manufactured by Inovise Medical, Inc. of Portland, Oreg. to determine breath sounds or in some cases, a lack thereof. The acoustic sensors can include an accelerometer, microphone, or other additional sensors. The acoustic sensors are configured to detect and convey acoustic signals, such as those created by activity (e.g., movement) of the lungs or stomach of the patient. In some implementations, the acoustic sensor can comprise a three axis multiple-channel MEMS accelerometer. The acoustic sensor may comprise a three-channel accelerometer. In some implementations, a first channel of the three-channel accelerometer is configured to monitor sounds produced by a heart of the patient, a second channel of the three-channel accelerometer is configured to monitor a respiration of the patient, and a third channel of the three-channel accelerometer is configured to monitor movement of the patient. The acoustic three-channel accelerometer can be configured to sense movement in each of three orthogonal axes. An example of an accelerometer which may be utilized in some implementations is a LIS344ALH accelerometer, available from STMicroelectronics.

In some implementations the acoustic sensor comprises a microphone. The acoustic sensor and associated electronics may be configured to monitor any one or more of a patient's respiration, a patient's heart sounds, a patient's position, and an activity level of a patient. The acoustic sensor and associated electronics may additionally or alternatively be configured to monitor other sounds which may be indicative of a state of health of a patient, for example, gastrointestinal sounds or the sounds of snoring or the absence of such sounds, for example, to provide an indication of the patient experiencing sleep apnea. The acoustic sensor may provide signals indicative of the patient's respiration on a first channel, signals indicative of the patient's heart sounds on a second channel, and signals indicative of the patient's position on a third channel. In other implementations, the different channels may be utilized to provide signals indicative of more than one physiological parameter or other parameter associated with the state of the patient. For example, in one implementation, the acoustic sensor may provide signals indicative of the patient's heart sounds on a first channel, signals indicative of the patient's respiration (lung sounds) on a second channel, and signals indicative of the patient's body position on any or all of the first, second, and third channel. It should be appreciated that dependent on the underlying parameter that is being monitored, multiple signals related to the parameter being monitored may be received over a single channel or a number of different channels.

Spectral components of lung and stomach sounds can vary vastly in regard to placement of the intubation tube. A signal processing unit may compare spectral components of acoustic signals measured by the acoustic sensor(s) with spectral components of lung and esophageal sounds having a particular spectral pattern. For example, the sound of aspirating lungs can be of a higher frequency than spectral components of stomach noises. Accordingly, the signal processing unit may compare spectral components of the acoustic signal(s) with a predetermined threshold to determine placement of the intubation tube in the trachea. The predetermined threshold can be indicative of the discrepancy in lung and esophageal spectral components. In some implementations, if the spectral pattern involves spectral components exhibiting a frequency component above the predetermined threshold, the signal processing unit can indicate to an operator of the system (e.g., a clinician) that the intubation tube has been properly placed in the trachea. In some implementations, if the spectral pattern exhibits spectral components frequency characteristics falling below the predetermined threshold, the signal processing unit indicates or conveys an alert that the intubation tube has been improperly placed in the esophagus. Proper placement of the intubation tube can occur if the intubation tube is placed in a position such that the intubation tube is effective (e.g., positioned according to design specifications). In some implementations, the predetermined threshold can be determined based on patient age, gender, height, weight, and/or physical condition. In some implementations, the threshold value can be a discrete value. In some implementations, the threshold value can include a range of frequencies. In some embodiments, an acoustic sensor may be used in combination with an airflow sensor, to verify that a positive pressure ventilation breath has reached the lungs. For example, the medical device may receive data indicative of the airflow in the patient's airway from the airflow sensor to determine that a positive pressure breath has been given. And then the medical device may receive and process the acoustic information regarding the airflow in the patient's lungs via the acoustic sensor(s) placed on the patient. In some embodiments, a physiological baseline regarding airflow in the patient's lungs after initial placement of the ET tube may be determined according to the received acoustic information, having a distinguishable spectral pattern with spectral components. The medical may then determine whether the ET tube is or remains properly placed based on a deviation from the determined physiological baseline, and present on a user interface an output of that determination of whether the ET tube is or remains properly placed. The determined baseline may be an initial baseline that is determined when the ET tube is initially placed, or the baseline may be a dynamic baseline that is continually updated (e.g., moving average of spectral components that are continuously being monitored) as the tube remains in position and more ventilation readings are taken. The initial baseline may include an average of initial spectral components received upon initial placement of the tube. When the medical device detects a substantial deviation from the physiological baseline (initial and/or dynamic), such as a percentage difference between a current spectral pattern and the initial and/or dynamic baseline, then an alert may be given that the tube may be dislodged.

Examples of systems and methods that may be used to assist caregivers in verifying that an intubation tube has been and/or remains properly placed using an acoustic sensor are described in U.S. Pat. No. 9,826,956, entitled "System and methods for positioning an intubation tube," which is hereby incorporated by reference in its entirety. Various examples of interfaces for providing assistance to a user in placing the intubation tube including necessary auscultation steps are provided below.

Figure 15B:
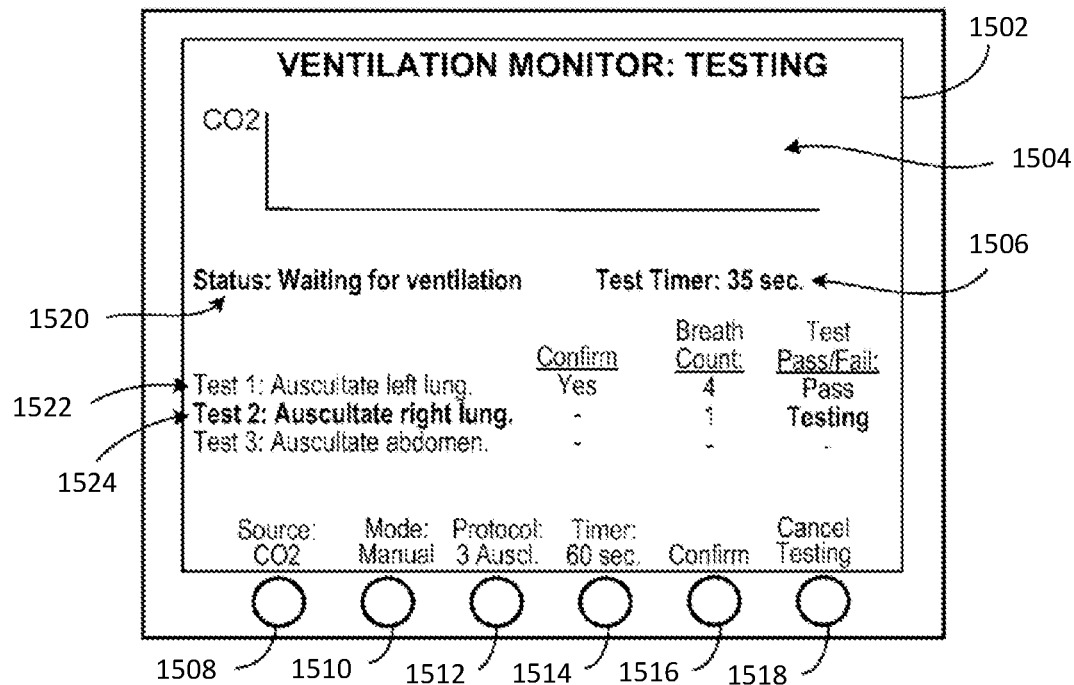
FIG. 15B is a diagram of a testing screen of a medical device showing testing in progress, the medical device is configured in a manual mode for use with a capnography sensor and a protocol comprising three auscultations according to an example embodiment.

FIG. 15B is a diagram of a testing screen 1502 of the medical device 202 showing testing in progress, the medical device 202 configured in a manual mode for use with capnography sensor 218 and a protocol comprising three auscultations according to an example embodiment. In the embodiment, the source is configured to "CO2" using soft key 1508, which means that only the capnography sensor 218 of FIG. 2 will be used as an automated means to detect the subject's breath. Manual mode, which requires the user to confirm a positive result of each auscultation performed using soft key 1516, is configured by the user using soft key 1510. The 3-auscultation protocol, which includes user auscultations of the left lung, right lung and abdomen, is configured by the user using soft key 1512. At any point, the testing may be canceled by using soft key 1518.

In the embodiment, since the capnography sensor 218 is being used with medical device 202, capnograph 1504 is displayed on testing screen 1502. If a capnography sensor was not being used, i.e., "Source" corresponding to soft key 1508 was configured to "Electrodes", then a capnograph would not be displayed and a transthoracic impedance graph would be displayed instead. If both the capnography sensor 218 and electrodes 125*a* and 125*b* were being used i.e. "Source:" was configured to "both", then both the capnograph and transthoracic impedance graph may be displayed on screen 1502.

According to testing screen 1502, the present status 1520 of the testing indicates "Waiting for ventilation", which means that the medical device 202 is waiting for capnography sensor 218 to detect a positive air flow from ventilation bag 112 of FIGS. 1A and 1B. The results of Test1 1522 indicate that the test passed. The results of Test 1 1522 further show that a confirmation was provided by the user that subject's left lung was auscultated and 4 breaths were detected by capnography sensor 218.

Further, according to testing screen 1502, the result of Test 2 1524 indicates that capnography sensor 218 detected 1 breath, however, since the user has not confirmed a breath from auscultation of the right lung, test 2 has not completed. Test timer 1506, which was originally set to 60 seconds using soft key 1514, indicates that there are 35 seconds left in the overall testing period including the time to complete Test 2 and Test 3. If Test 2 and Test 3 are not completed within the time period left, which is 35 seconds, then the overall testing will fail and Status 1502 will report "Failed" and the reasons for the failure.

Figure 15C:
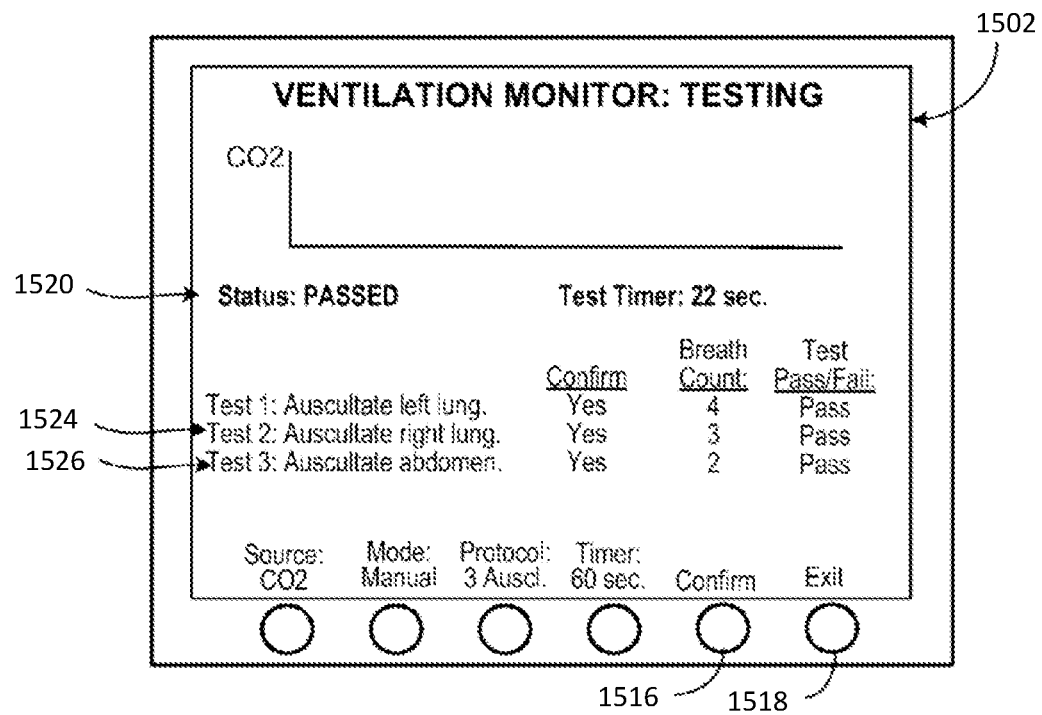
FIG. 15C is a diagram of a testing screen on a medical device showing the testing has passed, the medical device is configured in a manual mode for use with a capnography sensor and a protocol comprising three auscultations according to an example embodiment.

FIG. 15C is a diagram of a testing screen 1502 on the medical device 202 showing the testing has passed, the medical device 202 configured in a manual mode for use with capnography sensor 218 and a protocol comprising three auscultations according to an example embodiment. In the embodiment, screen 1502 shows a continuation of the testing as shown in the screen of FIG. 15C. According to screen 1502, the results of Test 2 1524 indicate that the user has confirmed with soft key 1516 that the subject's right lung has been auscultated and at least one breath was detected. Further, since capnography sensor 218 has detected at least one breath, 3 breaths in this case, Test 2 has passed.

In the embodiment, the results of Test 3 1526 indicate that the user has confirmed with soft key 1516 that the subject's abdomen has been auscultated and no breathing was detected. Further, since capnography sensor 218 has detected at least one breath, 2 breaths in this case, Test 3 has passed. Since each of Test 1, Test 2 and Test 3 have passed; overall status 1520 indicates that the testing has passed. In an embodiment, the results of the overall testing including the results of each of the Tests, e.g. Test 1, Test 2 and Test 3, are saved in memory, for example, in a FLASH memory such as non-volatile memory 209 of FIG. 2. At this point, the user may exit the Ventilation Monitor Testing by pressing soft key 1518.

Figure 15D:
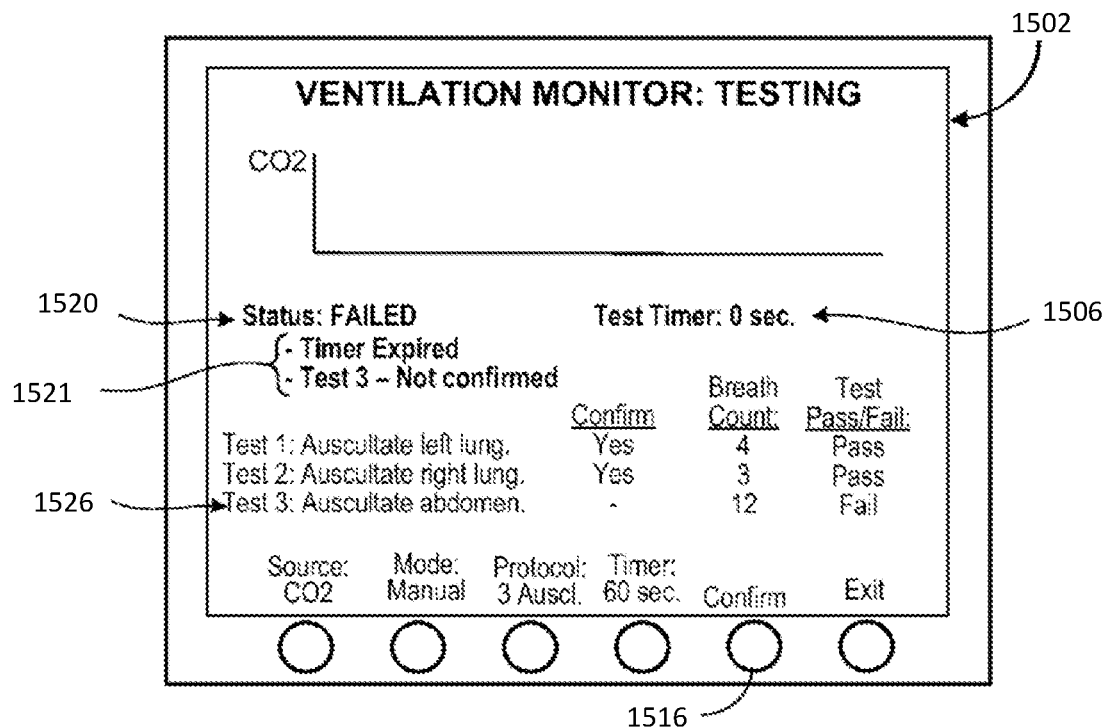
FIG. 15D is a diagram of a testing screen on a medical device showing that the testing has failed, the medical device is configured in a manual mode for use with a capnography sensor and a protocol comprising three auscultations according to an example embodiment.

FIG. 15D is a diagram of a testing screen 1502 on the medical device 202 showing that the testing has failed, the medical device 202 configured in a manual mode for use with capnography sensor 218 and a protocol comprising three auscultations according to an example embodiment. In the embodiment, screen 1502 shows a continuation of the testing as shown in screen 1502 of FIG.

In the embodiment, the results of Test 3 1524 indicate that the test has failed, which has caused the overall testing Status 1520 to indicate failure. Although the capnography sensor 218 detected 12 breaths of the subject, the user did not confirm a positive result of the subject's abdominal auscultation in Test 3 using soft key 1516 within the timer period. As a result, test timer 255 counted down to 0 as indicated at 1520 and the overall testing failed. Reasons for the failure of the overall testing 1521 indicate that the timer expired and that a confirmation in Test 3 was not received.

Figure 15E:
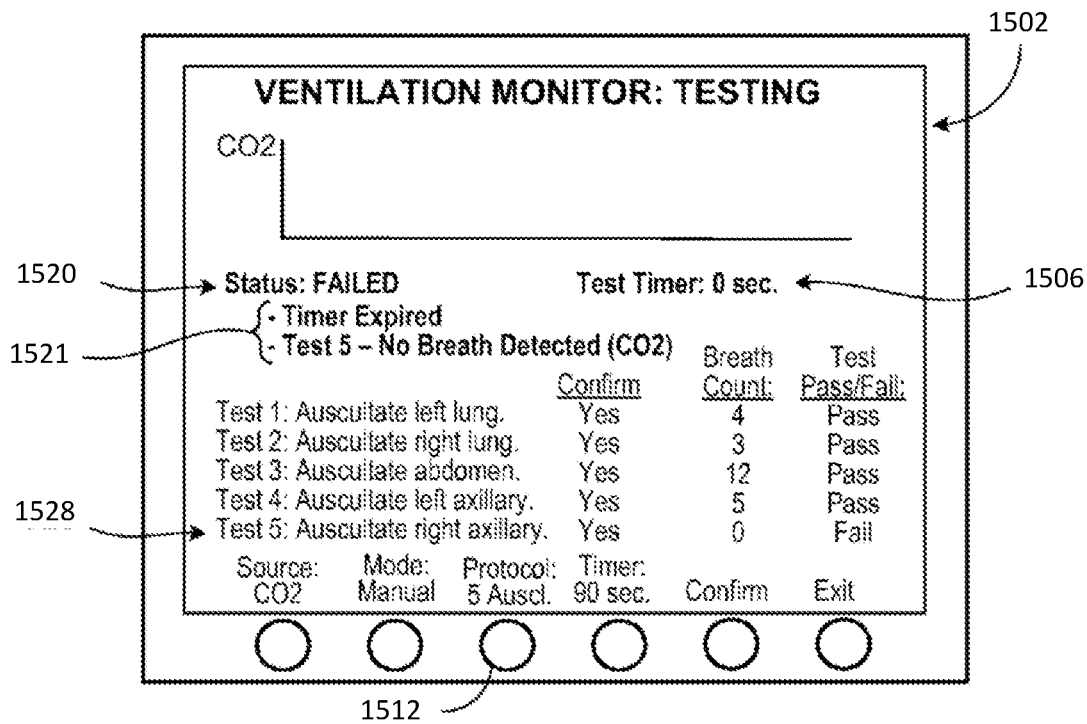
FIG. 15E is a diagram of a testing screen on a medical device showing that the testing has failed, the medical device is configured in a manual mode for use with a capnography sensor, and a protocol comprising five auscultations according to an example embodiment.

FIG. 15E is a diagram of a testing screen 1502 on the medical device 202 showing that the testing has failed, the medical device 202 configured in a manual mode for use with capnography sensor 218 and a protocol comprising five auscultations according to an example embodiment. In the embodiment, screen 1502 shows that a user configured the ventilation monitor testing using soft key 1512 to require 5 auscultations to be performed on the subject including auscultations of the subject's left lung, right lung, abdomen, left axillary and right axillary.

Testing screen 1502 shows that Tests 1 through 4 have passed, however, Test 5 has failed. In Test 5 1528, although the user confirmed that at least one breath was detected during auscultation of the subject's right axillary, capnography sensor 218 did not detect at least one breath. Screen 1502 shows the results of Test 5 1528, which indicate that the subject's breath count did not increment (remained at 0) and Test 5 failed as a result. The failure of a capnography sensor 218 to detect a breath may be due to a number of reasons such as endotracheal tube 129 of FIG. 1B becoming dislodged from the subject's trachea or the subject may have stopped breathing. As the medical device 202 was waiting for capnography sensor 218 to detect a breath from subject 102, test timer counted down to 0 as indicated at 1506 and triggered a failure of the overall testing 1520. Screen 1502 further indicates that reasons 1521 for the failure of the overall testing was that the timer expired and no breath was detected in Test 5.

Figure 15F:
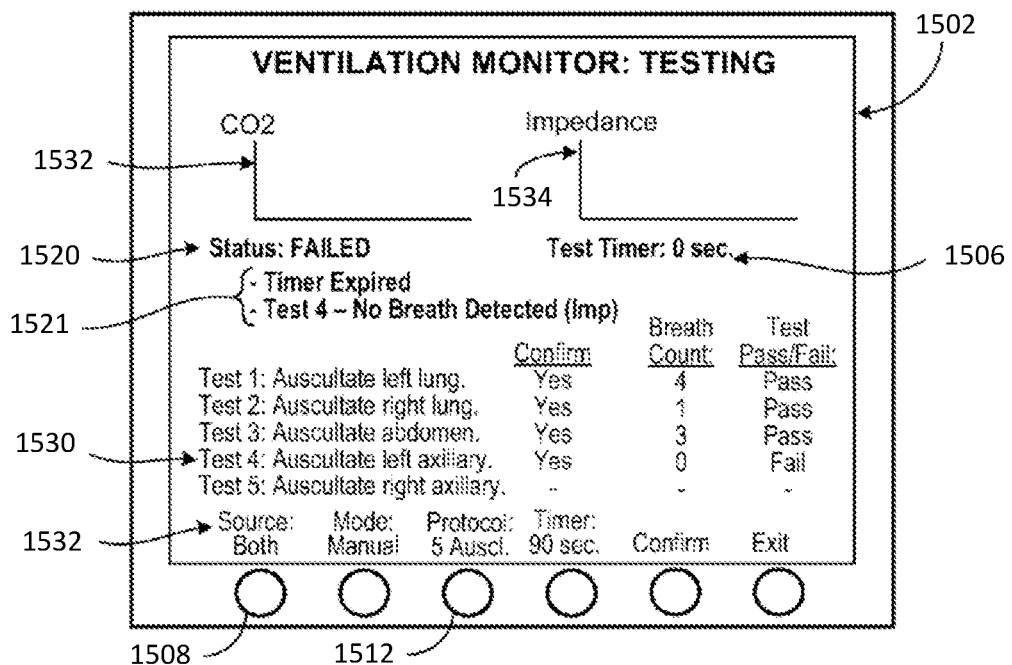
FIG. 15F is a diagram of a testing screen on a medical device showing that the testing has failed, the medical device is configured in a manual mode for use with a capnography sensor, electrodes, and a protocol comprising five auscultations according to an example embodiment.

FIG. 15F is a diagram of a testing screen 1502 on the medical device 202 showing that the testing has failed, the medical device 202 configured in a manual mode for use with capnography sensor 218, electrodes 125a and 125b, and a protocol comprising five auscultations according to an example embodiment. In the embodiment, screen 1520 shows that a user configured the ventilation monitor testing using soft key 1512 to require 5 auscultations to be performed on the subject including auscultations of the subject's left lung, right lung, abdomen, left axillary and right axillary. Further, screen 1502 shows that the user configured the source 1508 to be both the capnography sensor 218 and electrodes 125a and 125b of FIG. 1B. As a result, both a capnograph 1332 and transthoracic impedance waveform 1534 are shown in screen 1000.

Testing screen 1502 shows that Tests 1 through 3 have passed, however, Test 4 1530 has failed. In Test 4, although the user confirmed that at least one breath was detected during auscultation of the subject's left axillary, system 200 configured with capnography sensor 218 and electrodes 125a and 125b indicted a failure to detect a breath from subject 102. Since source 1508 is set to "both", the system 200 must detect a breath from both capnography sensor 218 and electrodes 125a and 125b. Screen 1502 shows the results of Test 4 1530, which indicate that the subject's breath count did not increment (remained at 0) and Test 4 failed as a result. Screen 1502 further indicates that reasons 1521 for the failure of the overall testing was that the timer expired and no breath was detected in Test 4 with respect to the transthoracic impedance testing using electrode 125a and 125b. Since source 1508 was set to "both", even though system 200 may have detected a breath using capnography sensor 218, the overall testing failed since no breath was detected with respect to the transthoracic impedance testing.

The failure of the transthoracic impedance to detect a breath may be due to a number of reasons such as electrode 125a or electrode 125b becoming disconnected from the subject's chest or back or the subject may be in repertory distress. As medical device 202 was waiting for the transthoracic impedance testing using electrodes 125a and 125b to detect a breath from subject 102, test timer 1506 counted down to 0 and triggered a failure of the overall testing indicated at 1010.

In another embodiment, if source 1508 was set to "either" for example, a test such as Test 4 could pass providing that system 200 detected a breath using either capnography sensor 218 or transthoracic impedance testing and the user confirmed the presence of a breath by auscultation.

Figure 15G:
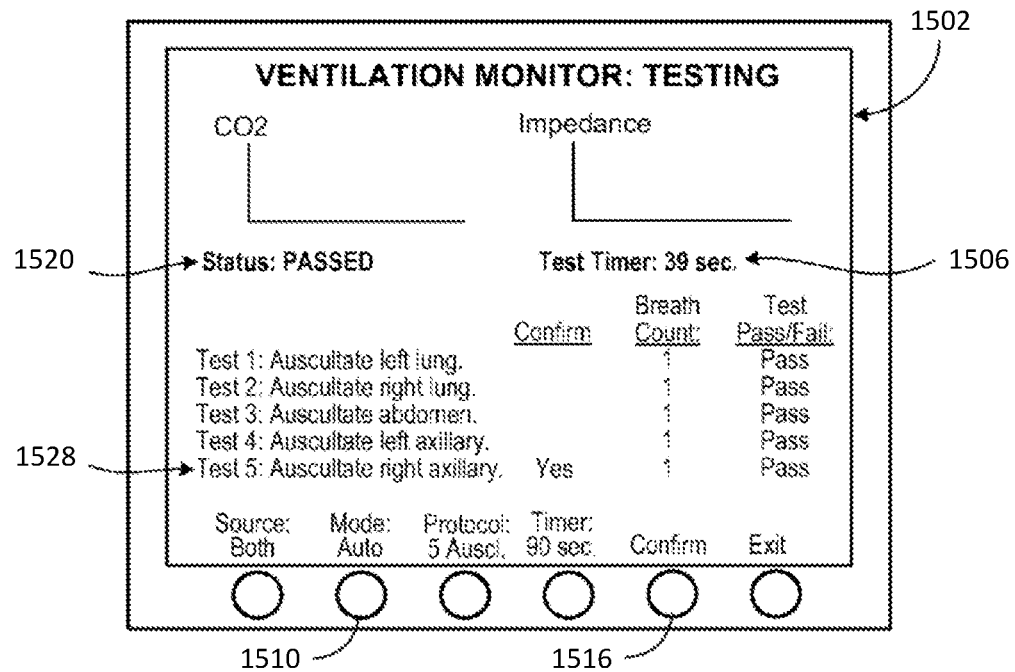
FIG. 15G is a diagram of a testing screen on a medical device showing that the testing has passed, the medical device is configured in an automatic mode for use a capnography sensor, electrodes, and a protocol comprising five auscultations according to an example embodiment.

FIG. 15G is a diagram of a testing screen 1502 on the medical device 202 showing that the testing has passed, the medical device 202 configured in an automatic mode for use with capnography sensor 2180, electrodes 125a and 125b, and a protocol comprising five auscultations according to an example embodiment.

Screen 1502 shows that the user configured the mode to be automatic using soft key 1510. As a result, the user may confirm a positive result for each of the auscultations performed by pressing confirm soft key 1516 once when the auscultations are completed but before the expiration of test timer at indicated at 1516. For example, according to screen 1502 the user confirmed a positive result for each of the auscultations as indicated in result of Test 5 1528. Testing screen 1502 shows that each of Tests 1 through 5 has passed and the status 1520 for the testing indicates "Passed."

In some embodiments, an airflow sensor may be used in the implementations described above with respect to intubation assist. That is, the airflow sensor placed in the patient airway may provide an initial input to the medical device and/or portable computing device that a positive pressure breath has been given and that confirmation with one or more physiological sensors (e.g., capnography, transthoracic impedance, acoustic sensor(s)) may subsequently be required, as discussed above, followed by auscultation at various sites (e.g., left lung, right lung, abdomen, left axillary, right axillary). That is, the physiological measurement may be correlated with the detected airflow in the patient's airway to confirm that the ventilation breath initiated detected by the airflow sensor has reached the patient's lungs. For example, when the airflow sensor detects air flow in the patient airway due to a positive pressure breath, a timer may be initiated that sets an interval for confirmation with one or more physiological parameters, such as those described above, to occur. If the set interval expires before such confirmation is received, then an alert may be provided indicating that the air flow provided from the positive pressure breath has not reached the lungs. However, if physiological confirmation is received before the set interval expires, then the medical device may move on to the next step where a positive result of auscultation is to be confirmed. It should be appreciated that embodiments discussed below with respect to FIGS. 16A-16I, while described in the context of post-intubation monitoring, may be used in conjunction with assisting caregivers in the initial intubation tube placement.

Figure 16A:
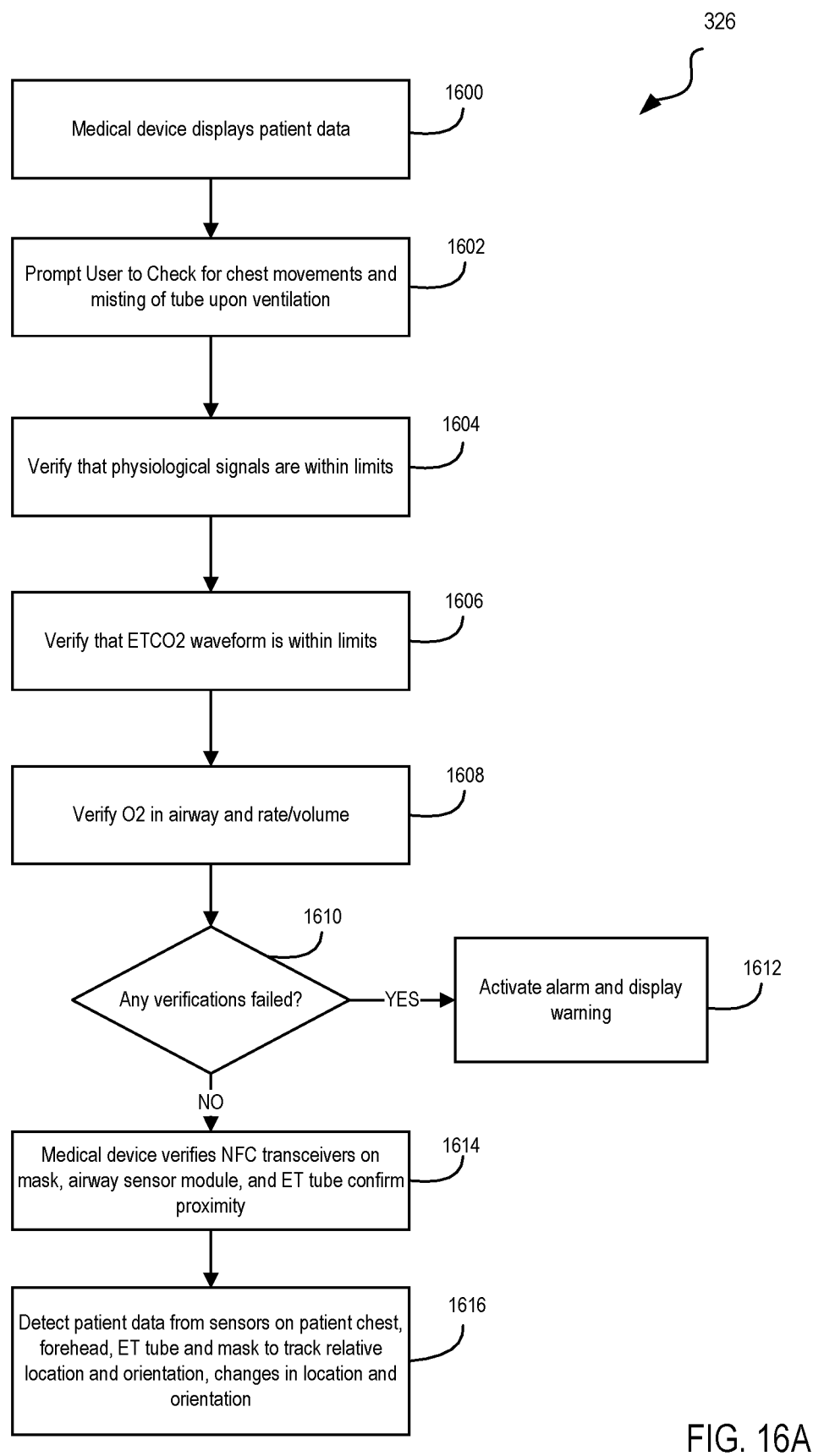
FIG. 16A is a flow chart illustrating steps performed during the verification of endotracheal tube placement in accordance with an embodiment.

FIG. 16A is a flow chart illustrating typical steps performed during the verification of the endotracheal tube placement. Verification of tube placement is an important step to ensure that the endotracheal tube was correctly placed within the patient's lungs. A common mistake made during intubation is for the rescuer (or caregiver) to accidentally place the endotracheal tube into the esophagus of the patient. When this occurs, the patient 102 is deprived of ventilation and oxygenation, and is at a significantly greater risk for aspiration as a result of gastric insufflation. Failure to detect and address esophageal intubation can lead to serious injury or death.

In the first step 1600, the medical device 202 displays the relevant data e.g., flow rate in the patient's airway, oxygen in the airway, NIBP, SPO2, heart rate, ECG waveform, and ETCO2. In step 1604, the medical device 202 may prompt the rescuers 104, 106 to check for chest movements and misting of tube upon ventilation. In the next step the medical device 202 verifies that the physiological or airway gas measurement signals (e.g., ETCO2, O2, flow rate and volume) are within limits. Next, in step 1606, the medical device 202 verifies ETCO2 waveform, e.g., to differentiate between esophageal and tracheal placement. In step 1608, the medical device 202 verifies the oxygen delivery in the airway via the respective oxygen sensor as well as the rate and volume of the flow using the respective flow sensor. Next, the medical device determines if any of these verifications failed. If any verifications failed, then the medical device activates an alarm in step 1612. If no verifications failed, then the medical device verifies NFC transceivers on airflow sensor module and ET tube to confirm proximity there between, that the BVM is on the patient in step 1614.

Lastly, the medical device may use information from the sensors 210-221 to detect patient data from sensors (e.g., sensors for detecting motion, displacement, velocity, acceleration) on patient chest, forehead, ET tube and mask to track relative location and orientation, changes in location and orientation in step 1616.

Figure 16B:
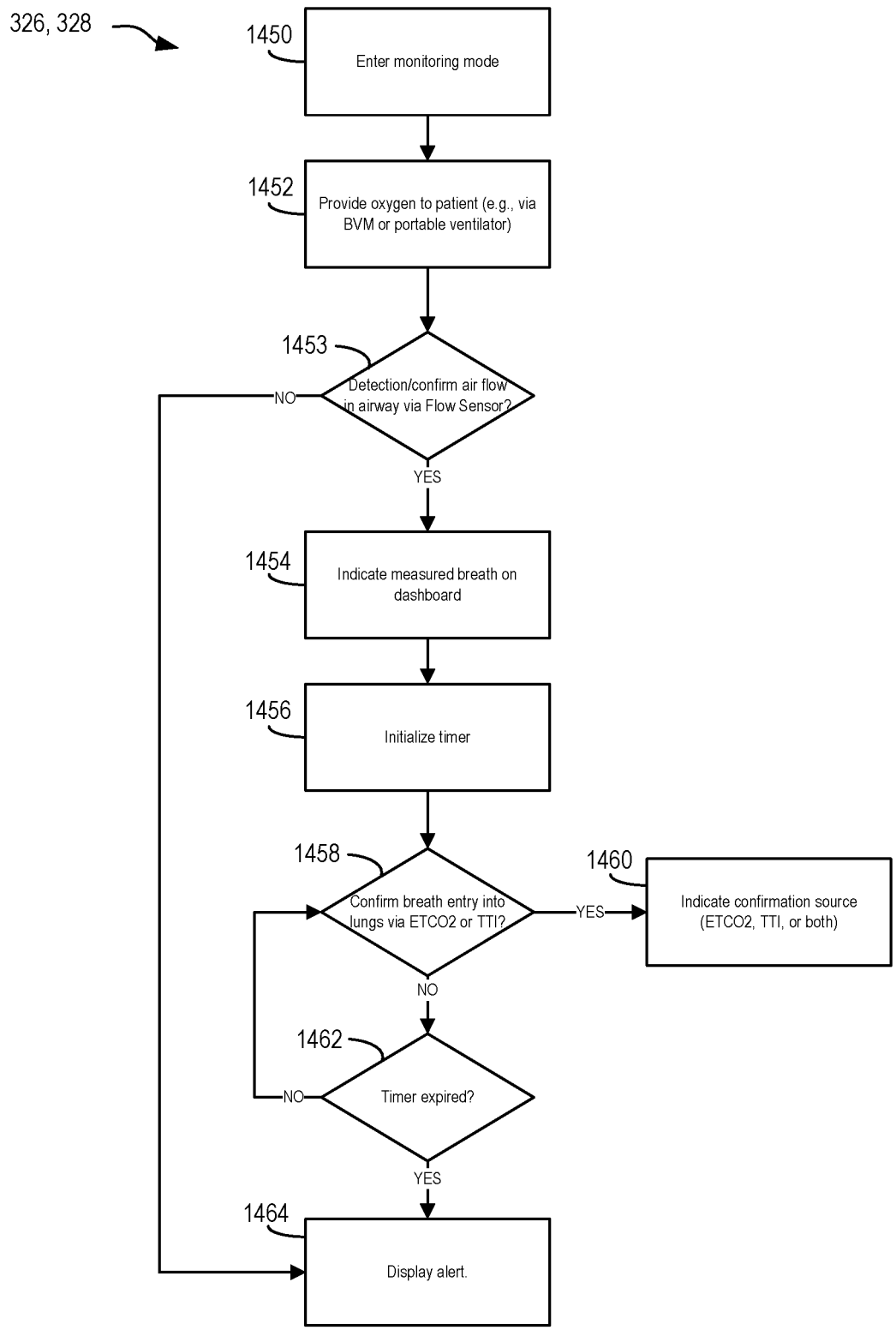
FIG. 16B is a flow chart illustrating exemplary steps performed during the post intubation verification in accordance with an embodiment.

FIG. 16B is a flow chart illustrating steps performed during the post intubation verification (e.g., step 326) in accordance with an embodiment. Once intubation has been completed FIGS. 16E-16I illustrate examples of continuous tube placement verification using capnography sensors, leads/pads to measure transthoracic impedance, additionally using a flow sensor to monitor air flow in the airway being provided to the patient. While the user interface display provides a dashboard configuration that shows the results of ET tube verification in the context of post-intubation monitoring, it can be appreciated that other configurations and interfaces may be possible. It should also be understood that embodiments discussed with respect to continuous monitoring of the patient post-intubation to verify that the intubation tube is properly placed may be applicable for assisting a caregiver in initially placing the intubation tube.

While FIG. 16B is directed to an implementation for post intubation monitoring, as noted above, these steps could also be implemented during the initial intubation procedure (e.g., step 328). For example, when a ventilation breath is detected via the airflow sensor, in order to confirm that the ventilation breath has reached the lungs, the medical device 202 may then utilize sensors (e.g., capnography, impedance, acoustic) and different thresholds to determine whether the breath has appropriately reached the lungs, leaking, and/or tube dislodgement. This is accomplished by a comparison of measured physiological information (e.g., CO2 information, transthoracic impedance, acoustic information) to a predetermined criterion that should be satisfied for the medical device to determine that the ventilation breath has entered the lungs and, hence, the intubation tube has been properly placed. For example, during the initial intubation procedure, after the airflow sensor detects the presence of air in the patient's airway, the predetermined criterion for verifying that the air has reached the lungs may include appropriate thresholds (or ranges) for breath detection, e.g., values over 5 mm Hg for ETCO2 may indicate that the intubation tube is initially properly placed, for example that it is properly placed in the trachea such that airflow in and out of the lungs can occur. During initial tube placement, in some cases, the acceptable threshold in the case of ETCO2 could be lower in comparison to that when used for post-intubation monitoring, or in some cases, the acceptable threshold in the case of ETCO2 could be similar to that when used for post-intubation monitoring. Some examples of thresholds to indicate that the tube has been placed and that a ventilation breath has entered the lungs may be, for example, 2-10 mm Hg, 5-10 mm Hg, 5-7 mm Hg, 2-5 mm Hg, 2 mm Hg, 5 mm Hg, 7 mm Hg, 10 mm Hg, amongst others. In some cases, during the initial tube placement procedure, the acceptable range may be wider (broader) with the lower end of the range including a value lower than what may be used for post-intubation monitoring (e.g. 0 to 50 mm Hg for ETCO2, 2 to 40 mm Hg, 5 to 35 mmHg, etc.) in comparison to when the already intubated patient is being monitored for possible tube dislodgement, leakage, etc. The benefit of this comparatively wider initial range is that the medical device 202 may be able to detect and confirm a number of different types of breaths, which may be helpful during an intubation procedure where no initial baseline may have been established, so as to verify that the tube has been placed in the airway (e.g., and not in the patient's esophagus).

Alternatively, or in addition, a prior baseline (e.g., TTI) may be taken and a comparison upon initial tube placement may be made to the prior baseline to determine if the tube has been properly placed. TTI may be a preferable physiological measurement when taking a prior baseline because the patient will exhibit a TTI value even if a tube is not in place.

Upon verification of tube placement, the medical device 202 could automatically (or upon manual activation by a user) switch to an alternative threshold and/or range, or may maintain similar criteria for verifying that a breath has entered the lungs. In some cases, the alternative threshold and/or range may be narrower than that used for the initial intubation placement procedure, with the lower end of the range higher than the previous threshold or range (e.g. 5-10 mm Hg, 5-12 mm Hg, 7-12 mm Hg, 7 mm Hg, 10 mm Hg, 12, mm Hg, etc.). This narrower range is another example of predetermined criterion that may be used to determine whether the ET tube is and/or remains placed in a desirable position for the patient to be appropriately receiving positive pressure ventilation breaths (from bag or from ventilator device). The advantage of utilizing this narrowing range would be the ability to detect (and generate alerts) upon smaller deviations that are the result of, e.g., tube leakage or tube dislodgement. In various embodiments according to the present disclosure, the medical system may obtain one or more baseline values for breaths pre and post intubation and thus any deviation from the baseline could indicate that a problem (e.g., tube dislodgement, leakage, poor seal, etc.) may have arisen. During post-intubation monitoring, there may also be an appropriate acceptable upper threshold or end of the range for ETCO2 which, when exceeded, may trigger a different type of alert. For example, if the ETCO2 has increased for example, past 30 mm Hg, 35 mm Hg, 40 mm Hg, 45 mm Hg, or another value, then the medical device may generate an alert informing a caregiver to check the patient, for example, in the even that spontaneously respiration or return of spontaneous circulation (ROSC, e.g., in the case of cardiac arrest) has occurred.

Various types of baselines may (e.g., via capnography, transthoracic impedance, acoustic sensing, amongst others) be taken at different points in the intubation process. Such baselines may serve as a physiological measurement of whether ventilation air provided via the intubation tube has reached the patient's lungs in a desirable manner. For example, when a positive pressure breath is detected by the airflow sensor, one or more physiological measurements that appreciably deviate (e.g., greater than 10%, 20%, 30%, 40%, 50%, etc.) from a baseline obtained previously, pre-intubation, may provide an indication that the intubation tube has been misplaced, dislodged, started to leak, etc. Though, if the physiological measurement(s) do not significantly deviate (e.g., remains within 10%, 20%, 30%, 40%, 50%, etc.) from the previously taken baseline, then it may be determined that the intubation tube is properly placed or remains in proper place.

A baseline may be taken prior to the intubation procedure, to assist in the ET tube placement procedure. In such a case, the physiological measurement(s) are taken to obtain a prior baseline before an attempt is made to insert the ET tube. When the ET tube is inserted into the patient's trachea and a positive pressure ventilation breath has been given, an appropriate change in the physiological measurement(s) as compared to the prior baseline may indicate that ET tube serves as a suitable conduit through which the ventilation breath is able to reach the lungs. Such changes in the physiological measurement(s) to detect whether the ET tube is properly placed may be akin to the predetermined criteria discussed herein, for example, deviations from the prior baseline, exceeding or remaining below a threshold, falling within or outside a range, for example. For instance, the prior baseline before intubation is attempted may record an ETCO2 value of 0 mm Hg. Upon successful ET tube placement, the ETCO2 value may increase, for example, to 20 mm Hg, which is a significant enough deviation from the prior baseline to confirm that the ET tube has been properly placed. Or, the prior baseline before intubation is attempted may record a first TTI value. When the ET tube has been successfully placed, a second TTI value measured upon the patient receiving a ventilation breath may be greater than the prior baseline (first TTI value) such that the medical device may confirm that the ET tube is properly placed. As discussed above, it may be preferable to use TTI to obtain a prior baseline when first initiating placement of the ET tube because TTI provides a mechanical measurement of the patient, regardless of the physiological condition. This way, a comparison may be made between a first TTI value obtained before the ET tube is placed to a second TTI value obtained after the ET tube is placed.

Or, a baseline may be taken immediately upon initial completion of the tube placement procedure, to monitor whether the ET tube remains in proper position, or if a problem has arisen with the ET tube placement. In this case, the physiological measurement(s) are taken right after the tube has been inserted into the patient's airway to obtain an initial baseline of positive pressure ventilation breaths. After the initial baseline is taken, the patient is continuously monitored, both physiologically and mechanically (e.g., detecting patient movement as well as whether the tube remains in place). During this post-intubation monitoring phase, the airflow sensor may detect the presence of a ventilation breath in the patient's airway, and the subsequent physiological measurement(s) recorded may be compared to the initial baseline to indicate whether ET tube remains as a suitable conduit through which the ventilation breath(s) are able to reach the lungs. Changes in the physiological measurement(s) to detect whether the ET tube remains properly placed may be similar to the predetermined criteria discussed herein, for example, deviations from the prior baseline, exceeding or remaining below a threshold, falling within or outside a range, for example. For instance, the initial baseline after intubation is completed may record an ETCO2 value (e.g., average ETCO2 value over several breaths) of 20 mm Hg. If the ET tube remains properly placed, then subsequently recorded ETCO2 values may be within an acceptable range around the initial baseline. However, if the ET tube becomes dislodged or if a leak occurs, then the subsequently recorded ETCO2 values may drop, for example, to 5 mm Hg or lower, which may be a significant enough deviation from the initial baseline to result in an alert (e.g., on the display of the medical device, or to a remote station or mobile device) that the ET tube placement should be checked. Or, if subsequently recorded ETCO2 values are substantially above the initial baseline, then it may be possible that the patient condition has changed, for example, improved such that spontaneous respiration or ROSC (e.g., in the case of cardiac arrest) has occurred. Accordingly, there may an alert that the patient should be checked, as discussed further below. Similarly, the initial baseline after intubation may include a first TTI value (e.g., average TTI value over several breaths). If the ET tube remains properly placed, then subsequently recorded TTI values may be within an acceptable range around the initial baseline. However, if the ET tube becomes dislodged or if a leak occurs, then the subsequently recorded TTI values may drop enough such that a substantial deviation from the initial baseline may result in an alert (e.g., on the display of the medical device, or to a remote station or mobile device) that the ET tube placement should be checked.

Furthermore, a dynamic baseline may be taken after completion of the tube placement procedure when the patient is being continuously monitored for any physiological (e.g., oxygen saturation, blood pressure, CO2 production, metabolic parameters, etc.) or mechanical (e.g., patient movement, tube placement) changes. The dynamic baseline is similar in concept to the initial baseline, except the dynamic baseline may be continually updated, as discussed further below in various embodiments. In fact, when the ET tube is initially placed, the dynamic baseline and the initial baseline may be the same. Hence, the physiological measurement(s) from positive pressure ventilation breaths are continually taken as the patient is being monitored to update the dynamic baseline. In this post-intubation monitoring phase, the airflow sensor may detect the presence of a ventilation breath in the patient's airway, and the subsequent physiological measurement(s) recorded may be compared to the dynamic baseline to indicate whether ET tube remains as a suitable conduit through which the ventilation breath(s) are able to reach the lungs. Changes in the physiological measurement(s) to detect whether the ET tube remains properly placed may be similar to the predetermined criteria discussed herein, for example, deviations from the prior baseline, exceeding or remaining below a threshold, falling within or outside a range, for example.

Taking a baseline may be preferable when measuring TTI values because the TTI may vary significantly from patient to patient. Accordingly, when making a determination that the ET tube remains properly placed or is no longer properly placed, subsequently recorded TTI values may be compared to the baseline, rather than a particular number or range.

It should be appreciated that multiple different types of physiological measurements (e.g., CO2, TTI, acoustic) may be used to confirm that a ventilation breath has reached the lungs, individually or in combination with one another. Such a combination of sensors may provide for redundancy in the system. For example, if one of the physiological sensors is unavailable (e.g., failed, unplugged, provides a parameter that is not relevant), then other sensors may be able to provide the appropriate confirmation. For instance, if both capnography and TTI sensors are employed, yet capnography is not yet plugged in and impedance sensors are placed on the patient, then TTI may be used initially. Conversely, if impedance sensors are not yet placed on the patient and the capnograph is available, then CO2 information may be used initially. Or, if all types of sensors are available, then the medical device may implement accordingly.

Returning to FIG. 16B, in the first step 1450, after it has been confirmed that the ET tube has been placed via the intubation assist feature, the medical device 202 may automatically enter a monitoring mode (e.g., testing and verification mode). Alternatively, the rescuers 104, 106 may manually enter the monitoring mode via a button, softkey, knob, or touchscreen interface, for example. This monitor mode causes a monitoring dashboard 1545 to be displayed on the display 1502 of the medical device 202.

In the next step 1452, the rescuers 104, 106 provide oxygen to the patient 102 (e.g., via BVM or portable ventilator). Data from the flow sensor 127 determines/confirms whether a positive pressure breath has been given by detecting air flow in the patient's airway in step 1453. In one embodiment, a timer may be initialized upon entering into monitoring mode. Upon expiration of the timer an alert would be displayed indicating that no airflow is detected and the rescuers should check for clogged airways, whether there is a leak in the airway, the cuff of the airway, or if some component of the BVM or endotracheal tube has become disconnected, to list a few examples. Determination of whether a ventilation breath has entered the lungs before expiration of a timer is yet another example of a predetermined criterion that can be implemented to determine of the ET tube is properly placed. In this example, the expiration of the timer is indicative that the tube is not desirably placed because while the presence of airflow indicative of a given breath was detected, there was no confirmation that the given breath has reached the lungs in the allotted time.

If the flow sensor 127 detects air flow in the airway (e.g., from oxygen delivered to the patient 102), then an indication is displayed in step 1454 that a positive pressure breath has been detected. In the next step 1456, a timer is initialized that sets an interval for confirmation that the positive pressure breath has reached the lungs. A physiological measurement may be used as correlation with the detected airflow in the patient's airway to confirm that the ventilation breath initiated detected by the airflow sensor has reached the patient's lungs. This timer may have a default value such as 10 seconds or a default range such as between 5-10, 10-15, 15-20, 5-15, of 10-20 seconds, to list a few examples. Additionally, the medical device may further include a series of user-selectable preset times (e.g., 5, 10, 15, 20, 25, 30 seconds, to list a few examples) for the timer. In still another embodiment, the timer may be a user programmed time value based on a physician/administrator decision. While the time is counting down to zero, in step 1458, the one or more physiological sensors measure physiological information of the patient (e.g., pads/lead 125a, 125b measuring transthoracic impedance, a capnography sensor 218, acoustic sensor, or other sensor for confirming that the breath has entered into the lungs). This information may then be used to determine whether air from the delivered breath detected in step 1453 has entered (and/or exited) the lungs. In general, the medical device 202 performs this determination by comparing the measured physiological information (e.g., ETCO2 or transthoracic impedance) against one or more predetermined criteria. For example, the predetermined criterion could include an ETCO2 value exceeding a predetermined threshold (e.g., greater or less than 50% of an original baseline, such as an initial or dynamic baseline), an ETCO2 value falling within a desired range, an average of multiple ETCO2 values exceeding a threshold, the average of multiple ETCO2 values exceeding a threshold, a trend in the ETCO2 values, an averaged ETCO2 value being greater or less than a percentage of a moving average of a plurality of previously measured ETCO2 values, an averaged ETCO2 value being greater or less than a percentage of a moving average of a plurality of previously measured ETCO2 values, or another suitable method of confirming whether the ventilation breath has properly entered into the lungs.

Additionally, the predetermined criteria may utilize alternatively, or in addition, a measure of transthoracic impedance. For example, the predetermined criterion may include transthoracic impedance value exceeding a predetermined threshold (e.g., greater or less than 50% of an original baseline, such as an initial or dynamic baseline), a transthoracic impedance value falling within a desired range, an average of multiple transthoracic impedance values exceeding a threshold, the average of multiple transthoracic impedance values exceeding a threshold, a trend in the transthoracic impedance values, an averaged transthoracic impedance value being greater or less than a percentage of a moving average of a plurality of previously measured transthoracic impedance values, an averaged transthoracic impedance value being greater or less than a percentage of a moving average of a plurality of previously measured transthoracic impedance values. Specific, non-limiting examples, of predetermined threshold and predetermined criterion are described in detail below.

In another specific example of predetermined criteria, if sufficient expiratory CO2 of approximately at least 5 mm Hg, is detected and/or a transthoracic impedance (TTI) waveform or amplitude is indicative of a lung volume change of at least 150 mL have been detected, within the allotted time interval set by the timer, then it may be confirmed that the positive pressure ventilation breath has entered into the lungs and, hence, that the ET tube remains properly placed.

In another example, impedance may be measured to be from approximately 1.5 ohms to 2.5 ohms. However, in yet another example, a range from 0.5 and 1.0 ohms may also be measured. These values may be measured by the impedance sensor and then processed and amplified by the processor of the medical device. In one example, the signal is sent through one or more high, low, and/or bandpass filters in order to remove unwanted values below a desired level. Peaks may then be identified and those remaining peaks are amplified (e.g., by squaring the peak values). This squaring causes the values of the peaks to increase, where the largest peaks increase disproportionally more in comparison to other peaks. Thus making distinction of peaks easier.

While the range may vary from person to person, the change in impedance is identifiable and detectable by the medical device 202. Still another examples of a predetermined criterion includes an ETCO2 value in the range between approximately 35-45 mm Hg, which may be considered typical for a healthy patient. Thus, if the measured ETCO2 value is within this range, the medical device is able to determine that measured ETCO2 value satisfies the predetermined criterion. The thresholds for intubation and post intubation could be based around these values. For example, in still another non-limiting example, the predetermined criterion could be based on the lower thresholds for breath detection via ETCO2, which include values such as be 5 mm Hg, 10 mm Hg, 15 mm Hg, or 20 mm Hg, to list a few examples. That is, the medical device would indicate a breath upon at least a measurement of, e.g., 5 mm Hg and anything lower would be filtered out as "noise."

Similarly, in another non-limiting example, the predetermined criterion for determining that the intubation tube remains properly placed could be adjusted to somewhere between 25-30 mm Hg after intubation. As before, of any ETCO2 values falls below that threshold, an alert may be triggered to indicate that there is a possible tube leak or the tube has become dislodged.

In some embodiments, the predetermined criterion may involve a series of initial and/or dynamic baseline measurements obtained from capnography and/or TTI immediately following a successful intubation, and for the dynamic baseline case, continuously updated baseline while the intubated patient is being monitored. For example, substantial changes in EtCO2 may provide an indication that positioning of the ET tube has affected the patient, for example, become dislodged, started to leak, or has been misplaced. Subsequent measurements of EtCO2 and TTI for subsequent breaths may be compared to the baseline. If EtCO2 or TTI waveform amplitude decreases by no more than, for example, approximately 20%, as compared to baseline, then it may be confirmed that the positive pressure ventilation breath has entered into the lungs and, hence, that the ET tube remains properly placed. Alternatively, the conversion coefficient for converting TTI waveform amplitude to lung volume change may be estimated based on measured tidal volume from the flow sensor and the TTI waveform amplitude immediately following successful intubation. If the conversion coefficient increases by no more than, for example, approximately 20%, or other predetermined threshold, then it may also be confirmed that the positive pressure ventilation breath has entered into the lungs and, hence, that the ET tube remains properly placed. Using the ETCO2 signal the medical device 202 is able to identify patterns that could indicate displacement of the ETT or a significant failure to ventilate. In one embodiment, described in further detail below, a ±50% change in the ETCO2 may trigger an alarm based on a number of breaths (e.g., 2-10 breaths) should, for example, 2 or more consecutive or non-consecutive breaths (e.g., 2-5 breaths in consecutive succession or interposed by one or more breaths, etc.) be >±50% of a moving average of the ETCO2 of the number of breaths. For instance, for 2 or more consecutive or non-consecutive breaths (e.g., 2-5 breaths in consecutive succession or interposed by one or more breaths, etc.) where ETCO2<50% of the moving average, the visual alarm may indicate that the ETCO2 is low and that the airway should be checked, for example, "Low ETCO2, Check Airway." Conversely, for 2 or more consecutive or non-consecutive breaths (e.g., 2-5 breaths in consecutive succession or interposed by one or more breaths, etc.) where ETCO2>50% of the moving average, the visual alarm may indicate that ETCO2 levels have changed and that the patient should be checked, for example, "ETCO2 Change, Check Patient." In general, the benefit of using the average of consecutive breaths is to reduce and/or eliminate "noise" from outliers that can occur. This algorithm is described in further detail in FIGS. 16C and 16D.

Alternatively, rather than use of a timer, one or more physiological parameters may be used for confirmation (e.g., without a timer). For example, rather than using a countdown timer for expiration, the medical device 202 may simply wait until the next "cycle." For example, after the BVM is used to provide air into the airway, the medical device could then wait until either the breath is detected via one of parameters (e.g., ETCO2 or TTI) or wait until the BVM is used again. Upon detection of air in the airway from the BVM, without a corresponding confirmation, a lack of exhalation (and a failed test) may be indicated.

If information from one or more of the physiological sensors has confirmed that the positive pressure ventilation breath has entered into the lungs, then a confirmation may be provided along with an indication of which source (ETCO2, TTI, or both) has provided the confirmation in step 1460. If a breath is not detected, then the medical device 202 determines whether the timer has expired in step 1462. If the timer has not expired, then the medical device 202 returns to step 1458 to attempt to detect a physiological signal that confirms whether the positive pressure breath or a spontaneous patient breath has entered into the lungs. If such a confirmation has not been detected 1458 and the timer has expired in step 1462, then an alert is displayed in step 1464. The alert may provide a suggestion to check whether the intubation tube is properly placed.

While not illustrated in this figure, in one embodiment, the timer will automatically reset upon detection and/or confirmation of the breath (oxygen) being provided to the lungs of the patient. Additionally or alternatively, the medical device may include an input to enable the user to manually reset the timer.

Figure 16C:
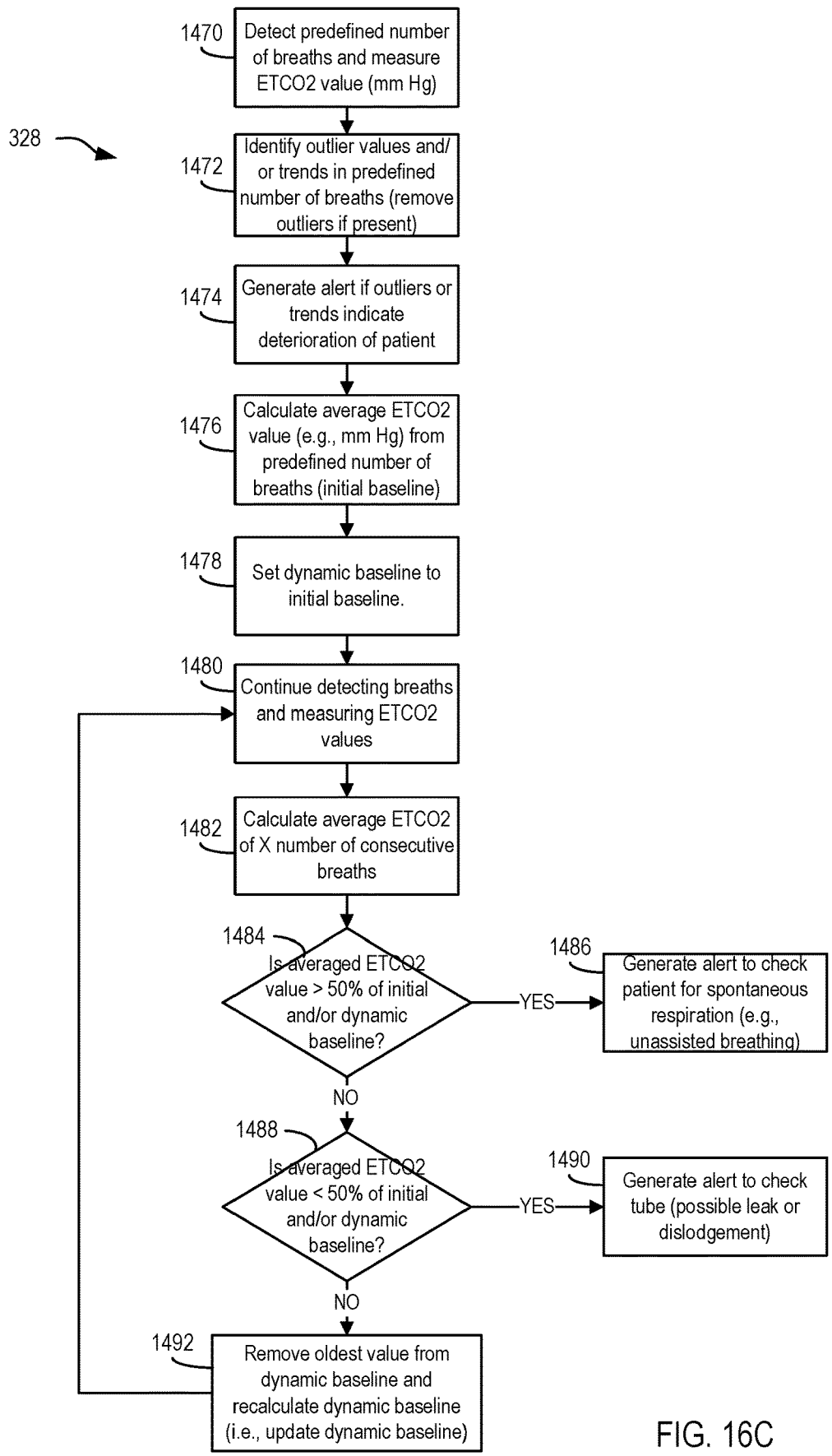
FIG. 16C is a flow chart illustrating exemplary steps performed during the post intubation verification in accordance with an embodiment.
Figure 16D:
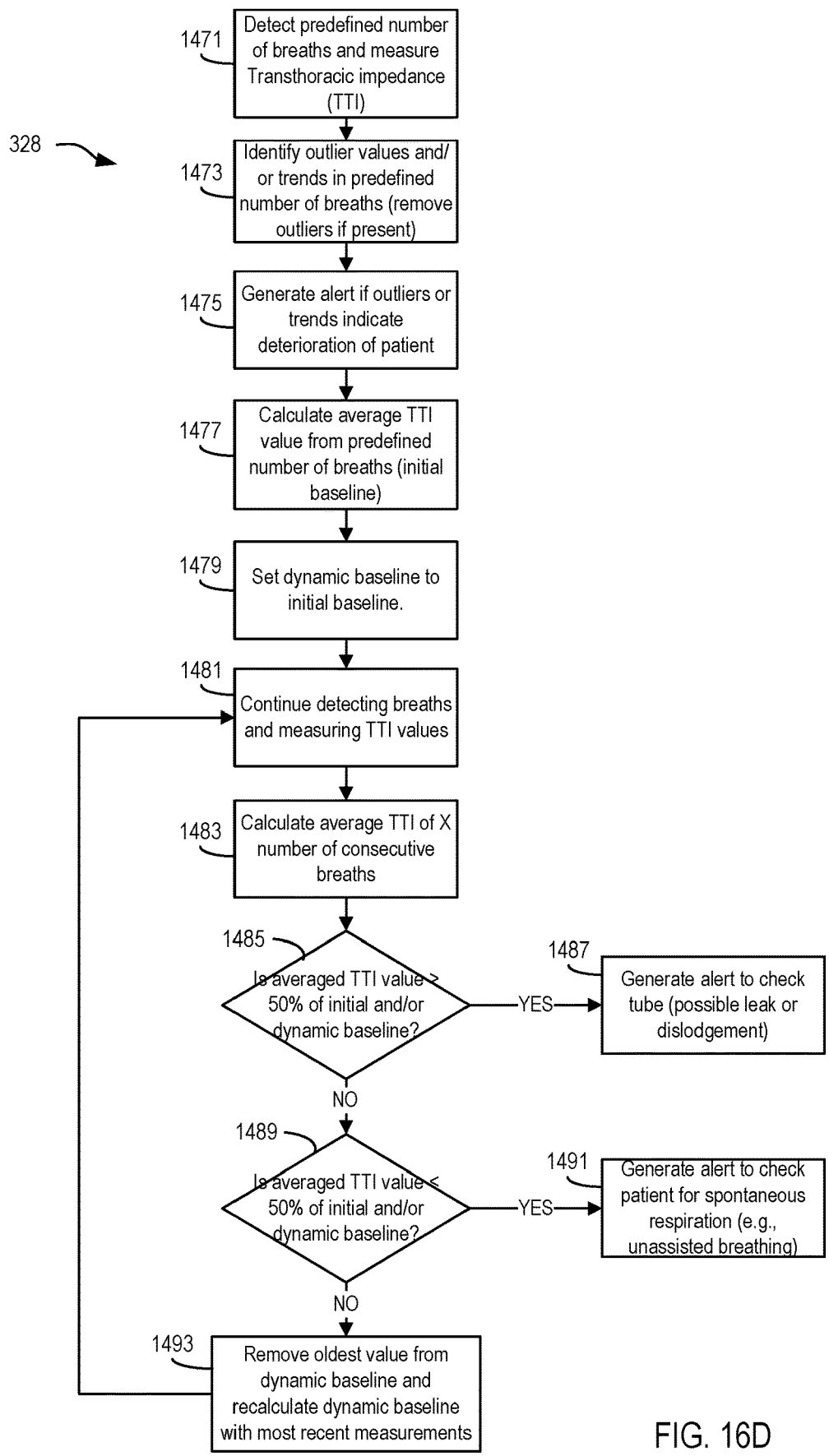
FIG. 16D is a flow chart illustrating alternative exemplary steps performed during the post intubation verification in accordance with an embodiment.

FIGS. 16C and 16D are flow charts illustrating examples of the steps performed during the post intubation verification in accordance with an embodiment. Specifically, as breaths are detected, the medical device 202 monitors and analyzes the breaths over time to determine if the patient is improving or worsening. That is, the medical device 202 determines, based on analyzed breaths, whether the patient has potentially begun spontaneous respiration (e.g., unassisted breathing) or if patient is no longer receiving oxygen (e.g., tube has become dislodged, is leaking, etc.).

Referring to FIG. 16C, in the first step, 1470 the medical device 202 detects a predefined number of breaths (e.g., between 3-10 detected breaths). By way of example, the breaths may be detected via acoustic sensors, capnography sensors, or impedance sensors (e.g., ETCO2, acoustic signals, or TTI). In one example, the number of predefined breaths may be pre-programmed into the medical device 202 or user configured upon initialization of the medical device. In general, the number of breaths needs to be large enough for the medical device 202 to make accurate calculations based on measured ETCO2 and/or TTI values, while also filtering out noise and outlying values. At the same time, the number of detected breaths may be relatively minimal to reduce the amount of lag until useful information is generated. In one example the number of breaths is 2. However, the number of measured ETCO2 and/or TTI values could be any number between 2 and 32 (or more).

In the next step 1472, the medical device 202 may identify outlier values and/or trends and may generate an alert of the outlier or trend to indicate deterioration of the patient in step 1474. This identification of outlier values and/or trends are additional specific examples of predetermined criterion that may be satisfied to verify that a detected breath has entered into the lungs. This may be accomplished by, for example, comparing measured ETCO2 values with other detected breaths and identifying deviations and or trends of widely increasing trends. Illustrated by way of example, if the number of predefined breaths to be measured is 6, and values (measured mm Hg) of: 26, 27, 10, 30, 31, and 28 were measured via capnography sensor; then, the medical device 202 may be able to identify that the $3^{rd}$ value is an outlier. That outlier may provide an indication that the tube was dislodged momentarily or perhaps a section of tube was accidentally disconnected. Consequently, after the $3^{rd}$ breath is detected, the medical device 202 may provide an alert, as indicated in step 1474, to check the tube or patient. Likewise, if the remaining detected breaths return to normal levels, the medical device 202 may simply generate an event marker (e.g., code marker) for later review, in one example.

Similarly, as another example, if the detected breaths have ETCO2 values (mm Hg): 28, 28, 20, 18, 15, and 12, then the medical device 202 device may also generate an alert to check on the patient based on the deteriorating ETCO2 values. In still another example, if the detected breaths have ETCO2 values (mm Hg): 20, 22, 28, 30, 35, and 40, then the medical device can provide an alert to check the patient as the trend is positive and the ETCO2 value may be indicative of a different patient condition. For instance, a substantial increase in ETCO2 (e.g., over 50% upward trend) could indicate the return of spontaneous circulation or a significant change in the patient's condition. Or, such substantial changes may be an indication that the intubation tube has fallen into one of the lungs, when it is desirable for the distal end of the tube to be positioned in the trachea so that ventilation breaths may be able to reach both lungs, rather than only one.

In step 1476, the medical device 202, when the ET tube is placed, may calculate an average ETCO2 value (e.g., in mm Hg) based on the values of the detected predefined numbers of breaths (i.e., an initial baseline). This initial baseline provides a reference for future comparisons, for example, of measured ETCO2 values (or other physiological values such as TTI and/or acoustic). As discussed herein, there are several methods to determine a baseline. Likewise, there are several different times during the intubation procedure in which a baseline may be determined. In one example (discussed above, yet not illustrated in the figures), a prior baseline may be determined prior to tube placement. This prior baseline would represent the condition of the patient prior to any intubation attempts. Thus, any changes in the condition of the patient (i.e., improvements or worsening) are compared against the patient's condition prior to any treatment.

As disclosed in greater detail below, another example for determining baseline is to determine an initial baseline immediately after initial placement of the ET tube. The benefit is that this initial baseline determination can represent both an indication of the condition of the patient as well as a confirmation of the tube placement. For example, if no ETCO2 values are measured, then the tube has not been properly placed. Likewise, if several ETCO2 values are identified and an initial baseline is determined after tube placement, then the values are indicative of both a verification of a successful tube placement (i.e., from the detected breaths) as well as an indication of the patient's condition (e.g., 35-45 mm Hg is a typical value for a healthy patient, thus values lower than that provide an indication that the patient is struggling to breath).

Additionally, another example of a baseline, which also disclosed in detail below, it to determine a dynamic baseline. This dynamic baseline may be based, for example, on continually updated ETCO2 values (or other physiological values, such as TTI and/or acoustic) measured after the tube placement. This dynamic baseline may operate similar to a moving average. As newer ETCO2 values, for example, are detected by the medical device, the newer values are included in the dynamic baseline determination simultaneously, older values decay or age out of the baseline determination. One benefit of this type of baseline is that it provides insight into the condition of the patient for a period of times spanning multiple detected physiological values.

Returning to FIG. 16C, Next, the medical device 202 may set a dynamic baseline equal to the initial baseline in step 1478. The dynamic baseline is described in further detail below with respect to step 1492. The dynamic baseline may change as more breaths are detected, whereas the initial baseline remains constant. Then, the medical device 202 continues to detect breaths and measuring ETCO2 values in step 1480. In the next step 1482, the medical device 202 calculates an average ETCO2 based on "X" numbers of consecutive breaths. This average of consecutive breaths helps to reduce false alarms due to (e.g.,) of noise and/or outlier data. In general, "X" may be a relatively small number (e.g., 2-5 breaths), yet sufficient so that a pattern of breaths may be detected (to eliminate noise/outliers).

The medical device 202 may then determine if the averaged ETCO2 value is greater than, for example, 50% of the initial baseline and/or dynamic baseline in step 1484. The initial baseline and/or dynamic baseline are additional specific examples of predefined criterion of physiological measurement(s) that may be satisfied to verify that a ventilation breath has reached the lungs. If the measured ETCO2 value is greater than, for example, 50% of the initial baseline and/or dynamic baseline, then the medical device 202 generates an alert such as "CO2 Change, Check Patient" in step 1486, for example, to check for spontaneous respiration (e.g., unassisted breathing) or other conditions of the patient. The purpose of checking the averaged ETCO2 against both the dynamic baseline and initial baseline is to enable the medical device to track the general trend of the patient, as well as to enable to the medical device to be able to compare the current condition of the patient to their original condition (when first measured). For example, a patient that has values that are slowly increasing or decreasing may never trigger an alert (e.g., steps 1486, 1490), but overall the patient's condition, as compared to their original condition, may be changing. While a threshold percentage change of 50% is provided in this example, it can be appreciated that other threshold percentage changes may be employed.

If the averaged ETCO2 value is not greater than 50% (or another suitable threshold percentage) of the initial baseline and/or dynamic baseline, then the medical device 202 determines if the averaged ETCO2 value is less than 50% (or another suitable threshold percentage) of the initial baseline and/or dynamic baseline in step 1488. In this case, if the averaged ETCO2 value is less than 50% of the initial baseline and/or dynamic baseline, then the medical device 202 generates an alert such as "Low CO2, Check Airway" in step 1490. For instance, a substantial drop in ETCO2 (e.g., greater than 50% drop) could indicate dislodgment of the endotracheal tube. If the averaged ETCO2 value is not less than 50% of the initial baseline and/or dynamic baseline, then the medical device 202 removes the oldest value (or possibly several values) from the average calculation and recalculates the average with the most recent value (or possibly several values) to update the dynamic baseline in step 1492. This dynamic baseline creates a "moving average", which helps to track trends in the ETCO2 values.

FIG. 16D is similar to FIG. 16C, except that the instead of using ETCO2 values to measure breathing, the medical device 202 uses for transthoracic impedance (TTI) values. A benefit of using TTI is that TTI is not a metabolic measure, but rather a measure of air having entered, or not entered, the lungs. Accordingly, TTI provides a measure that may provide more sensitivity to mechanical changes independent of the patient's metabolic condition. As such, TTI may identify smaller variations, which be indicative of problems, which might otherwise go undetected with other means. While FIGS. 16C and 16D are described as being separate embodiments, the medical device could be implemented in conjunction.

Returning to FIG. 16D, in the first step, 1471 the medical device 202 detects a predefined number of breaths (e.g., between 3-10 detected breaths). As before, the number of predefined breaths may be pre-programmed into the medical device 202. In the next step 1473, the medical device 202 may identify outlier values and/or trends. Similar to step 1472 above, the identification of trends are examples of predetermined criterion. Then, generates an alert if the outlier or trend indicates deterioration of the patient in step 1475. This may be accomplished by, for example, comparing each measured TTI of each of other the detected values breaths and identifying deviations and or trends of widely increasing trends (similar to the methods described with respect to FIG. 16C).

In step 1477, the medical device 202 may calculate an average TTI value (e.g., in mm Hg) based on the values of the detected predefined numbers of breaths. This calculated average may provide an initial baseline that provides a point for future comparison of detected and measured TTI values. Next, the medical device 202 may set a dynamic baseline initially equal to the initial baseline in step 1479. The dynamic baseline may change as more breaths are detected, whereas the initial baseline remains constant. Then, the medical device 202 continues to detect breaths and measuring TTI values in step 1481. In the next step 1483, the medical device 202 calculates an average TTI based on "X" numbers of consecutive breaths. This average of consecutive breaths helps to reduce false alarms due to (e.g.,) of noise and/or outlier data.

The medical device 202 then determines if the averaged TTI value is greater than, for example, 50% of the initial baseline and/or dynamic baseline in step 1484. If the measured TTI value is greater than, for example, 50% of the initial baseline and/or dynamic baseline, then the medical device 202 generates an alert such as, "Check Airway" in step 1487 as it may be possible that the tube has entered one of the lobes in the lung. As discussed previously, it is desirable for the tube to remain in the trachea so that both lungs may receive air from ventilation breaths. As before, the purpose of checking the averaged TTI to both the dynamic baseline and initial baseline is to enable the medical device to track the general trend of the patient, as well as to enable to the medical device to be able to compare the current condition of the patient to their original condition. For example, a patient that has values that are slowly increasing or decreasing may never trigger an alert (e.g., steps 1487, 1491).

If the averaged TTI value is not greater than 50% (or another appropriate percentage threshold) of the initial baseline and/or dynamic baselines, then the medical device 202 determines if the averaged TTI value is less than 50% (or another appropriate percentage threshold) of the initial baseline and/or dynamic baseline in step 1489. If the averaged TTI value is less than 50% of the initial baseline and/or dynamic baseline, then the medical device 202 may generate an alert such as "Check tube" as the tube may have become dislodged in step 1491. If the averaged TTI value is not less than 50% of the initial and/or dynamic baselines, then the medical device 202 removes the oldest value (or possibly several values) from the average calculation and recalculates the average with the most recent value (or possibly several values) to update the dynamic baseline in step 1493. This dynamic baseline creates a "moving average," which helps to track trends in the ETCO2 values.

Figure 16E:
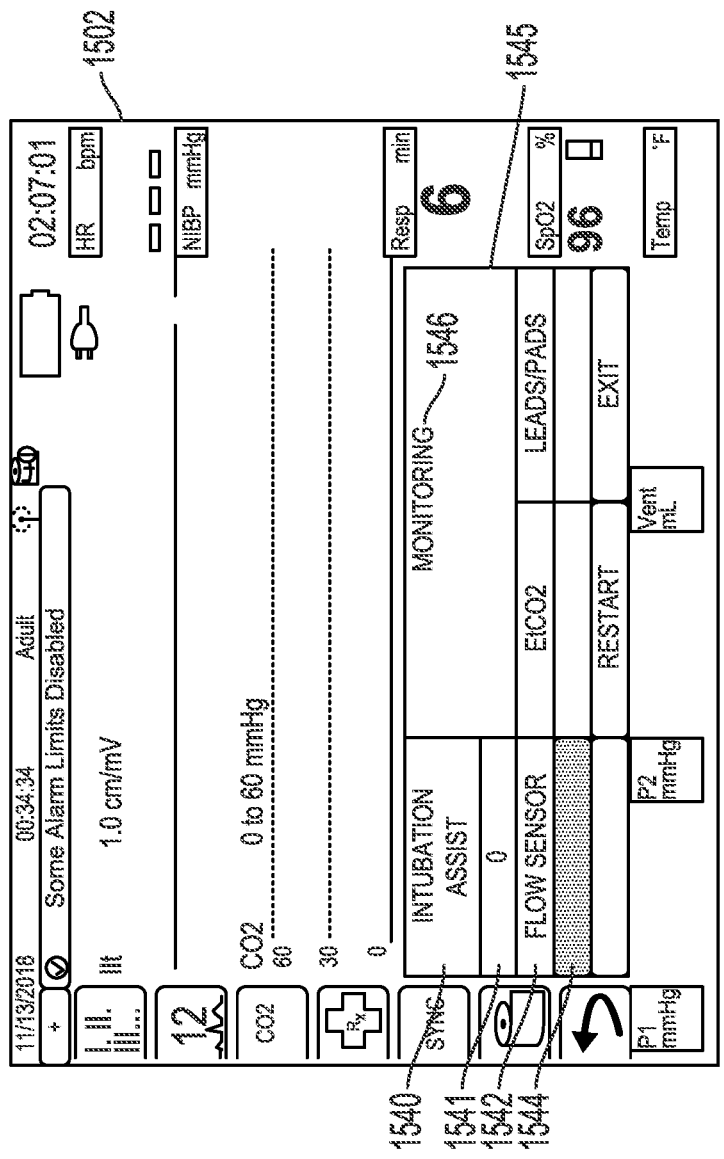
FIG. 16E is an exemplary user interface (dashboard) displayed on a medical device during tube verification and illustrates detection of airflow by a flow sensor in accordance with an embodiment.

FIG. 16E is an exemplary user interface (dashboard) displayed on the medical device and/or portable computing device during the post-intubation airway monitoring for verifying that the tube remains properly placed, and illustrates usage of an airflow sensor 127 in detecting and confirming that a positive pressure breath (e.g., oxygen ventilation) has been appropriately given to the patient or that the patient is spontaneously breathing.

As illustrated in the figure, the screen 1502 includes a verification mode dashboard 1545, which may be presented along with the intubation assist dashboard as indicated in box 1540. Additionally, a status indicator 1546 provides the current status (e.g., monitoring). The timer appears in box 1541, an indication of the type of flow sensor is provided in box 1542, and confirmation box 1544 provides an indication that a delivery of a positive pressure breath (e.g., oxygen ventilation) has been given or that the patient is making spontaneous breathing efforts. In the illustrated example, the box 1544 is shaded. However, in one embodiment, the display may change a color (e.g., green) to indicate a breath has been detected. Alternatively, upon expiration of a timer, it may turn red to indicate a failure to detect the breath.

Figure 16F:
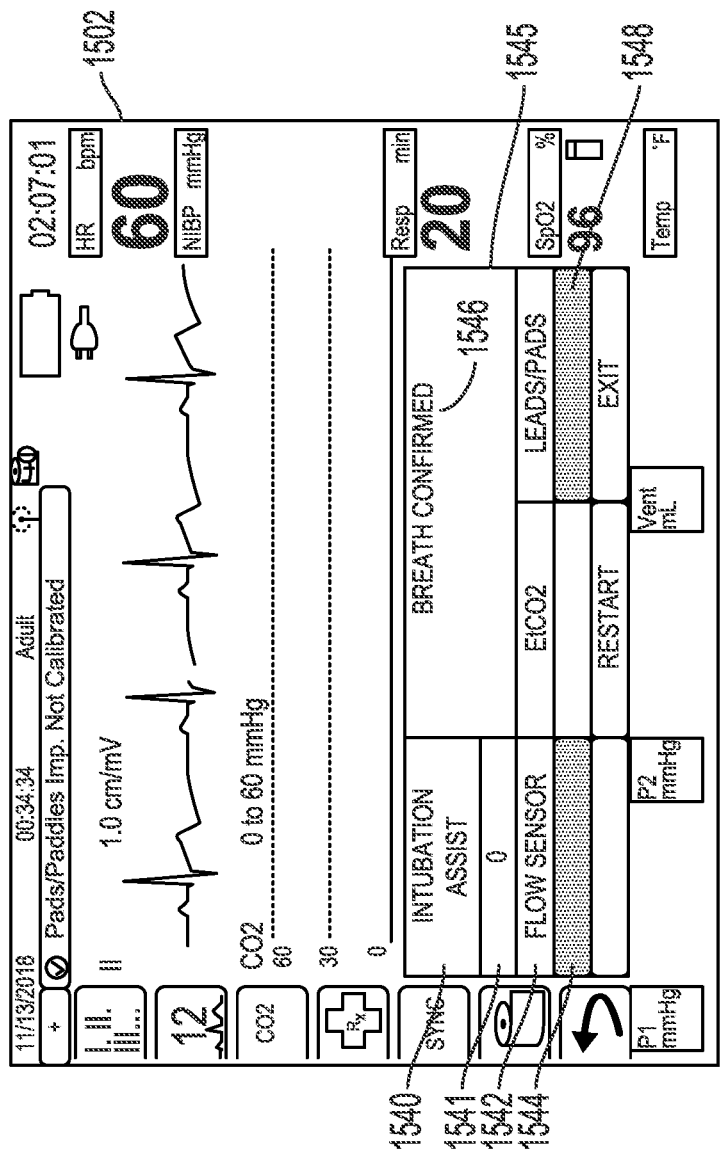
FIG. 16F is an exemplary user interface (dashboard) displayed on a medical device during the tube verification and illustrates the detection of a breath from transthoracic impedance measured by electrodes in accordance with an embodiment.

FIG. 16F is an exemplary user interface (dashboard) displayed on the medical device and/or portable computing device during the post-intubation tube monitoring and illustrates the detection of lung inflation due to a change in impedance from electrodes 125a, 125b, correlated with the detected breath from the airflow sensor, indicating that the breath has reached the patient's lungs. As illustrated, upon detection that a breath has reached the lungs, a notification in the status indicator 1546 indicates that a breath was confirmed and also provides an indication in box 1548 (e.g., turning green) as to which physiological sensor detected the breath. As before, the box may change a color (e.g., green) to indicate a breath has been detected. Alternatively, upon expiration of a timer, it may turn red to indicate a failure to detect the breath.

Figure 16G:
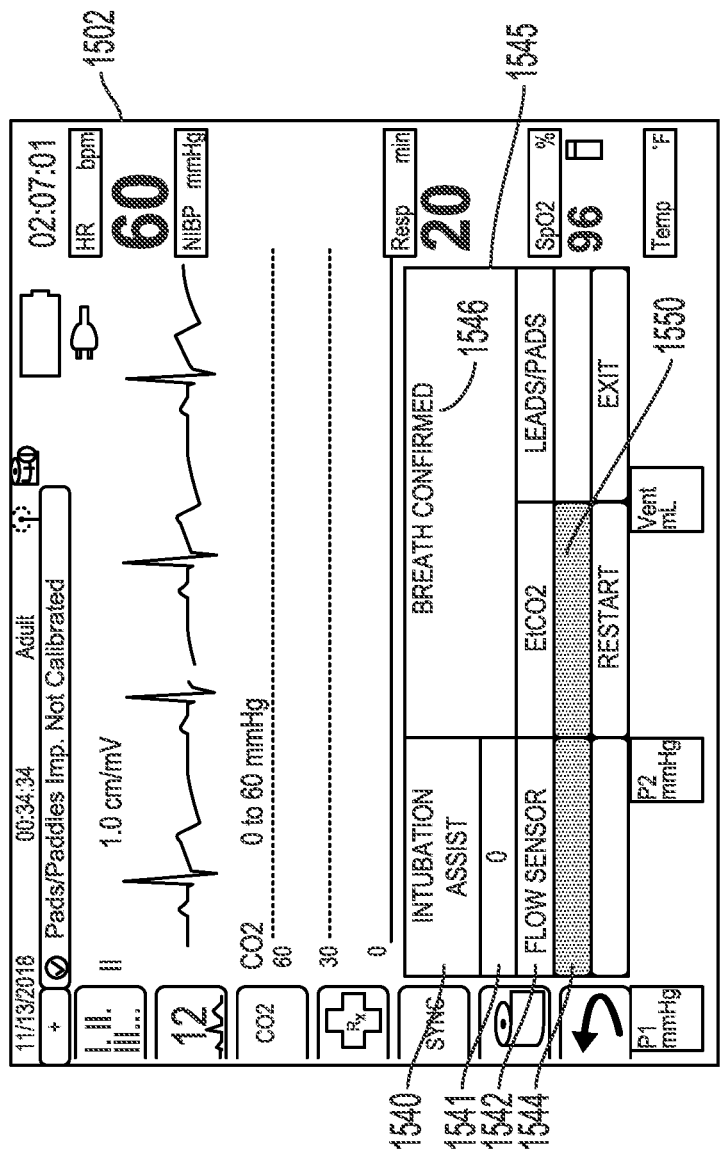
FIG. 16G is an exemplary user interface (dashboard) displayed on a medical device during the tube verification step and illustrates the detection of a breath by a capnography sensor in accordance with an embodiment.

FIG. 16G is an exemplary user interface (dashboard) displayed on the medical device and/or portable computing device during the post-intubation airway monitoring step and illustrates the detection that the breath has reached the patient's lungs from the capnography sensor 218, in detecting a CO2 waveform. Here, the CO2 waveform is correlated with the detected breath from the airflow sensor. As illustrated, upon detection of a sufficient amount of CO2 a notification in the status indicator 1546 indicates that a breath was confirmed and also provides an indication in box 1550 (e.g., turning green) as to which physiological sensor detected the breath.

Figure 16H:
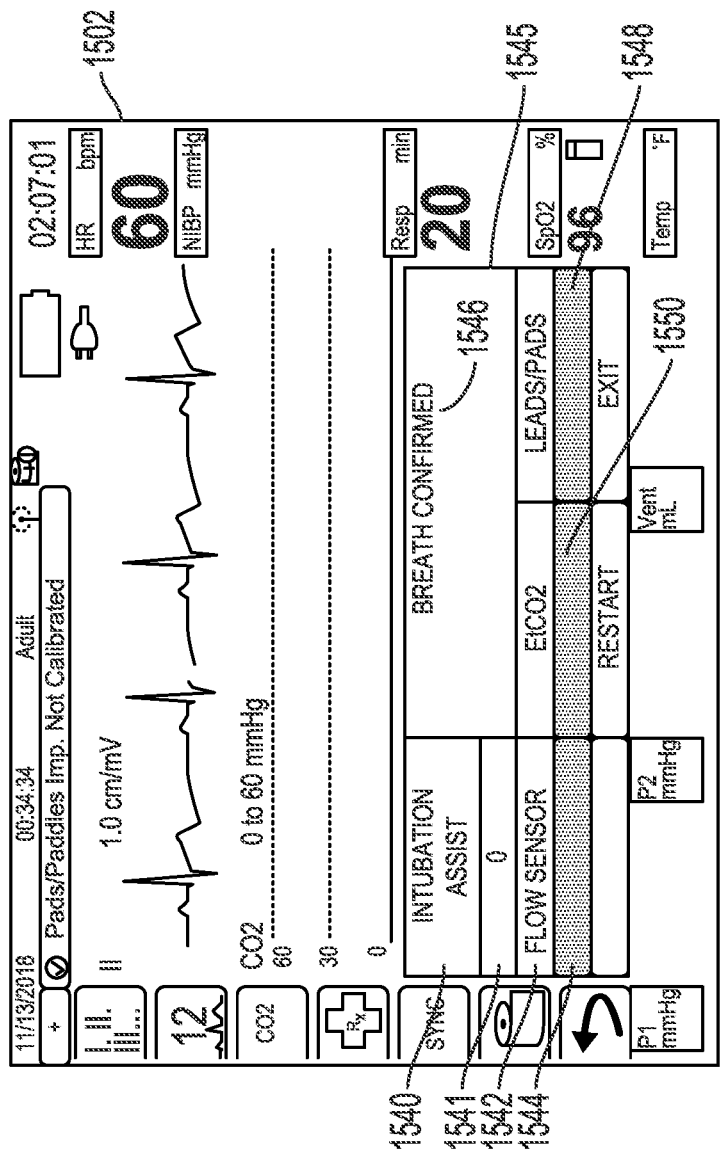
FIG. 16H is an exemplary user interface (dashboard) displayed on a medical device during the tube verification step and illustrates the detection of a breath from both capnography sensor and electrodes in accordance with an embodiment.

FIG. 16H is an exemplary user interface (dashboard) displayed on the medical device and/or portable computing device during the post-intubation tube monitoring step and illustrates the detection that the breath has properly reached the patient's lungs from the capnography sensor 218 (in detecting a CO2 waveform) and electrodes 125a, 125b (in detecting a change in transthoracic impedance). As illustrated, upon such confirmation from both capnography and impedance, a notification in the status indicator 1546 indicates that a breath was confirmed and also provides an indication in boxes 1448 and 1550 (e.g., turning green) that both physiological sensors detected the breath.

Figure 16I:
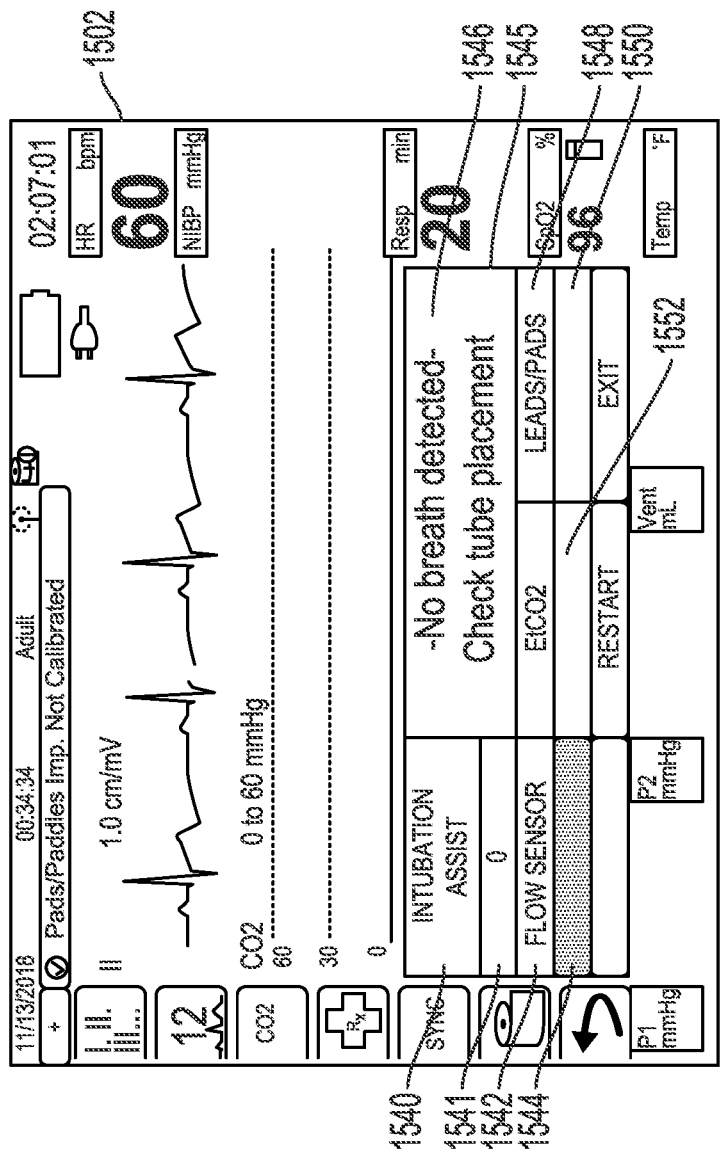
FIG. 16I is an exemplary user interface (dashboard) displayed on a medical device during the tube verification and illustrates the failure to detect a breath in accordance with an embodiment.

FIG. 16I is an exemplary user interface (dashboard) displayed on the medical device and/or portable computing device during the post-intubation tube monitoring and illustrates the failure to detect that the positive pressure breath has reached the patient's lungs, i.e., the intubation tube is misplaced, and the alert indicating a failed tube placement. Alternatively, the medical device may only display alerts when failure is detected to prevent a cluttering of the screen or one or more alerts every time the BVM is used and/or a corresponding breath is detected. For example, an alert may be displayed when a parameter mismatch (e.g., change in TTI and/or EtCO2 past a threshold amount) is detected, indicating that the intubation tube should be checked. Typically, these would be user configurable settings so that each user, rescuer, or team, could change the setting to their own liking.

As described previously, the failure of a capnography sensor 218 or electrodes to detect a proper breath may be due to a number of reasons such as endotracheal tube 129 of FIG. 1B becoming dislodged from the subject's trachea or the subject may have stopped breathing. Alternatively, a failure to detect a proper breath may be caused by a break or leak in the breathing circuit (e.g., between the BVM and the capnography sensor and/or the ET tube), or a break/leak between the airway sensor and the capnography sensor). Additionally, it may provide an indication that the tube may have been placed down the esophagus (e.g., the pathway leading to the stomach). While the above embodiment describes usage of a flow sensor to detect the presence of airflow in the patient airway in the context of post-intubation monitoring, it can be appreciated that the flow sensor may also be used in the context of initial intubation assist and confirmation that the tube has been properly placed. For example, as discussed above, the air flow sensor may be used to detect that a positive pressure breath has initially been given. Then a timer may be initiated to confirm from one or more physiological sensors (e.g., capnography, TTI, acoustic sensor) that the positive pressure breath has entered the patient's lungs. Then, one or more instructions for the rescuer to auscultate multiple sites (e.g., left lung, right lung, abdomen, left axillary, right axillary) to confirm whether the intubation tube has been properly placed may be given. The rescuer may then be required to input into the medical device or portable computing device a positive or negative result of auscultation in order to complete the intubation procedure.

As also discussed herein, it can be appreciated that the air flow sensor may be used in combination with an oxygen sensor to detect the presence of oxygen in the patient's airway. This way, it can be confirmed that a positive pressure breath is not only applied to the patient, but that the positive pressure breath includes a desired amount/concentration of oxygen.

Additionally or alternatively, the medical device may identify whether it is likely that the patient is in cardiac arrest, for example, based on the ECG waveform, or whether chest compressions are being applied to the patient based on signals acquired from a motion sensor (e.g., accelerometer) located on the sternum. It may be beneficial to identify which state the patient is in because the TTI and CO2 signal will typically look markedly different depending on their state. If the patient is in one of the states where the sensors are unable to reliably detect/identify signals (e.g., TTI during CPR chest compressions), then an alert may be displayed indicating that the CO2 or TTI signals may be unreliable, or simply might not use or display results from CO2 or TTI. For example, if chest compressions are being applied to the patient, as detected by the motion sensor of a chest compression sensor located on the sternum of the patient, then artifacts from the compressions may show up in the CO2 or TTI waveforms. Without proper signal artifact removal, such waveforms may be less reliable for purposes of confirming proper intubation tube placement. Accordingly, for certain embodiments, intubation confirmation procedures discussed herein may apply to cases where the patient is not undergoing chest compressions.

Figure 17:
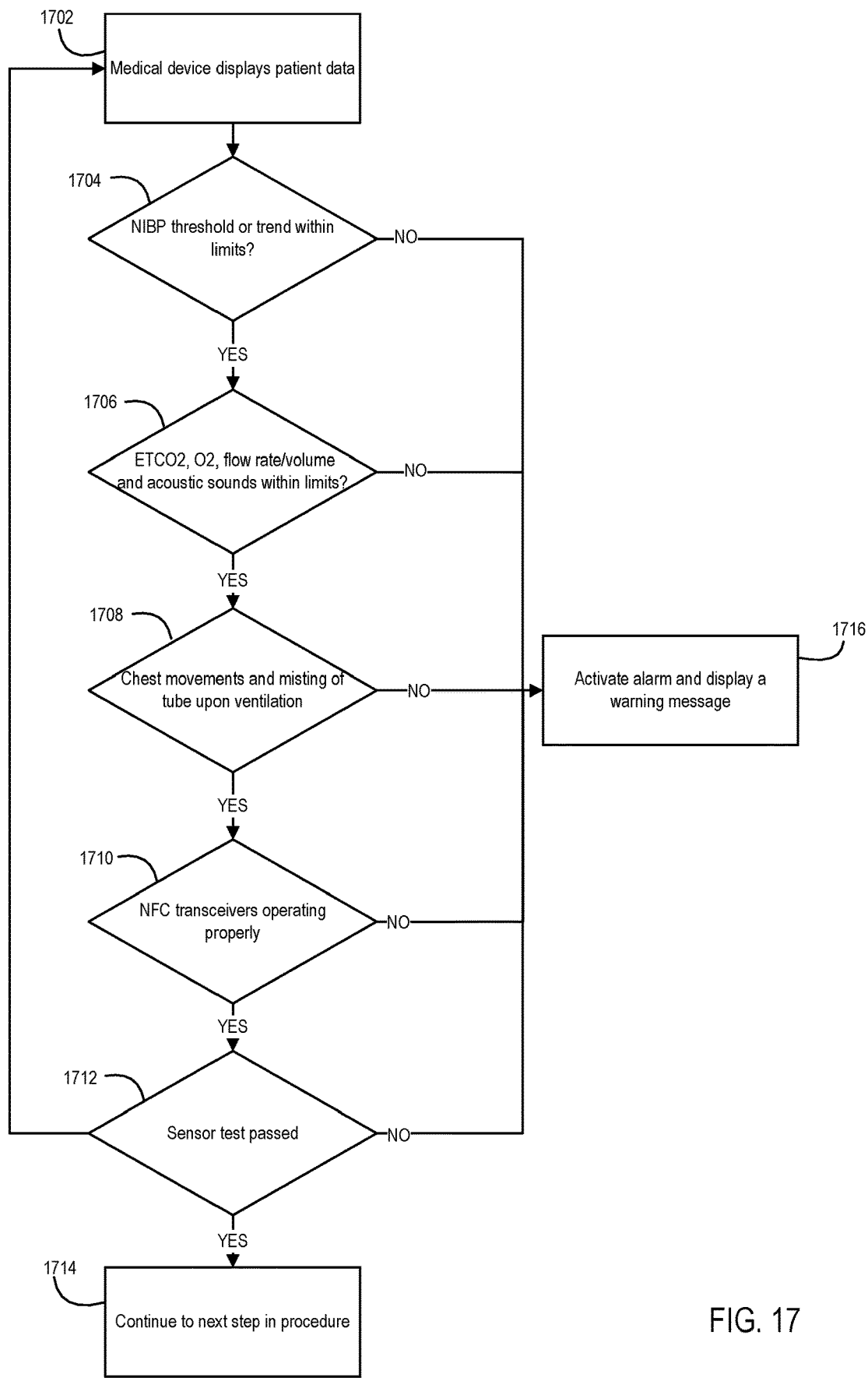
FIG. 17 is a flow chart illustrating steps performed during the post verification of endotracheal tube placement in accordance with an embodiment.

FIG. 17 is a flow chart illustrating typical steps performed after the verification of the endotracheal tube placement in accordance with embodiments of the present disclosure. In general, the post verification monitoring is related to ensuring that the successful tube placement is performing as expected and that the patient is, and remains, in stable condition. While the illustrated embodiment shows a series of sequential steps, in practice, the determinations made by the medical device may be operating virtually simultaneously.

In the first step 1702, the medical device displays patient data. In the next step 1704, the medical device 202 determines whether NIBP is below a threshold (e.g., a systolic value less than 120 and/or a diastolic value less than 80) to monitor for hypotension, which often results from intubation. Alternatively, the medical device monitors the trending NIBP to determine the "direction" the NIBP is heading. The NIBP threshold is checked for hypotension, which is common due to diminished venous return during the RSI procedure. If the NIBP is below a preset threshold then, the medical device may provide an alert for the rescuer to take intervening steps to increase blood pressure (e.g., providing medication). The medical device 202 further determines whether the intubation parameters (e.g., ETCO2, O2, oxygen saturation, flow rate/volume) and measured sounds fall within acceptable limits in step 1706. In various embodiments, the various physiologic data and airway gas measurements may be closely monitored while the ET tube is in place, and the desired ranges for each of the parameters may be preconfigured for monitoring mode. If patient's intubation parameters (e.g., ETCO2, SpO2, flow rate/volume, vital signs) fall outside of the desired range (e.g., greater than 50 mmHg, below 88%, and 400 mL, respectively), then the medical device may provide an alarm and/or notification for the rescuer to determine next steps.

If the ETCO2, O2, flow rate/volume and measured sounds are being properly displayed, then the medical device 22 determines if the chest movements and either misting of tube or via increased humidity of the exhaled gas upon ventilation are present in step 1708 due to the distal tip of the tube being in proximity to the lungs. In one example, misting of the tube may be detected via an optical window incorporated into the flow sensor. An LED is positioned to the side of the window and a light sensor is positioned outside the window. The optical window when misted with the humidity from the exhalation will be bright from the light scattered due to the condensation on the interior of the window. Alternatively, increased humidity in the exhaled gas may be measured via a humidity sensor, such as the Honeywell HIH-4000-002, contained in the flow sensor. If the chest movements, misting, and/or increased humidity of the tube upon ventilation are present, then the medical device 202 determines whether NFC transceivers on the flow sensor and ET tube are operating in step 1710. If the NFC transceivers on the flow sensor and ET tube are operating and the proximity between the transceivers is confirmed, then the medical device 202 determines if the sensor test passed 1712. This "sensor test" ensures that the various sensors of the medical device are operational and are providing relevant data.

If all of these conditional steps are completed successfully, then the medical device continues monitoring the patient, but also is able to move to the next step in the procedure in step 1714. However, if any of the steps fail, then the medical device may activate an alarm and displays a warning message to the user. Typically, the medical device displays a fault specific message indicating which step failed.

Figure 18:
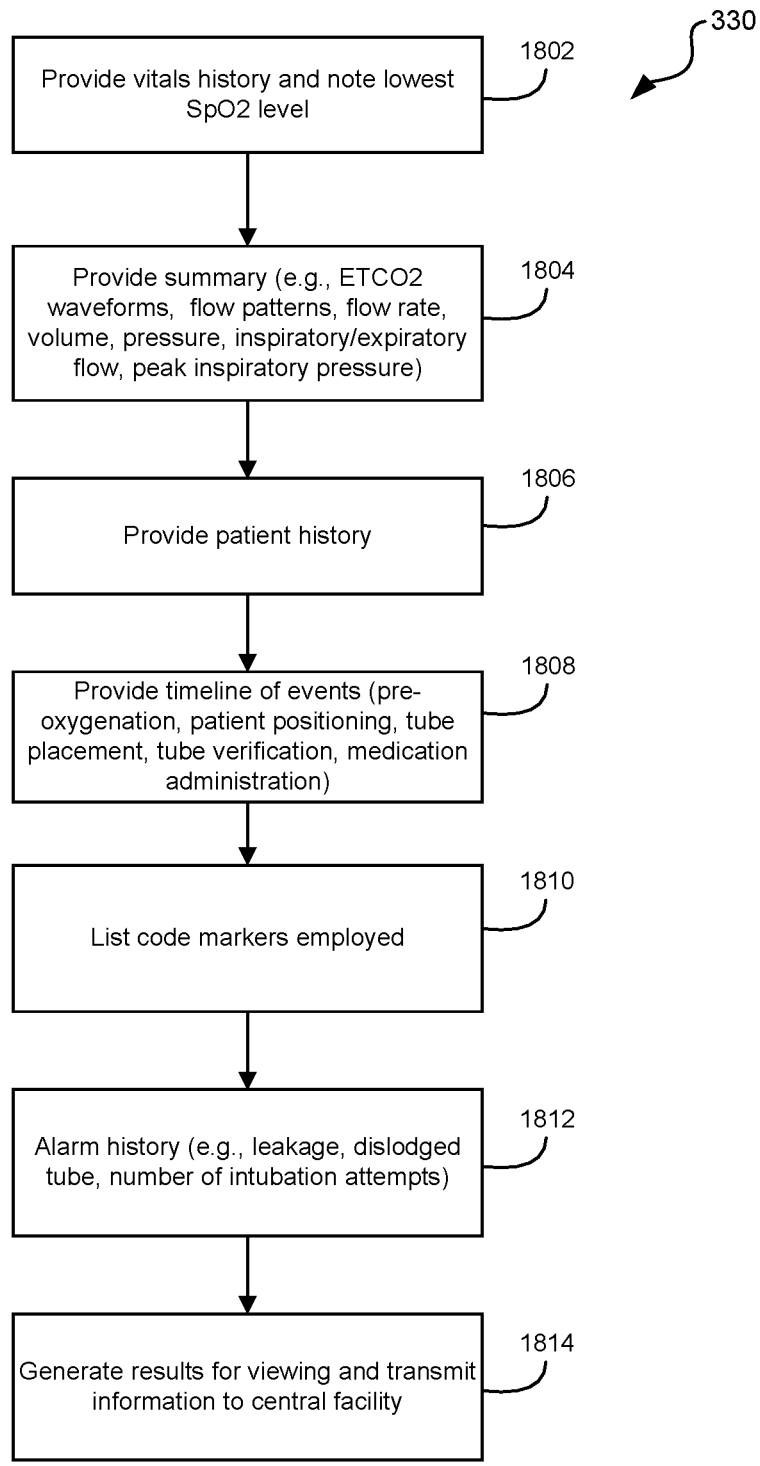
FIG. 18 is a flow chart illustrating steps performed during post-case debriefing in accordance with an embodiment.

FIG. 18 is a flow chart illustrating typical steps performed during the post-case debriefing in accordance with various embodiments.

In a typical implementation, the data from the post case debrief is transmitted to a central facility 224 or a personal computing device 225 (e.g., a tablet, laptop, or smartphone). Alternatively, the information could be stored in the memory of the medical device 202 and then transferred to a memory device (e.g., a USB memory stick) to transfer the information to the central facility. In still yet another embodiment, the information can simply be displayed on the display of the medical device. Additionally, the medical device 202 may present the post case information and transmit the information to a central facility 224.

In the first step 1802, the medical device may provide a history of the patient vitals (e.g., intubation parameters), specifically noting the significant physiologic and airway gas parameters experienced by the patient during the procedure. Next, in step 1804, the medical device 202 may provide a flow history of relevant information (e.g., ETCO2 waveforms, flow patterns, flow rate, volume, pressure, inspiratory/expiratory flow, peak inspiratory pressure) for the patient during the tube placement procedure. The medical device 202 may also provide any patient history information that was collected in step 1806. Next, in step 1808, the medical device 202 may provide timeline of events, which may also include the duration of each event, e.g., preoxygenation, patient positioning, tube placement, tube verification, and medication administration, during the procedure along with non-patient data related to the rescuers, device performance/identification and environmental conditions.

In step 1810, the medical device 202 lists code markers employed during the procedure. The medical device 202 provides an alarm history (e.g., leakage, dislodged tube, number of intubation attempts, etc.). In the last step 1814, this information is transmitted to the central facility.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks.

The computing devices described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing devices described herein may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (e.g., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify aspects of the present disclosure. Also, a number of operations may be undertaken before, during, or after the above elements are considered. Also, technology evolves and, thus, many of the elements are examples and do not bound the scope of the disclosure or claims. Accordingly, the above description does not bound the scope of the claims.

Other embodiments are within the scope of the present disclosure. For example, due to the nature of software, functions described above can be implemented using software, hardware, firmware, hardwiring, or combinations of any of these. Features implementing functions may also be physically located at various locations, including being distributed such that portions of functions are implemented at different physical locations.

What is claimed is:

1. A medical system for assisting a rescuer with an intubation procedure with an endotracheal (ET) tube for a patient, the system comprising:
   one or more airflow sensors configured to obtain data indicative of airflow in the patient's airway and data indicative of inspiratory tidal volume and expiratory tidal volume;
   one or more physiological sensors to obtain configured to obtain physiological information regarding airflow in the patient's lungs; and
   a patient monitoring device communicatively coupled to the one or more airflow sensors, the patient monitoring device comprising:
   a user interface comprising a display; and
   at least one processor and memory configured to:
      receive the data indicative of airflow in the patient's airway and the physiological information regarding airflow in the patient's lungs,
      determine presence of airflow in the patient's airway based on the data indicative of airflow,
      analyze the physiological information regarding airflow in the patient's lungs to provide an indication of ET tube placement,
      determine that a leak may be present in relation to the ET tube based on an analysis of the expiratory tidal volume relative to the inspiratory tidal volume,
      based on the indication of ET tube placement and the determination that the leak may be present in relation to the ET tube, output to the display of the user interface an alert to check the ET tube in relation to the leak that may be present.

2. The system of claim 1, wherein analyzing the expiratory tidal volume relative to the inspiratory tidal volume comprises determining whether the expiratory tidal volume and the inspiratory tidal volume are approximately equal.

3. The system of claim 1, wherein analyzing the expiratory tidal volume relative to the inspiratory tidal volume comprises determining whether the expiratory tidal volume is significantly smaller than the inspiratory tidal volume.

4. The system of claim 1, wherein the alert to check the ET tube in relation to the leak that may be present comprises mitigation instructions relating to the leak that may be present.

5. The system of claim 1, wherein the one or more physiological sensors comprises at least one of: at least one capnography sensor, at least one impedance sensor, and at least one acoustic sensor.

6. The system of claim 1, wherein the at least one processor is configured to compare one or more measured physiological parameters to one or more thresholds in the analysis of the physiological information regarding airflow in the patient's lungs.

7. The system of claim 6, wherein the at least one processor in configured to compare measured end-tidal carbon dioxide (ETCO2) to at least one threshold in the analysis of the physiological information regarding airflow in the patient's lungs.

8. The system of claim 6, wherein the at least one processor is configured to compare the one or more measured physiological parameters to at least one baseline associated with the one or more measured physiological parameters in the analysis of the physiological information regarding airflow in the patient's lungs.

9. The system of claim 8, wherein the at least one baseline is a continually updated dynamic baseline.

10. The system of claim 6, wherein the at least one processor is configured to make determinations regarding, and use in the analysis of the physiological information regarding airflow in the patient's lungs, at least one of: falling outside of a range associated with at least one of the measured one or more physiological parameters, and falling within a range associated with at least one of the measured one or more physiological parameters.

11. The system of claim 7, wherein the at least one processor is configured to compare the measured ETCO2 to at least one ETCO2 baseline in the analysis of the physiological information regarding airflow in the patient's lungs.

12. The system of claim 9, wherein the at least one processor is configured to determine and use deviation from the dynamic baseline in the analysis of the physiological information regarding airflow in the patient's lungs.

13. The system of claim 1, wherein the data indicative of airflow in the patient's airway comprises at least one of: inspiratory flow rate and expiratory flow rate.

14. The system of claim 1, wherein the at least one processor is configured to:
determine that the ET tube may be dislodged, and
based on the determination that the ET tube may be dislodged, output to the display of the user interface an alert to check the ET tube for possible dislodgement.

15. The system of claim 1, wherein the at least one processor is configured to:
determine that the ET tube may be misplaced, and
based on a determination that the ET tube may be misplaced, output to the display of the user interface an alert indicating possible ET tube misplacement.

16. The system of claim 15, wherein the alert indicating possible ET tube misplacement indicates that the ET tube may be misplaced in the patient's esophagus.

17. A method, executed by a processor of a patient monitoring device, the patient monitoring device comprising the processor and a memory, for assisting a rescuer with an intubation procedure with an endotracheal (ET) tube for a patient, the method comprising:
obtaining from one or more airflow sensors coupled to the patient monitoring device, and storing in the memory of the patient monitoring device, data indicative of airflow in the patient's airway and data indicative of inspiratory tidal volume and expiratory tidal volume;
obtaining from one or more physiological sensors coupled to the patient monitoring device, and storing in the memory of the patient monitoring device, physiological information regarding airflow in the patient's lungs;
determining presence of airflow in the patient's airway based on the data indicative of airflow in the patient's lungs;

analyzing the physiological information regarding airflow in the patient's lungs to provide an indication of ET tube placement;
determining that a leak may be present in relation to the ET tube based on an analysis of the expiratory tidal volume relative to the inspiratory tidal volume; and
outputting based on the indication of ET tube placement and the determination that the leak may be present in relation to the ET tube, to a display of a user interface of the patient monitoring device, an alert to check the ET tube in relation to the leak that may be present.

18. The method of claim 17, wherein analyzing the expiratory tidal volume relative to the inspiratory tidal volume comprises determining whether the expiratory tidal volume and the inspiratory tidal volume are approximately equal.

19. The method of claim 17, wherein analyzing the expiratory tidal volume relative to the inspiratory tidal volume comprises determining whether the expiratory tidal volume is significantly smaller than the inspiratory tidal volume.

20. The method of claim 17, wherein the alert to check the ET tube in relation to the leak that may be present comprises mitigation instructions relating to the leak that may be present.

21. The method of claim 17, comprising comparing one or more measured physiological parameters to one or more thresholds in the analysis of the physiological information regarding airflow in the patient's lungs.

22. The method of claim 21, comprising comparing measured end-tidal carbon dioxide (ETCO2) to at least one threshold in the analysis of the physiological information regarding airflow in the patient's lungs.

23. The method of claim 21, comprising comparing the one or more measured physiological parameters to at least one baseline associated with the one or more measured physiological parameters in the analysis of the physiological information regarding airflow in the patient's lungs.

24. The method of claim 23, wherein the at least one baseline is a continually updated dynamic baseline.

25. The method of claim 22, comprising comparing the measured ETCO2 to at least one ETCO2 baseline in the analysis of the physiological information regarding airflow in the patient's lungs.

26. The method of claim 24, comprising determining and using deviation from the dynamic baseline in the analysis of the physiological information regarding airflow in the patient's lungs.

27. The method of claim 17, comprising:
determining that the ET tube may be dislodged, and
based on the determination that the ET tube may be dislodged, outputting to the display of the user interface an alert to check the ET tube for possible dislodgement.

28. The method of claim 17, comprising:
determining that the ET tube may be misplaced, and
based on a determination that the ET tube may be misplaced, outputting to the display of the user interface an alert indicating possible ET tube misplacement.

29. The method of claim 28, wherein the alert indicating possible ET tube misplacement indicates that the ET tube may be misplaced in the patient's esophagus.

* * * * *